(12) United States Patent
Park et al.

(10) Patent No.: US 12,144,827 B2
(45) Date of Patent: Nov. 19, 2024

(54) ROR1 TARGETING CHIMERIC ANTIGEN RECEPTOR

(71) Applicant: Lyell Immunopharma, Inc., South San Francisco, CA (US)

(72) Inventors: Spencer Park, Seattle, WA (US); Queenie Vong, South San Francisco, CA (US); Blythe Sather, South San Francisco, CA (US); Byoung Ryu, South San Francisco, CA (US); Marc Lajoie, South San Francisco, CA (US); Howell Moffett, South San Francisco, CA (US); Brian Weitzner, South San Francisco, CA (US); Yun Song, South San Francisco, CA (US); Scott Boyken, South San Francisco, CA (US); Neeraj Sharma, South San Francisco, CA (US); Shobha Potluri, South San Francisco, CA (US); Bijan Boldajipour, South San Francisco, CA (US)

(73) Assignee: Lyell Immunopharma, Inc., South San Francisco, CA (US)

( * ) Notice: Subject to any disclaimer, the term of this patent is extended or adjusted under 35 U.S.C. 154(b) by 87 days.

(21) Appl. No.: 17/680,024

(22) Filed: Feb. 24, 2022

(65) Prior Publication Data

US 2023/0022654 A1 Jan. 26, 2023

Related U.S. Application Data

(60) Provisional application No. 63/309,393, filed on Feb. 11, 2022, provisional application No. 63/263,229, filed on Oct. 28, 2021, provisional application No. 63/153,878, filed on Feb. 25, 2021.

(51) Int. Cl.
| | |
|---|---|
| A61K 35/17 | (2015.01) |
| A61P 35/00 | (2006.01) |
| C07K 14/71 | (2006.01) |
| C07K 16/40 | (2006.01) |
| C12N 15/62 | (2006.01) |

(52) U.S. Cl.
CPC .............. *A61K 35/17* (2013.01); *A61P 35/00* (2018.01); *C07K 14/71* (2013.01); *C07K 16/40* (2013.01); *C12N 15/62* (2013.01); *C07K 2317/565* (2013.01)

(58) Field of Classification Search
CPC ......... A61P 35/00; C07K 14/71; C07K 16/40; C07K 2317/565; C12N 15/62
See application file for complete search history.

(56) References Cited

U.S. PATENT DOCUMENTS

| | | |
|---|---|---|
| 4,683,195 A | 7/1987 | Mullisus et al. |
| 5,858,358 A | 1/1999 | June et al. |
| 5,883,223 A | 3/1999 | Gray |
| 6,352,694 B1 | 3/2002 | June et al. |
| 6,534,055 B1 | 3/2003 | June et al. |
| 6,692,964 B1 | 2/2004 | June et al. |
| 6,703,199 B1 | 3/2004 | Koide |
| 6,790,614 B1 | 9/2004 | Pippig et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,984,382 B1 | 1/2006 | Groner et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,572,631 B2 | 8/2009 | Berenson et al. |
| 8,802,374 B2 | 8/2014 | Jensen |
| 9,228,023 B2 | 1/2016 | Rohlff et al. |
| 9,316,646 B2 | 4/2016 | Rader et al. |
| 9,334,330 B2 | 5/2016 | Birkle et al. |
| 9,447,194 B2 | 9/2016 | Jensen |
| 9,469,676 B2 * | 10/2016 | Camphausen ......... C07K 14/47 |

(Continued)

FOREIGN PATENT DOCUMENTS

| | | |
|---|---|---|
| CN | 101851668 A | 10/2010 |
| CN | 106636210 B | 7/2019 |

(Continued)

OTHER PUBLICATIONS

Lynn, R. C., et al., "c-Jun overexpression in CAR T cells induces exhaustion resistance," Nature 576(7786): 293-300. doi: 10.1038/s41586-019-1805-z. Epub Dec. 4, 2019. (Year: 2019).*

Al-Lazikani, B., et al., "Standard conformations for the canonical structures of immunoglobulins," J Mol Biol 273(4):927-948, Academic Press, United States (Nov. 1997).

Balakrishnan, A., et al., "Analysis of ROR1 Protein Expression in Human Cancer and Normal Tissues," Clin Cancer Res 23(12):3061-3071, American Association for Cancer Research, United States (Jun. 2017).

(Continued)

*Primary Examiner* — Tracy Vivlemore
*Assistant Examiner* — Eric J Rogers
(74) *Attorney, Agent, or Firm* — Sterne, Kessler, Goldstein & Fox P.L.L.C.

(57) ABSTRACT

The present disclosure relates to polynucleotides encoding a chimeric polypeptide comprising a c-Jun polypeptide, a ROR1-binding protein, and a truncated EGF receptor. Also provided are cells (e.g., T cells) expressing CARs comprising a ROR1-binding protein and overexpressing a c-Jun polypeptide. Overexpression of c-Jun in CAR T cells confers improved properties, e.g., reducing or preventing exhaustion.

20 Claims, 13 Drawing Sheets

Figure 1A:
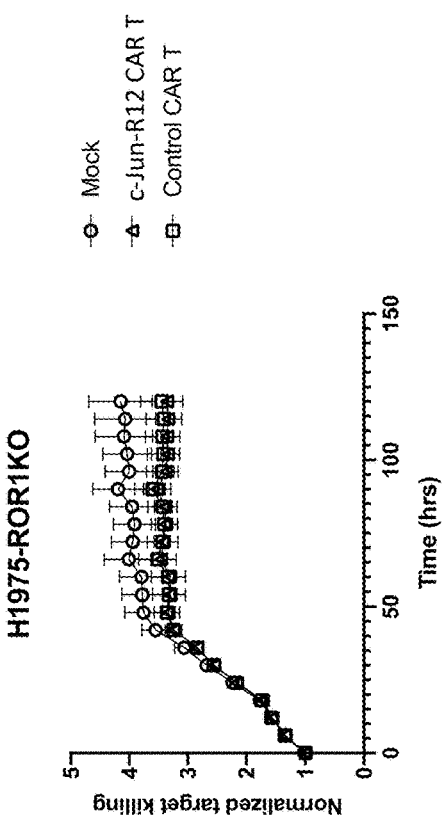

Specification includes a Sequence Listing.

(56) References Cited

U.S. PATENT DOCUMENTS

| | | |
|---|---|---|
| 9,580,685 B2 | 2/2017 | Jensen |
| 9,587,020 B2 | 3/2017 | Wu et al. |
| 9,758,586 B2 | 9/2017 | Rader et al. |
| 9,815,908 B2 | 11/2017 | Schonfeld et al. |
| 9,821,012 B2 | 11/2017 | Wu et al. |
| 9,938,350 B2 | 4/2018 | Kipps et al. |
| 9,987,308 B2 | 6/2018 | Riddell et al. |
| 10,100,281 B2 | 10/2018 | Jensen |
| 10,105,391 B2 | 10/2018 | Wu et al. |
| 10,172,885 B2 | 1/2019 | Pule et al. |
| 10,172,886 B2 | 1/2019 | Pule et al. |
| 10,189,903 B2 | 1/2019 | Jensen |
| 10,273,300 B2 | 4/2019 | Bedoya et al. |
| 10,400,215 B2 | 9/2019 | Riddell et al. |
| 10,428,141 B2 | 10/2019 | Orentas et al. |
| 10,544,201 B2 | 1/2020 | Schiffer-Mannioui |
| 10,603,378 B2 | 3/2020 | June et al. |
| 10,603,380 B2 | 3/2020 | Wiltzius |
| 10,618,959 B2 | 4/2020 | Rader et al. |
| 10,627,409 B2 | 4/2020 | Kipps et al. |
| 10,653,756 B2 | 5/2020 | Turtle et al. |
| 10,688,181 B2 | 6/2020 | Kipps et al. |
| 10,752,684 B2 | 8/2020 | Schiffer-Mannioui |
| 10,759,868 B2 | 9/2020 | Schiffer-Mannioui |
| 10,780,118 B2 | 9/2020 | Jensen et al. |
| 10,786,533 B2 | 9/2020 | Mohler et al. |
| 10,822,413 B2 | 11/2020 | Liu et al. |
| 10,889,652 B2 | 1/2021 | Chen et al. |
| 10,927,344 B2 | 2/2021 | Molleryd et al. |
| 10,968,275 B2 | 4/2021 | Balakrishnan et al. |
| 10,968,431 B2 | 4/2021 | Riddell et al. |
| 11,014,989 B2 | 5/2021 | Smith et al. |
| 11,058,722 B2 | 7/2021 | Pule et al. |
| 11,065,278 B2 | 7/2021 | Riddell et al. |
| 11,103,531 B2 | 8/2021 | Brentjens et al. |
| 11,155,615 B2 | 10/2021 | Wong et al. |
| 11,155,783 B2 | 10/2021 | Jensen |
| 11,162,065 B2 | 11/2021 | Fachin et al. |
| 11,167,015 B2 | 11/2021 | Geiger et al. |
| 11,273,219 B2 | 3/2022 | June et al. |
| 11,306,142 B2 | 4/2022 | Nathwani et al. |
| 11,312,787 B2 | 4/2022 | Kipps et al. |
| 11,400,115 B2 | 8/2022 | Ramsborg et al. |
| 11,400,117 B2 | 8/2022 | Mackall et al. |
| 11,453,719 B2 | 9/2022 | Orentas et al. |
| 11,458,167 B2 | 10/2022 | Jensen |
| 11,466,083 B2 | 10/2022 | Nathwani et al. |
| 11,518,815 B2 | 12/2022 | Olsen et al. |
| 11,723,925 B2 | 8/2023 | Nathwani et al. |
| 11,771,718 B2 | 10/2023 | Shah |
| 11,932,690 B2 | 3/2024 | Sadelain et al. |
| 2002/0132980 A1 | 9/2002 | Pestka |
| 2005/0079183 A1 | 4/2005 | Jordan et al. |
| 2005/0100543 A1 | 5/2005 | Hansen et al. |
| 2005/0175606 A1 | 8/2005 | Huang et al. |
| 2007/0014794 A1 | 1/2007 | Carter et al. |
| 2009/0028869 A1 | 1/2009 | Dodel et al. |
| 2009/0226474 A1 | 9/2009 | Weidanz et al. |
| 2010/0247549 A1 | 9/2010 | Goncalvez et al. |
| 2011/0081708 A1 | 4/2011 | Liu et al. |
| 2011/0142851 A1 | 6/2011 | Misher et al. |
| 2012/0183566 A1 | 7/2012 | Barfield et al. |
| 2014/0141067 A1 | 5/2014 | Bancel et al. |
| 2014/0227262 A1 | 8/2014 | Langermann |
| 2014/0244228 A1 | 8/2014 | Lee et al. |
| 2014/0271462 A1 | 9/2014 | Ho et al. |
| 2014/0349402 A1 | 11/2014 | Cooper et al. |
| 2015/0306141 A1 | 10/2015 | Jensen et al. |
| 2015/0368342 A1 | 12/2015 | Wu et al. |
| 2016/0207989 A1 | 7/2016 | Short |
| 2016/0297881 A1 | 10/2016 | Vu et al. |
| 2016/0370372 A1 | 12/2016 | Koomen |
| 2017/0029507 A1 | 2/2017 | Ho et al. |
| 2017/0044235 A1 | 2/2017 | Listek et al. |
| 2017/0051308 A1 | 2/2017 | Morgan et al. |
| 2017/0218337 A1 | 8/2017 | Friedman |
| 2017/0267756 A1 | 9/2017 | Riddell et al. |
| 2017/0306018 A1 | 10/2017 | Vu et al. |
| 2017/0306303 A1 | 10/2017 | Taunton et al. |
| 2017/0327597 A1 | 11/2017 | Labrijn et al. |
| 2017/0333480 A1 | 11/2017 | Cooper et al. |
| 2017/0334968 A1 | 11/2017 | Cooper et al. |
| 2017/0370906 A1 | 12/2017 | Darwish et al. |
| 2018/0000914 A1 | 1/2018 | Valton et al. |
| 2018/0002427 A1 | 1/2018 | Smith et al. |
| 2018/0002435 A1 | 1/2018 | Sasu et al. |
| 2018/0044399 A1 | 2/2018 | Rajpal et al. |
| 2018/0085402 A1 | 3/2018 | Kahvejian et al. |
| 2018/0100026 A1 | 4/2018 | Kim et al. |
| 2018/0104321 A1 | 4/2018 | Pule et al. |
| 2018/0133296 A1 | 5/2018 | Barrett et al. |
| 2018/0142210 A1 | 5/2018 | Delaney et al. |
| 2018/0147271 A1 | 5/2018 | Morgan et al. |
| 2018/0148508 A1 | 5/2018 | Wang et al. |
| 2018/0200298 A1* | 7/2018 | Jensen ............... A61P 11/00 |
| 2018/0237533 A1 | 8/2018 | Juillerat et al. |
| 2018/0305462 A1 | 10/2018 | Meng et al. |
| 2018/0353588 A1 | 12/2018 | Boyd et al. |
| 2018/0355318 A1 | 12/2018 | Delaney et al. |
| 2019/0032011 A1 | 1/2019 | Better et al. |
| 2019/0055299 A1 | 2/2019 | Thokala et al. |
| 2019/0062706 A1 | 2/2019 | Almaasbak et al. |
| 2019/0085063 A1 | 3/2019 | Frigault et al. |
| 2019/0092876 A1 | 3/2019 | Banham et al. |
| 2019/0106504 A1 | 4/2019 | Wu et al. |
| 2019/0153092 A1 | 5/2019 | Waldmeier et al. |
| 2019/0183932 A1 | 6/2019 | Mackall et al. |
| 2019/0194615 A1 | 6/2019 | Friedman |
| 2019/0263928 A1 | 8/2019 | Watanabe et al. |
| 2019/0276801 A1 | 9/2019 | Jensen |
| 2019/0277844 A1 | 9/2019 | Guo et al. |
| 2019/0292257 A1 | 9/2019 | Bedoya et al. |
| 2019/0300610 A1 | 10/2019 | Boyd-Kirkup et al. |
| 2019/0325989 A1 | 10/2019 | Lipowsky et al. |
| 2019/0338015 A1 | 11/2019 | Juillerat et al. |
| 2019/0350978 A1 | 11/2019 | Beauchesne et al. |
| 2020/0017588 A1 | 1/2020 | Marasco |
| 2020/0030379 A1 | 1/2020 | Pule et al. |
| 2020/0040058 A1 | 2/2020 | Hudecek et al. |
| 2020/0062812 A1 | 2/2020 | Bamdad et al. |
| 2020/0077644 A1 | 3/2020 | Church et al. |
| 2020/0095547 A1 | 3/2020 | Alizadeh et al. |
| 2020/0140560 A1 | 5/2020 | Duchateau et al. |
| 2020/0155597 A1 | 5/2020 | Crane et al. |
| 2020/0157174 A1 | 5/2020 | Chang et al. |
| 2020/0172879 A1 | 6/2020 | Suri et al. |
| 2020/0181573 A1 | 6/2020 | Rosen et al. |
| 2020/0181575 A1 | 6/2020 | Mujacic et al. |
| 2020/0215108 A1 | 7/2020 | Jensen |
| 2020/0239910 A1 | 7/2020 | Bonyhadi |
| 2020/0255803 A1 | 8/2020 | Zhang et al. |
| 2020/0338210 A1 | 10/2020 | Rosenberg |
| 2020/0354677 A1 | 11/2020 | Lee et al. |
| 2020/0384025 A1 | 12/2020 | Mujacic et al. |
| 2021/0087530 A1 | 3/2021 | Zynda et al. |
| 2021/0139579 A1 | 5/2021 | Grawunder et al. |
| 2021/0145882 A1 | 5/2021 | Maloney et al. |
| 2021/0155692 A1 | 5/2021 | Bailey et al. |
| 2021/0169880 A1 | 6/2021 | Hudecek et al. |
| 2021/0171909 A1 | 6/2021 | Golovina |
| 2021/0177902 A1 | 6/2021 | Shah et al. |
| 2021/0238549 A1 | 8/2021 | Chen et al. |
| 2021/0253729 A1 | 8/2021 | Ang et al. |
| 2021/0299223 A1 | 9/2021 | DiPersio et al. |
| 2021/0309717 A1 | 10/2021 | Moffett et al. |
| 2021/0317204 A1 | 10/2021 | McLean et al. |
| 2021/0332326 A1 | 10/2021 | Vodnala et al. |
| 2021/0380658 A1 | 12/2021 | Lajoie et al. |
| 2022/0041686 A1 | 2/2022 | Mackall et al. |
| 2022/0096651 A1 | 3/2022 | Costa et al. |
| 2022/0133901 A1 | 5/2022 | Lannutti et al. |
| 2022/0152214 A1 | 5/2022 | Miller et al. |
| 2022/0169694 A1 | 6/2022 | Bot et al. |
| 2022/0221463 A1 | 7/2022 | Bot et al. |

(56) References Cited

U.S. PATENT DOCUMENTS

| | | |
|---|---|---|
| 2022/0227866 A1 | 7/2022 | Watkins et al. |
| 2022/0249631 A1 | 8/2022 | Susarchick et al. |
| 2022/0306719 A1 | 9/2022 | Hudecek et al. |
| 2022/0307039 A1 | 9/2022 | Park et al. |
| 2022/0323598 A1 | 10/2022 | Takahashi |
| 2022/0348661 A1 | 11/2022 | He et al. |
| 2022/0356247 A1 | 11/2022 | Fan et al. |
| 2022/0401486 A1 | 12/2022 | Mackall et al. |
| 2023/0021388 A1 | 1/2023 | Watkins et al. |
| 2023/0070988 A1 | 3/2023 | Kaufmann |
| 2023/0203155 A1 | 6/2023 | McLean et al. |
| 2023/0293712 A1 | 9/2023 | Lannutti et al. |
| 2023/0310605 A1 | 10/2023 | Vodnala et al. |
| 2023/0312708 A1 | 10/2023 | Prussak et al. |
| 2023/0313138 A1 | 10/2023 | Vodnala et al. |
| 2023/0324408 A1 | 10/2023 | Hauskins et al. |
| 2024/0010721 A1 | 1/2024 | Wang et al. |
| 2024/0010753 A1 | 1/2024 | Gong et al. |
| 2024/0018237 A1 | 1/2024 | Tian et al. |
| 2024/0024476 A1 | 1/2024 | Pu et al. |
| 2024/0052029 A1 | 2/2024 | Zhou et al. |

FOREIGN PATENT DOCUMENTS

| | | | |
|---|---|---|---|
| EP | | 1956080 B1 | 9/2011 |
| EP | | 2872171 A1 | 5/2015 |
| EP | | 3134514 A1 | 3/2017 |
| EP | | 3200591 A1 | 8/2017 |
| EP | | 3338794 A1 | 6/2018 |
| EP | | 3006455 B1 | 7/2018 |
| EP | | 2496698 B1 | 1/2019 |
| EP | | 2814846 B1 | 1/2020 |
| EP | | 3129405 B1 | 2/2021 |
| EP | | 3851110 A1 | 7/2021 |
| WO | WO-2006020258 A2 | | 2/2006 |
| WO | WO-2007024715 A2 | | 3/2007 |
| WO | WO-2011056894 A2 | | 5/2011 |
| WO | WO-2012075158 A1 | | 6/2012 |
| WO | WO-2013092001 A1 | | 6/2013 |
| WO | WO-2013123061 A1 | | 8/2013 |
| WO | WO-2014031687 A1 | | 2/2014 |
| WO | WO-2015132604 A1 | | 9/2015 |
| WO | WO-2016123143 A1 | | 8/2016 |
| WO | WO-2016160618 A2 | | 10/2016 |
| WO | WO-2017117112 A1 | | 7/2017 |
| WO | WO-2017120997 A1 | | 7/2017 |
| WO | WO-2017120998 A1 | | 7/2017 |
| WO | WO-2017156479 A1 | | 9/2017 |
| WO | WO-2018006880 A1 | | 1/2018 |
| WO | WO-2018006881 A1 | | 1/2018 |
| WO | WO-2018064626 A1 | | 4/2018 |
| WO | WO-2018136570 A1 | | 7/2018 |
| WO | WO-2018137293 A1 | | 8/2018 |
| WO | WO-2018137294 A1 | | 8/2018 |
| WO | WO-2019010201 A1 | | 1/2019 |
| WO | WO-2019032927 A1 | | 2/2019 |
| WO | WO-2019070856 A1 | | 4/2019 |
| WO | WO-2019072824 A1 | | 4/2019 |
| WO | WO-2019113556 A1 | | 6/2019 |
| WO | WO-2019113557 A1 | | 6/2019 |
| WO | WO-2019118902 A2 | | 6/2019 |
| WO | WO-2019149743 A1 | | 8/2019 |
| WO | WO-2019152743 A1 | | 8/2019 |
| WO | WO-2019157298 A1 | | 8/2019 |
| WO | WO-2019162695 A1 | | 8/2019 |
| WO | WO-2019178078 A1 | | 9/2019 |
| WO | WO-2019183181 A1 | | 9/2019 |
| WO | WO-2019197676 A1 | | 10/2019 |
| WO | WO-2019213184 A1 | | 11/2019 |
| WO | WO-2019213308 A1 | | 11/2019 |
| WO | WO-2019223226 A1 | | 11/2019 |
| WO | WO-2019225992 A1 | | 11/2019 |
| WO | WO-2019241557 A1 | | 12/2019 |
| WO | WO-2020014366 A1 | | 1/2020 |
| WO | WO-2020018691 A1 | | 1/2020 |
| WO | WO-2020018964 A1 | | 1/2020 |
| WO | WO-2020028400 A1 | | 2/2020 |
| WO | WO-2020033272 A1 | | 2/2020 |
| WO | WO-2020037178 A1 | | 2/2020 |
| WO | WO-2020037181 A2 | | 2/2020 |
| WO | WO-2020047449 A2 | | 3/2020 |
| WO | WO-2020069508 A1 | | 4/2020 |
| WO | WO-2020070289 A1 | | 4/2020 |
| WO | WO-2020083282 A1 | | 4/2020 |
| WO | WO-2020088631 A1 | | 5/2020 |
| WO | WO-2020092440 A1 | | 5/2020 |
| WO | WO-2020187016 A1 | | 9/2020 |
| WO | WO-2020223625 A1 | | 11/2020 |
| WO | WO-2020247832 A1 | | 12/2020 |
| WO | WO-2020254591 A1 | | 12/2020 |
| WO | WO-2021048564 A2 | | 3/2021 |
| WO | WO-2021092097 A1 | | 5/2021 |
| WO | WO-2021101346 A1 | | 5/2021 |
| WO | WO-2021126841 A1 | | 6/2021 |
| WO | WO-2021173964 A1 | | 9/2021 |
| WO | WO-2021202863 A1 | | 10/2021 |
| WO | WO-2021219758 A1 | | 11/2021 |
| WO | WO-2021231655 A1 | | 11/2021 |
| WO | WO-2022098685 A2 | | 5/2022 |
| WO | WO-2022120160 A1 | | 6/2022 |
| WO | WO-2022129622 A1 | | 6/2022 |
| WO | WO-2021222479 A9 | | 8/2022 |
| WO | WO-2022165440 A2 | | 8/2022 |
| WO | WO-2022167460 A1 | | 8/2022 |
| WO | WO-2022174103 A2 | | 9/2022 |
| WO | WO-2022182890 A1 | | 9/2022 |
| WO | WO-2022182891 A1 | | 9/2022 |
| WO | WO-2022182915 A1 | | 9/2022 |
| WO | WO-2022204070 A1 | | 9/2022 |
| WO | WO-2022217048 A1 | | 10/2022 |
| WO | WO-2022217054 A1 | | 10/2022 |
| WO | WO-2023000791 A1 | | 1/2023 |
| WO | WO-2023125619 A1 | | 7/2023 |
| WO | WO-2023143315 A1 | | 8/2023 |

OTHER PUBLICATIONS

Baskar, S., et al., "Targeting malignant B cells with an immunotoxin against ROR1," MAbs. 4(3):349-361, Landes Bioscience, United States (May-Jun. 2012).

Baskar, S., et al., "Supplemental Material to: Targeting malignant B cells with an immunotoxin against ROR1," MAbs. 4(3), Landes Bioscience, United States (May-Jun. 2012).

Beltra, J.C., et al., "Developmental Relationships of Four Exhausted CD8+ T Cell Subsets Reveals Underlying Transcriptional and Epigenetic Landscape Control Mechanisms," Immunity 52(5):825-841.e8, Elsevier, Netherlands (May 2020).

Bird, R.E., et al., "Single-chain antigen-binding proteins," Science 242(4877):423-426, American Association for the Advancement of Science, United States (Oct. 1988).

Dobeli, H., et al., "Role of the carboxy-terminal sequence on the biological activity of human immune interferon (IFN-γ)," J Biotechnology 7:199-216, Elsevier, Netherlands (1988).

Geraci, F., et al., "Editorial: RNA-Seq Analysis: Methods, Applications and Challenges," Front Genet 11:220, Frontiers Media S.A., Switzerland (Mar. 2020).

Gayle, R.B., 3rd, et al. "Identification of regions in interleukin-1 alpha important for activity," J Biol Chem 268(29):22105-22111, The American Society for Biochemistry and Molecular Biology, United States (Oct. 1993).

Henry, C.E., et al., "ROR1 and ROR2 play distinct and opposing roles in endometrial cancer," Gynecol Oncol 148(3):576-584, Elsevier, Netherlands (Mar. 2018).

Hojjat-Farsangi, M., "Inhibition of the receptor tyrosine kinase ROR1 by anti-ROR1 monoclonal antibodies and siRNA induced apoptosis of melanoma cells," PLoS One 8(4):e61167, Public Library of Science, United States (Apr. 2013).

Holliger, P., and Hudson, P.J., "Engineered antibody fragments and the rise of single domains," Nat Biotechnol 23(9):1126-1136, Nature Publishing Group, United Kingdom (Sep. 2005).

(56) References Cited

OTHER PUBLICATIONS

Holliger, P., et al., "'Diabodies': Small bivalent and bispecific antibody fragments," Proc Natl Acad Sci USA 90:6444-6448, National Academy of Science, United States (Jul. 1993).

Hudecek, M., et al., "Receptor affinity and extracellular domain modifications affect tumor recognition by ROR1-specific chimeric antigen receptor T cells," Clin Cancer Res 19(12):3153-3164, American Association for Cancer Research (Jun. 2013).

Huston, J.S., et al., "Protein engineering of antibody binding sites: recovery of specific activity in an anti-digoxin single-chain Fv analogue produced in *Escherichia coli*," Proc Natl Acad Sci USA 85(16):5879-5883, National Academy of Science, United States (Aug. 1988).

Kabadi, A.M., and Gersbach, C.A., "Engineering synthetic TALE and CRISPR/Cas9 transcription factors for regulating gene expression," Methods 69(2):188-197, Elsevier, Netherlands (Sep. 2014).

Kim, J.H., et al., "High cleavage efficiency of a 2A peptide derived from porcine teschovirus-1 in human cell lines, zebrafish and mice," PLoS One 6(4):e18556, Public Library of Science, United States (2011).

Koh, E.Y., et al., Ho SC, "An internal ribosome entry site (IRES) mutant library for tuning expression level of multiple genes in mammalian cells," PLoS One. 8(12):e82100, Public Library of Science, United States (Dec. 2013).

Lafleur, M.W., et al., "Prevention of CAR-T-cell dysfunction," Nat Biomed Eng 4(1):16-17, Nature Portfolio, Germany (Jan. 2020).

Martinez, M., and Moon, E.K., "CAR T Cells for Solid Tumors: New Strategies for Finding, Infiltrating, and Surviving in the Tumor Microenvironment," Front Immunol 10:128, Frontiers Research Foundation, Switzerland (Feb. 2019).

Mei, B., et al., "Rational design of a fully active, long-acting PEGylated factor VIII for hemophilia A treatment," Blood 116(2):270-279, The American Society of Hematology, United States (Jul. 2010).

Milone, M.C., et al., "Chimeric receptors containing CD137 signal transduction domains mediate enhanced survival of T cells and increased antileukemic efficacy in vivo," Mol Ther. 17(8):1453-1464, Cell Press, United States (Aug. 2009).

Milone, M.C., et al., "Table S1: Treatment Groups," Mol Ther 17(8), Cell Press, United States (Aug. 2009).

Milone, M.C., et al., "Supplemental Table S2. Primer sequences used for construction of the different CARs using the splicing by overlap extension technique," Mol Ther 17(8), Cell Press, United States (Aug. 2009).

Milone, M.C., et al., "Supplemental Table S3. In vivo comparison of αCD19-BB-ζ and αCD19-α persistence in spleens from day 35 to day 198 post injection," Mol Ther 17(8), Cell Press, United States (Aug. 2009).

Newick, K., et al., "Chimeric antigen receptor T-cell therapy for solid tumors," Mol Ther Oncolytics 3:16006, American Society of Gene & Cell Therapy, United States (Apr. 2016).

Nissim, L., et al., "Multiplexed and programmable regulation of gene networks with an integrated RNA and CRISPR/Cas toolkit in human cells," Mol Cell 54(4):698-710, Cell Press, United States (May 2014).

Nissim, L., et al., "Article and Supplemental Information: Multiplexed and programmable regulation of gene networks with an integrated RNA/CRISPR/Cas toolkit in human cells," Mol Cell 54(4):698-710, Cell Press, United States (May 2014).

Nissim, L., et al., "Supplemental Information: Multiplexed and programmable regulation of gene networks with an integrated RNA and CRISPR/Cas toolkit in human cells," Mol Cell 54(4), Cell Press, United States (May 2014).

Nissim, L., et al., "Table S2. Select sequences use," Mol Cell 54(4), Cell Press, United States (May 2014).

Pandelakis, M., et al., "CRISPR-Based Synthetic Transcription Factors In Vivo: The Future of Therapeutic Cellular Programming," Cell Syst 10(1):1-14, Cell Press, United States (Jan. 2020).

Ron, D., et al., "Expression of biologically active recombinant keratinocyte growth factor. Structure/function analysis of amino-terminal truncation mutants," J Biol Chem 268(4):2984-2988, American Society for Biochemistry and Molecular Biology, United States (Feb. 1993).

Specht, J., "ROR1 CAR-T cell therapy in CLL and Solid Tumors," EHA-EBMT $2^{nd}$ CAR T Cell Meeting Jan. 30-Feb. 1, 2020, pp. 1-26, Spain (Jan. 2020).

Srivastava, S., and Riddell, S.R., "Chimeric Antigen Receptor T Cell Therapy: Challenges to Bench-to-Bedside Efficacy," J Immunol 200(2):459-468, American Association of Immunologists, United States (Jan. 2018).

Sturm, G., et al., "Comprehensive evaluation of transcriptome-based cell-type quantification methods for immuno-oncology," Bioinformatics 35(14):1436-i445, Oxford University Press, United Kingdom (Jul. 2019).

Sturm, G., et al., "4a Controlled Vocabulary," Bioinformatics 35(14), Oxford University Press, United Kingdom (Jul. 2019).

Sturm, G., et al., "4b Mapping," Bioinformatics 35(14), Oxford University Press, United Kingdom (Jul. 2019).

Sturm, G., et al., "Accession," Bioinformatics 35(14), Oxford University Press, United Kingdom (Jul. 2019).

Sturm, G., et al., "BioQC Excel Sheet 1," Bioinformatics 35(14), Oxford University Press, United Kingdom (Jul. 2019).

Sturm, G., et al., "BioQC Excel Sheet 2," Bioinformatics 35(14), Oxford University Press, United Kingdom (Jul. 2019).

Sturm, G., et al., "Supplementary Figures," Bioinformatics 35(14), Oxford University Press, United Kingdom (Jul. 2019).

Sturm, G., et al., "Supplementary Table 2," Bioinformatics 35(14), Oxford University Press, United Kingdom (Jul. 2019).

Van Den Berge, K., et al., "RNA Sequencing Data: Hitchhiker's Guide to Expression Analysis," Annual Review of Biomed Data Sci 2:139-173, Annual Reviews, United States (Apr. 2019).

Xiao, B.F., et al., "Chimeric Antigen Receptor T-Cell Therapy in Lung Cancer: Potential and Challenges," Front Immunol 12:782775, Frontiers Research Foundation, Switzerland (Nov. 2021).

Xu, G.L., et al., "ROR1 is highly expressed in circulating tumor cells and promotes invasion of pancreatic cancer," Mol Med Rep 18(6):5087-5094, Spandidos Publications, Greece (Dec. 2018).

Yang, J., et al., "Therapeutic potential and challenges of targeting receptor tyrosine kinase ROR1 with monoclonal antibodies in B-cell malignancies," PLoS One 6(6):e21018, Public Library of Science, United States (Jun. 2011).

Yang, Z., et al., "Context-Dependent Reversible Modulation of cJUN Expression by Car T Cells for Cancer Treatment," J Immunother Cancer 9(Suppl 2):A154, BMJ, United Kingdom (Nov. 2021).

Yang, Z., et al., "Contextual reprogramming of CAR-T cells for treatment of HER2+ cancers," J Transl Med 19:459, BioMed Central, United Kingdom (2021).

Yang, Z., et al., "Figure S1, related to Figure 1," J Transl Med 19, BioMed Central, United Kingdom (2021).

Zhang, L., et al., "Lineage tracking reveals dynamic relationships of T cells in colorectal cancer," Nature 564(7735):268-272, Springer Nature, Germany (Dec. 2018).

Zhou, J.K., et al., "ROR1 expression as a biomarker for predicting prognosis in patients with colorectal cancer," Oncotarget 8(20):32864-32872, Impact Journals, United States (May 2017).

Brennan, A., et al., "Selective Antagonism of cJUN for Cancer Therapy," Journal of Experimental & Clinical Cancer Research 39(1):184, BioMed Central, United Kingdom (Sep. 2020).

Bridgeman, J.S., et al., "The Optimal Antigen response of Chimeric Antigen Receptors harboring the CD3zeta transmembrane domain is dependent upon incorporation of the receptor into the endogenous TCR/CD3 complex," Journal of Immunology 184(12):6938-49, American Association of Immunologists, United States (Jun. 2010).

Chen, K., et al., "New insights into the enigma of immunoglobulin D," Immunol Rev 237(1):160-179, Wiley Online Library, United States (Sep. 2010).

Dard, P., et al., "The IGHG3 gene shows a structural polymorphism characterized by different hinge lengths: sequence of a new 2-exon hinge gene," Hum Genet 99(1):138-41, Springer-Link, Germany (Jan. 1997).

Davila, M.L., et al., "CD19 CAR-targeted T Cells Induce Long-term Remission and B Cell Aplasia in an Immunocompetent Mouse

(56) References Cited

OTHER PUBLICATIONS

Model of B Cell Acute Lymphoblastic Leukemia," PLoS one 8(4):e61338, 1-14, Public Library of Science, United States (Apr. 2013).
Ferguson, K.M., "Structure-based View of Epidermal Growth Factor Receptor Regulation," Annual Review of Biophysics 37:353-373, Annual Reviews, United States (2008).
Freshney, R.I., "Quantitation and Experimental Design" in *Culture of Animal Cells: A Manual of Basic Technique*, Second Edition, pp. 1-36, Alan R. Liss, Inc., New York, United States (1987).
Gait, M. J., "Oligonucleotide Synthesis: A Practical Approach," Practical Approach Series, p. 217, IRL Press, United Kingdom (1984).
Giuntini, S., et al., "Human IgG1, IgG3, and IgG3 Hinge-Truncated Mutants Show Different Protection Capabilities against Meningococci Depending on the Target Antigen and Epitope Specificity," Clin Vaccin Immunol 23(8):698-706, American Society for Microbiology, United States (Aug. 2016).
Hames, B.D. and Higgins, S.J., "Transcription and Translation: A Practical Approach," p. 328, IRL Press, United States (1984).
Hedger, G., et al., "The Juxtamembrane Regions of Human Receptor Tyrosine Kinases Exhibit Conserved Interaction Sites With Anionic Lipids," Scientific Reports 5:9198, Nature Publishing Group, United Kingdom (Mar. 2015).
Huck, S., et al., "Sequence of a human immunoglobulin gamma 3 heavy chain constant region gene: comparison with the other human C gamma genes," Nucleic Acids Res 14(4):1779-1789, Oxford Academic, United Kingdom (Feb. 1986).
International Search Report and Written Opinion for International Application No. PCT/US2021/032098, mailed Nov. 2, 2021, 27 pages.
James, S.E., et al., "Antigen sensitivity of CD22-specific chimeric TCR is modulated by target epitope distance from the cell membrane," Journal of Immunology 180(10):7028-7038, Williams & Wilkins, United States (May 2008).
Jefferis, R., and Lefranc, M.P., "Human Immunoglobulin Allotypes: Possible Implications for Immunogenicity," Mabs 1(4):332-338, Taylor & Francis, United States (Jul.-Aug. 2009).
Juo, P.S., "The Concise Dictionary of Biomedicine and Molecular Biology," 2nd Edition, CRC Press, United States (2002), 4 pages.
Klein, J.S., et al., "Design and characterization of structured protein linkers with differing flexibilities," Protein Eng Des Set 27(10):325-330, Oxford Academic, United Kingdom (Oct. 2014).
Klement, M., et al., "Effect of Linker Flexibility and Length on the Functionality of a Cytotoxic Engineered Antibody Fragment," Journal of Biotechnology 199:90-97, Elsevier Science Publishers, Netherlands (Apr. 2015).
Kovacs, E., et al., "A Structural Perspective on the Regulation of the Epidermal Growth Factor Receptor," Annual Review of Biochemistry 84:739-764, Annual Reviews, United States (Jan. 2015).
Kudla, G., et al., "High Guanine and Cytosine Content Increases mRNA Levels in Mammalian Cells," PLoS Biology 4(6):e180, Public Library of Science, United States (Jun. 2006).
Lackie, J.M. and Dow, J.A.T., "The Dictionary of Cell and Molecular Biology," 3rd Edition, Academic Press, United States (1999), 2 pages.
Leppa, S., and Bohmann, D., "Diverse functions of JNK signaling and c-Jun in stress response and apoptosis," Oncogene 18(45):6158-6162, Nature Publishing Group, United Kingdom (Nov. 1999).
Li, S., et al., "Structural basis for inhibition of the epidermal growth factor receptor by cetuximab," Cancer Cell 7(4):301-311, Elsevier, United States (Apr. 2005).
Liu, L., et al., "Inclusion of Strep-tag II in design of antigen receptors for T-cell immunotherapy," Nature Biotechnology 34(4):430-434, Nature Publishing Group, United Kingdom (Apr. 2016). (With Supplemental Figures). 14 pages.
Liu, Z., et al., "Systematic Comparison of 2A Peptides for Cloning Multi-genes in a Polycistronic Vector," Scientific Reports 7(1):2193, Nature Publishing Group, United Kingdom (May 2017).
*Manipulating the Mouse Embryo: A Laboratory Manual*, Behringer, R., ed., pp. 1-22, Cold Spring Harbor Laboratory Press, Cold Spring Harbor, United States (1986).
Mayer, R.J. and Walker, J.H., "Immunochemical Methods in Cell and Molecular Biology," p. 325, Academic Press, United Kingdom (1987).
McLaughlin, S., et al., "An Electrostatic Engine Model for Autoinhibition and Activation of the Epidermal Growth Factor Receptor (EGFR/ErbB) Family," The Journal of General Physiology 126(1):41-53, Rockefeller University Press, United States (Jul. 2005).
Michaelsen, T.E., et al., "Primary structure of the "hinge" region of human IgG3. Probable quadruplication of a 15-amino acid residue basic unit," J Biol Chem 252(3); 883-889, Elsevier, Netherlands (Feb. 1977).
Miller, J.H. and Calos, M.P., "Gene Transfer Vectors For Mammalian Cells," Current Communications in Molecular Biology, Cold Spring Harbor Laboratory, United States (1987).
NCT02222688, "UC-961 (Cirmtuzumab) in Relapsed or Refractory Chronic Lymphocytic Leukemia," retrieved from: https://clinicaltrials.gov/ct2/show/NCT02222688, last accessed Aug. 26, 2021, 10 pages.
Paszkiewicz, P.J., et al., "Targeted Antibody-mediated Depletion of Murine CD19 CAR T Cells Permanently Reverses B Cell Aplasia" The Journal of Clinical Investigation 126(11):4262-4272, American Society for Clinical Investigation, United States (Nov. 2016).
Pietrobon, V., et al., "Improving CAR T-Cell Persistence," International Journal of Molecular Sciences 22(19):10828, 27 Pages, MDPI, Switzerland (Oct. 2021).
Plomp, R., et al., "Hinge-Region O-Glycosylation of Human Immunoglobulin G3 (IgG3)*," Mol Cell Proteomics. 14(5):1373-1384, American Society for Biochemistry and Molecular Biology, United States (May 2015).
Rogers, K.A., et al., "Molecular characterization of immunoglobulin D in mammals: immunoglobulin heavy constant delta genes in dogs, chimpanzees and four old world monkey species," Immunology 118(1):88-100, Blackwell Publishing, United States (May 2006).
Roux, K.H., et al., "Flexibility of human IgG subclasses," Journal of Immunology 159(7):3372-3382, American Association of Immunologists, United States (Oct. 1997).
Sambrook, J., et al., "Molecular Cloning: A Laboratory Manual," Second Edition, Cold Spring Harbor Laboratory Press, United States (1989).
Sengupta, P., et al., "EGFR Juxtamembrane Domain, Membranes, and Calmodulin: Kinetics of Their Interaction," Biophysical Journal 96(12):4887-4895, Cell Press, United States (Jun. 2009).
Sharp, P.M. and Li, W.H., "The Codon Adaptation Index-a Measure of Directional Synonymous Codon Usage Bias, and Its Potential Applications," Nucleic Acids Research 15(3):1281-1295, Oxford University Press, United Kingdom (Feb. 1987).
The Oxford Dictionary of Biochemistry and Molecular Biology, Revised Edition, Oxford University Press, United Kingdom, 2 pages (2000).
Vidarsson, G., et al., "IgG Subclasses and Allotypes: from Structure to Effector Functions," Frontiers in Immunology 5(Article 520): 17 pages, Lausanne: Frontiers Research Foundation, Switzerland (Oct. 2014).
Woodward, J., "Immobilized Cells and Enzymes—A Practical Approach," p. 177, IRL Press, United Kingdom (1986).
Zhao, S., et al., "Piggybac Transposon Vectors: the Tools of the human gene encoding," Translational Lung Cancer Research 5(1):120-125, Pioneer Bioscience Publishing Company, China (Feb. 2016).

* cited by examiner

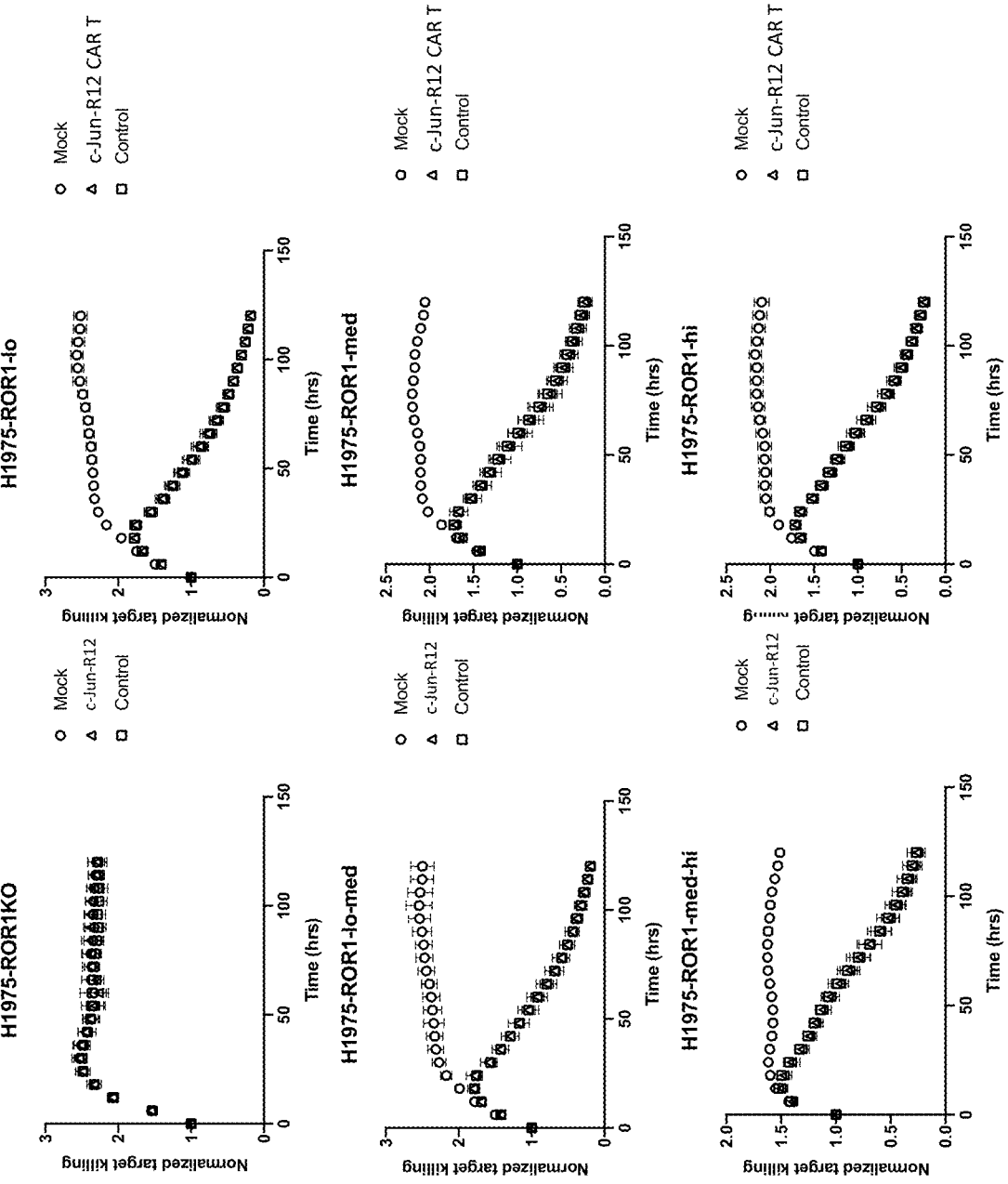

ROR1 TARGETING CHIMERIC ANTIGEN RECEPTOR

CROSS-REFERENCE TO RELATED APPLICATION

This application claims the priority benefit of U.S. Provisional Application No. 63/153,878, filed on Feb. 25, 2021; 63/263,229, filed on Oct. 28, 2021; and 63/309,393, filed on Feb. 11, 2022; each of which is herein incorporated by reference in its entirety.

REFERENCE TO SEQUENCE LISTING SUBMITTED ELECTRONICALLY VIA EFS-WEB

The content of the electronically submitted sequence listing (Name: 4385_0420005_Seqlisting_ST25.txt, Size: 80,724 bytes; and Date of Creation: Feb. 24, 2022) submitted in this application is incorporated herein by reference in its entirety.

BACKGROUND OF THE DISCLOSURE

Adoptive immunotherapy using chimeric antigen receptor (CAR) expressing T cells is a promising cancer treatment, because these cells can directly recognize and kill antigen-expressing tumor cells in a human leukocyte antigen (HLA)-independent manner. However, T cell exhaustion is a major factor limiting the efficacy of CAR T cell therapeutics.

Accordingly, there is a need for methodologies that provide exhaustion-resistant CAR T cells to allow for maximum efficacy.

BRIEF SUMMARY OF THE DISCLOSURE

In some aspects, the present disclosure provides a polynucleotide encoding a chimeric polypeptide comprising a c-Jun polypeptide (c-jun), a ROR1-binding protein, and a truncated EGF receptor (EGFRt). In some aspects, the c-Jun polypeptide comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 1. In some aspects, the c-Jun polypeptide is capable of preventing or reducing exhaustion of a cell when the chimeric polypeptide is expressed in the cell. In some aspects, the ROR1-binding protein comprises a chimeric antigen receptor (CAR) or a T cell receptor (TCR) that specifically binds to ROR1. In some aspects, the CAR comprises an antibody or antigen binding portion thereof that specifically binds to ROR1. In some aspects, the ROR1-binding protein specifically binds to the same epitope as the R12 antibody. In some aspects, the ROR1-binding protein comprises a heavy chain variable region (VH) comprising CDR1, CDR2, and CDR3 of the R12 antibody and a light chain variable region (VL) comprising CDR1, CDR2, and CDR3 of the R12 antibody. In some aspects, the VH CDR1 comprises SEQ ID NO: 45, VH CDR2 comprises SEQ ID NO: 46, and VH CDR3 comprises SEQ ID NO: 47. In some aspects, the VL CDR1 comprises SEQ ID NO: 49, VL CDR2 comprises SEQ ID NO: 50, and VL CDR3 comprises SEQ ID NO: 51. In some aspects, the VH of the ROR1 binding portion comprises SEQ ID NO: 44 and the VL of the ROR1 binding portion comprises SEQ ID NO: 48. In some aspects, the ROR1 binding portion comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 52. In some aspects, the CAR further comprises a transmembrane (TM) domain. In some aspects, the TM domain is derived from CD8a, CD2, CD4, CD28, CD45, PD1, CD152, or any combination thereof. In some aspects, the TM domain is derived from CD28. In some aspects, the TM domain comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 54

In some aspects, the polynucleotide encoding a CAR of the present disclosure further comprises a spacer between the antibody or antigen binding portion thereof that specifically binds to ROR1 and the TM domain. In some aspects, the spacer is derived from an immunoglobulin hinge region or CD8. In some aspects, the spacer comprises an amino acid sequence as set forth in SEQ ID NO: 15. In some aspects, the spacer further comprises a linker. In some aspects, the linker comprises GGGSG (SEQ ID NO: 16). In some aspects, the CAR further comprises an intracellular signaling domain. In some aspects, wherein the intracellular signaling domain comprises a CD3ζ activating domain, a CD3δ activating domain, a CD3ε activating domain, a CD3η activating domain, a CD79A activating domain, a DAP 12 activating domain, a FCER1G activating domain, a DAP10/CD28 activating domain, a ZAP70 activating domain, or any combination thereof. In some aspects, the intracellular signaling domain comprises a CD3ζ activating domain. In some aspects, the CD3ζ activating domain comprises an amino acid sequence having at least about 70%, at least about 75%, at least about 80%, at least about 85%, at least about 90%, at least about 95%, at least about 96%, at least about 97%, at least about 98%, at least about 99%, or at least about 100% sequence identity to SEQ ID NO: 55. In some aspects, the CAR comprises an intracellular co-stimulatory signaling region. In some aspects, the intracellular co-stimulatory signaling domains comprises a costimulatory domain of interleukin-2 receptor (IL-2R), interleukin-12 receptor (IL-12R), IL-7, IL-21, IL-23, IL-15, CD2, CD3, CD4, CD7, CD8, CD27, CD28, CD30, CD40, 4-1BB/CD137, ICOS, lymphocyte function-associated antigen-1 (LFA-1), LIGHT, NKG2C, OX40, DAP10, B7-H$_3$, CD28 deleted for Lck binding (ICA), OX40, BTLA, GITR, HVEM, LFA-1, LIGHT, NKG2C, PD-1, TLR2, TLR4, TLR7, TLR9, Fc receptor gamma chain, Fc receptor c chain, a ligand that specifically binds with CD83, or any combination thereof. In some aspects, the intracellular signaling domain comprises a 4-1BB co-stimulatory domain. In some aspects, the 4-1BB co-stimulatory domain comprises an amino acid sequence having at least about 70%, at least about 75%, at least about 80%, at least about 85%, at least about 90%, at least about 95%, at least about 96%, at least about 97%, at least about 98%, at least about 99%, or at least about 100% sequence identity to SEQ ID NO: 53.

In some aspects, the present disclosure provides a polynucleotide comprising a nucleotide sequence encoding a chimeric antigen receptor comprising (i) an ROR1-binding protein, (ii) a spacer comprising the amino acid sequence as set forth in SEQ ID NO: 15, (iii) a CD28 transmembrane protein, (iv) a 4-1BB co-stimulatory region, and (v) a CD3 ζ activating domain.

In some aspects, provided herein is a polynucleotide comprising a nucleotide sequence encoding a chimeric antigen receptor (CAR) comprising (i) a ROR1-binding protein comprising a heavy chain variable region (VH) comprising CDR1, CDR2, and CDR3 of the R12 antibody and a light chain variable region (VL) comprising CDR1, CDR2, and CDR3 of the R12 antibody; (ii) a spacer comprising the amino acid sequence as set forth in SEQ ID NO: 15; and (iii) a nucleotide sequence encoding a truncated EGF receptor (EGFRt). In some aspects, the VH of the ROR1 binding portion comprises SEQ ID NO: 44 and the VL of the ROR1 binding portion comprises SEQ ID NO: 48. In some aspects, the EGFRt comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 3.

In some aspects, the polynucleotide described herein further comprises a nucleotide sequence encoding a c-Jun polypeptide. In some aspects, the nucleotide sequence encoding a c-jun polypeptide and the nucleotide sequence encoding the CAR are on the same vector. In some aspects, the c-jun polypeptide and the CAR are linked by a linker. In some aspects, the linker is a cleavable linker. In some aspects, the linker comprises a P2A linker, a T2A linker, or any combination thereof. In some aspects, the nucleotide sequence encoding a c-jun polypeptide and the nucleotide sequence encoding the CAR are on different vectors.

In some aspects, the polynucleotide further comprises a nucleotide sequence encoding a truncated EGF receptor (EGFRt). In some aspects, the nucleotide sequence encoding a truncated EGF receptor (EGFRt) and the nucleotide sequence encoding the CAR are on the same vector. In some aspects, the EGFRt and the CAR are linked by a linker. In some aspects, the linker is a cleavable linker. In some aspects, the linker comprises a P2A linker, a T2A linker, or any combination thereof. In some aspects, the CAR further comprises a signal peptide. In some aspects, the signal peptide is derived from hIgK. In some aspects, the hIgK signal peptide comprises an amino acid sequence set forth as SEQ ID NO: 17. In some aspects, the EGFRt comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 3.

In some aspects, the polynucleotides disclosed herein further comprise a myeloproliferative sarcoma virus enhancer, negative control region deleted, dl587rev primer-binding site substituted (MND) promoter, EF1a promoter, and/or ubiquitin promoter. In some aspects, the MND promoter comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 64.

In some aspects, the polynucleotide comprises a nucleotide sequence encoding an amino acid sequence having at least about 60%, at least about 65%, at least about 70%, at least about 75%, at least about 80%, at least about 85%, at least about 90%, at least about 95%, at least about 96%, at least about 97%, at least about 98%, at least about 99% or about 100% sequence identity to SEQ ID NO: 58.

In some aspects, the present disclosure provides a polynucleotide encoding a CAR comprising a nucleotide sequence encoding an amino acid sequence having at least about 90%, at least about 95%, at least about 96%, at least about 97%, at least about 98%, at least about 99% or about 100% sequence identity to SEQ ID NO: 57.

In some aspects, the present disclosure provides a vector comprising the polynucleotide disclosed herein. In some aspects, the present disclosure provides a polypeptide encoded by the polynucleotide or the vector disclosed herein.

In some aspects, the present disclosure provides a chimeric antigen receptor (CAR) polypeptide comprising (i) an ROR1-binding antibody or antigen binding portion thereof, (ii) a spacer comprising the amino acid sequence as set forth in SEQ ID NO: 15, (iii) a CD28 transmembrane protein, (iv) a 4-1BB co-stimulatory region, and (v) a CD3 ζ activating domain. In some aspects, the ROR1-binding antibody or antigen binding portion thereof specifically binds to the same epitope as the R12 antibody. In some aspects, the ROR1-binding antibody or antigen binding portion thereof comprises a heavy chain variable region (VH) comprising CDR1, CDR2, and CDR3 of the R12 antibody and a light chain variable region (VL) comprising CDR1, CDR2, and CDR3 of the R12 antibody. In some aspects, the VH CDR1 comprises SEQ ID NO: 45, VH CDR2 comprises SEQ ID NO: 46, and VH CDR3 comprises SEQ ID NO: 47. In some aspects, the VL CDR1 comprises SEQ ID NO: 49, VL CDR2 comprises SEQ ID NO: 50, and VL CDR3 comprises SEQ ID NO: 51. In some aspects, the VH of the ROR1-binding antibody or antigen binding portion thereof comprises SEQ ID NO: 44 and the VL of the ROR1 binding portion comprises SEQ ID NO: 48. In some aspects, the ROR1-binding antibody or antigen binding portion thereof comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 52.

In some aspects, the polypeptide further comprises a transmembrane (TM) domain. In some aspects, the CD28 TM domain comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 54. In some aspects, the CD3 ζ activating domain comprises an amino acid sequence having at least about 70%, at least about 75%, at least about 80%, at least about 85%, at least about 90%, at least about 95%, at least about 96%, at least about 97%, at least about 98%, at least about 99%, or at least about 100% sequence identity to SEQ ID NO: 55. In some aspects, the 4-1BB co-stimulatory domain comprises an amino acid sequence having at least about 70%, at least about 75%, at least about 80%, at least about 85%, at least about 90%, at least about 95%, at least about 96%, at least about 97%, at least about 98%, at least about 99%, or at least about 100% sequence identity to SEQ ID NO: 53.

In some aspects, the present disclosure provides a chimeric polypeptide comprising a c-Jun polypeptide (c-jun), a CAR polypeptide, and a truncated EGF receptor (EGFRt). In some aspects, the CAR polypeptide is any disclosed herein. In some aspects, the c-Jun polypeptide comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 1. In some aspects, the c-Jun polypeptide is capable of preventing or reducing exhaustion of a cell when the chimeric polypeptide is expressed in the cell. In some aspects, wherein the c-jun polypeptide and the CAR polypeptide are on the same vector. In some aspects, the c-jun polypeptide and the CAR polypeptide are linked by a linker.

In some aspects, the linker is a cleavable linker. In some aspects, the linker comprises a P2A linker, a T2A linker, or any combination thereof. In some aspects, the c-jun polypeptide and the CAR polypeptide are on different vectors. In some aspects, the truncated EGF receptor (EGFRt) and the CAR are on the same vector. In some aspects, the EGFRt and the CAR are linked by a linker. In some aspects, the linker is a cleavable linker. In some aspects, the linker comprises a P2A linker, a T2A linker, or any combination thereof. In some aspects, the EGFRt comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 3. In some aspects, the chimeric polypeptide comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 52.

In some aspects, the present disclosure provides a chimeric polypeptide comprising an amino acid sequence having at least about 90%, at least about 95%, at least about 96%, at least about 97%, at least about 98%, at least about 99%, or about 100% sequence identity to SEQ ID NO: 52. In some aspects, the CAR polypeptide further comprises a signal peptide. In some aspects, the signal peptide is derived from hIgK. In some aspects, the hIgK signal peptide comprises an amino acid sequence set forth as SEQ ID NO: 17.

In some aspects, the present disclosure provides a modified cell comprising the polynucleotides, vectors, polypeptides, chimeric polypeptides, or any combination thereof.

In some aspects, the present disclosure provides a modified cell comprising a c-jun polypeptide, a chimeric antigen receptor polypeptide, and a truncated EGF receptor (EGFRt). In some aspects, the modified cell comprises the polypeptides disclosed herein. In some aspects, the modified cell comprises a CAR polypeptide and EGFRt are expressed on the cell surface. In some aspects, the cell is an immune cell. In some aspects, the cell is a T cell, a B cell, a regulatory T cell (Treg), a tumor infiltrating lymphocyte (TIL), a natural killer (NK) cell, a natural killer T (NKT) cell, a stem cell, an induced pluripotent stem cell, and any combination thereof. In some aspects, the cell is engineered in vitro or ex vivo. In some aspects, the cell is cultured in vitro or ex vivo.

In any of the modified cells described above, in some aspects, the expression of the c-Jun polypeptide is increased compared to a corresponding cell which has not been modified to comprise any of the polynucleotides, vectors, polypeptides, and/or chimeric polypeptides of the present disclosure. In some aspects, compared to the corresponding cell, the expression of the c-Jun polypeptide is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more.

Also provided herein is a population of immune cells which comprise a c-Jun polypeptide, a chimeric antigen receptor (CAR) polypeptide, and a truncated EGF receptor (EGFRt), wherein the population comprises a reduced number of TIGIT-positive immune cells after an antigen stimulation, as compared to a reference population of corresponding cells which do not comprise the c-Jun polypeptide.

In some aspects, the number of TIGIT-positive immune cells present in the population after the antigen stimulation is reduced by at least about 30%, at least about 35%, at least about 40%, at least about 45%, at least about 50%, at least about 55%, or at least about 60%, compared to the reference population. In some aspects, the population of immune cells comprises less than about 15%, less than about 14%, less than about 13%, less than about 12%, less than about 11%, less than about 10%, less than about 9%, less than about 8%, less than about 7%, less than about 6%, or less than about 5% of TIGIT-positive immune cells after the antigen stimulation.

In some aspects, the present disclosure further provides a population of immune cells which comprise a c-Jun polypeptide, a chimeric antigen receptor (CAR) polypeptide, and a truncated EGF receptor (EGFRt), wherein the population comprises a reduced number of TNFRSF9-positive immune cells after an antigen stimulation, as compared to a reference population of corresponding cells which do not comprise the c-Jun polypeptide.

In some aspects, the number of TNFRSF9-positive immune cells present in the population after the antigen stimulation is reduced by at least about 40%, at least about 45%, at least about 50%, at least about 55%, at least about 60%, at least about 65%, or at least about 70%, compared to the reference population. In some aspects, the population of immune cells comprises less than about 5%, less than about 4.5%, less than about 4%, less than about 3.5%, or less than about 2% of TNFRSF9-positive immune cells after the antigen stimulation.

Also provided herein is a population of immune cells which comprise a c-Jun polypeptide, a chimeric antigen receptor (CAR) polypeptide, and a truncated EGF receptor (EGFRt), wherein the population comprises a reduced number of GZMA-positive immune cells after an antigen stimulation, as compared to a reference population of corresponding cells which do not comprise the c-Jun polypeptide.

In some aspects, the number of GZMA-positive immune cells present in the population after the antigen stimulation is reduced by at least about 40%, at least about 35%, at least about 30%, at least about 25%, or at least about 20%, compared to the reference population. In some aspects, the population of immune cells comprises less than about 30%, less than about 25%, less than about 20%, less than about 15%, or less than about 10% of GZMA-positive immune cells after the antigen stimulation.

In any of the population of immune cells described above, in some aspects, the CAR polypeptide comprises any of the CAR polypeptides described herein. In some aspects, the c-Jun polypeptide comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 1. In some aspects, the EGFRt comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 3.

In any of the population of immune cells provided above, in some aspects, the immune cells comprise T cells, B cells, regulatory T cells (Tregs), tumor infiltrating lymphocytes (TILs), natural killer (NK) cells, natural killer T (NKT) cells, stem cells, induced pluripotent stem cells, or a combination thereof. In some aspects, the immune cells are T cells (e.g., CD4+ T cells, CD8+ T cells, or both).

In some aspects, the present disclosure provides a pharmaceutical composition comprising the polynucleotide, the vector, the polypeptide, the chimeric polypeptide or the modified cell disclosed herein and a pharmaceutically acceptable carrier.

In some aspects, the present disclosure provides a method of preparing a cell expressing a chimeric antigen receptor comprising transfecting a cell with the polynucleotides or vectors disclosed herein. In some aspects, the present disclosure provides a method of preparing a cell expressing a chimeric antigen receptor comprising expressing the polypeptides or the chimeric polypeptides disclosed herein in a cell. In some aspects, the cell comprises a T cell, a B cell, a regulatory T cell (Treg), a tumor infiltrating lymphocyte (TIL), a natural killer (NK) cell, a natural killer T (NKT) cell, a stem cell, an induced pluripotent stem cell, and any combination thereof. In some aspects, the cell is cultured in vitro or ex vivo.

In some aspects, the present disclosure provides a method of expanding a cell expressing a chimeric antigen receptor comprising culturing a cell comprising the polynucleotide or the vector or expressing the polypeptide or the chimeric polypeptide disclosed herein under suitable conditions.

In some aspects, the present disclosure provides a method of treating a tumor in a subject in need thereof, comprising administering to the subject an immune cell, which overexpresses a c-Jun polypeptide and comprises a chimeric antigen receptor (CAR) and a truncated EGF receptor (EGFRt), wherein the CAR is specific or an antigen expressed on the tumor. In some aspects, the immune cell comprises any of the modified cells disclosed herein.

In some aspects, the tumor is derived from a cancer comprising a breast cancer, head and neck cancer, uterine cancer, brain cancer, skin cancer, renal cancer, lung cancer, colorectal cancer, prostate cancer, liver cancer, bladder cancer, kidney cancer, pancreatic cancer, thyroid cancer, esophageal cancer, eye cancer, stomach (gastric) cancer, gastrointestinal cancer, ovarian cancer, carcinoma, sarcoma, leukemia, lymphoma, myeloma, or a combination thereof. In some aspects, the tumor is a solid tumor. In some aspects, the method further comprises administering at least one additional therapeutic agent to the subject. In some aspects, the at least one additional therapeutic agent comprises a chemotherapeutic drug, targeted anti-cancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the immune checkpoint inhibitor comprises an anti-PD-1 antibody, anti-PD-L1 antibody, anti-LAG-3 antibody, anti-CTLA-4 antibody, anti-GITR antibody, anti-TIM3 antibody, or any combination thereof.

In any of the treatment methods provided above (e.g., methods of treating a tumor), in some aspects, after the administration the size of the tumor (tumor size) is decreased compared to a reference tumor size. In some aspects, the reference tumor size comprises: (i) the tumor size before the administration, (ii) the tumor size in a corresponding subject that did not receive the administration (e.g., received an administration of a corresponding immune cell that does not overexpress the c-Jun polypeptide), or (iii) both (i) and (ii). In some aspects, compared to the reference tumor size, the tumor size is decreased by at least about 5%, at least about 10%, at least about 20%, at least about 30%, at least about 40%, at least about 50%, at least about 60%, at least about 70%, at least about 80%, at least about 90% or about 100%.

In any of the treatment methods provided above (e.g., methods of treating a tumor), in some aspects, after the administration the duration of survival of the subject is increased compared to a reference duration of survival. In some aspects, the reference duration of survival comprises the duration of survival of a corresponding subject who did not receive the administration (e.g., received an administration of a corresponding immune cell that does not overexpress the c-Jun polypeptide). In some aspects, compared to the reference duration of survival, the duration of survival is increased by at least about one week, at least about two weeks, at least about three weeks, at least about one month, at least about two months, at least about three months, at least about four months, at least about five months, at least about six months, at least about seven months, at least about eight months, at least about nine months, at least about 10 months, at least about 11 months, or at least about one year.

In any of the treatment methods provided above (e.g., methods of treating a tumor), in some aspects, after the administration the immune cell is capable of persisting in the subject longer compared to a corresponding immune cell that does not overexpress the c-Jun polypeptide.

In some aspects, after the administration, the immune cells are capable of persisting in the subject for at least about 1 month, at least about 2 months, at least about 3 months, at least about 4 months, at least about 5 months, or at least about 6 months longer than the corresponding immune cells. In some aspects, there are between about 1-fold and about 10-fold as many of the administered immune cells present in the subject, as compared to the corresponding immune cells present in a reference subject who received an administration of the corresponding immune cells, at about one month, about two months, about three months, about four months, about five months, about six months, about seven months, or about eight months after the administration.

Present disclosure further provides a method of killing tumor cells comprising contacting the tumor cells with an immune cell, which overexpresses a c-Jun polypeptide and comprises a chimeric antigen receptor (CAR) and a truncated EGF receptor (EGFRt), wherein the CAR is specific for an antigen expressed on the tumor cells. In some aspects, the immune cell comprises any of the modified cells provided herein.

In some aspects, the killing of the tumor cells is increased compared to a reference method, in which the tumor cells are contacted with a corresponding immune cell that does not overexpress the c-Jun polypeptide. In some aspects, the reference method, the killing of the tumor cells is increased by at least about 0.5-fold, 1-fold, at least about 2-fold, at least about 3-fold, at least about 4-fold, or at least about 5-fold.

Also provided herein is a method of increasing the production of a cytokine by an immune cell in response to antigen stimulation comprising modifying an immune cell to (i) express a ROR-1 binding protein and (ii) have an increased level of a c-Jun polypeptide as compared to a corresponding immune cell that has not been modified to have increased level of the c-Jun polypeptide, wherein the ROR-1 binding protein specifically binds to the same epitope as the R12 antibody.

In some aspects, the cytokine comprises IFN-γ, IL-2, or both. In some aspects, after the modification, the production of the cytokine in response to the antigen stimulation is increased by at least about 1-fold, at least about 2-fold, at least about 3-fold, at least about 4-fold, or at least about 5-fold compared to the corresponding immune cell. In some aspects, the increase in the production of the cytokine is measured using a Meso Scale Discovery (MSD) U-Plex assay.

In some aspects, the present disclosure further provides a method of increasing proliferation of an immune cell in response to antigen stimulation comprising modifying an immune cell to (i) express a ROR-1 binding protein and (ii) have an increased level of a c-Jun polypeptide as compared to a corresponding immune cell that has not been modified to have increased level of the c-Jun polypeptide, wherein the ROR-1 binding protein specifically binds to the same epitope as the R12 antibody.

In some aspects, after the modification, the proliferation of the immune cell in response to antigen stimulation is increased by at least about 1-fold, at least about 2-fold, at least about 3-fold, at least about 4-fold, or at least about 5-fold compared to the corresponding immune cell. In some aspects, the increased proliferation results in greater number of the immune cells.

Provided herein is a method of increasing effector function of an immune cell in response to persistent antigen stimulation comprising modifying an immune cell to (i) express a ROR-1 binding protein and (ii) have an increased level of a c-Jun polypeptide as compared to a corresponding immune cell that has not been modified to have increased level of the c-Jun polypeptide, wherein the ROR-1 binding protein specifically binds to the same epitope as the R12 antibody.

In some aspects, the immune cell retains effector function for at least one, at least two, or at least three additional rounds of an antigen stimulation assay, as compared to the corresponding immune cell. In some aspects, the effector function comprises the ability: (i) to kill tumor cells (ii) to produce a cytokine upon further antigen stimulation, or (iii) both (i) and (ii). In some aspects, the effector function of the immune cell is increased by at least about 1-fold, at least about 2-fold, at least about 3-fold, at least about 4-fold, or at least about 5-fold as compared to the corresponding immune cell.

Provided herein is a method of reducing or preventing exhaustion of an immune cell in response to persistent antigen stimulation comprising modifying an immune cell to (i) express a ROR-1 binding protein and (ii) have an increased level of a c-Jun polypeptide as compared to a corresponding immune cell that has not been modified to have increased level of the c-Jun polypeptide, wherein the ROR-1 binding protein specifically binds to the same epitope as the R12 antibody. In some aspects, after the modification, in response to the persistent antigen stimulation, the immune cells express: (i) decreased level of genes associated with exhaustion, (ii) increased level of genes associated with activation, or (iii) both (i) and (ii), as compared to the corresponding immune cell.

In some aspects, an immune cell useful for the above methods is modified to comprise any of the polynucleotides described herein.

BRIEF DESCRIPTION OF THE DRAWINGS/FIGURES

Figure 1B:
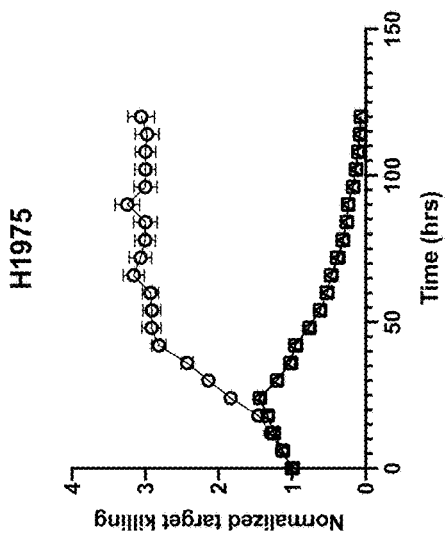

FIGS. 1A and 1B show that anti-ROR1 CAR T cells described herein (e.g., anti-ROR1 CAR T cell overexpressing c-Jun) selectively lyse ROR1-expressing NSCLC tumor cells. Mock (untransduced) T cells, Control R12 (e.g., not expressing c-Jun) CAR T cells, or c-Jun-R12 CART cells were coincubated with either NSCLC tumor cells expressing ROR1 ("$H_{1975}$") (FIG. 1A) or NSCLC tumor cells that lack ROR1 expression ("$H_{1975}$-ROR1KO") (FIG. 1B) expressing NucLight Red (NLR; nuclear-restricted mKate2) at an effector-to-target (E:T) cell ratio of 1:1 for 120 hours. The total number of NLR-positive cells were counted over time (x-axis) and normalized to the count at time point 0 h to calculate normalized target killing (y-axis).

FIGS. 2A, 2B, 2C, and 2D show that c-Jun overexpression enhances ROR1-dependent cytokine secretion by the anti-ROR1 CAR T cells but does not increase tonic signaling. Mock (untransduced) T cells, control anti-ROR1 CAR T cells (i.e., not overexpressing c-Jun), or anti-ROR1 CAR T cells overexpressing c-Jun were coincubated with either NSCLC tumor cells expressing ROR1 (FIGS. 2A and 2C) or NSCLC tumor cells that lack ROR1 expression (FIGS. 2B and 2D) at an effector-to-target (E:T) cell ratio of 1:1 for 24 hours, at which point supernatant from coculture wells were collected for cytokine quantification. The concentrations of IL-2 (FIGS. 2A and 2B) and IFN-γ (FIGS. 2C and 2D) were measured using the Meso Scale Discovery (MSD) U-Plex. The results shown in FIGS. 2A-2D are from three independent donors (i.e., donor 1, donor 2, and donor 3).

Figure 3A:
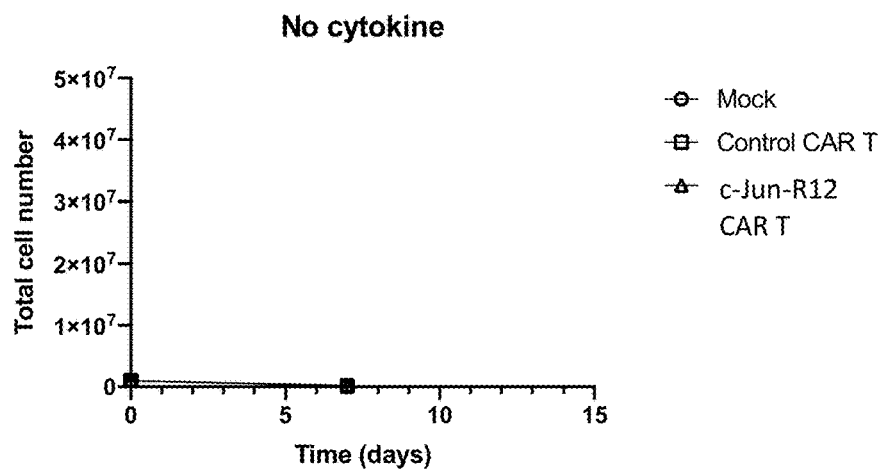
Figure 3B:
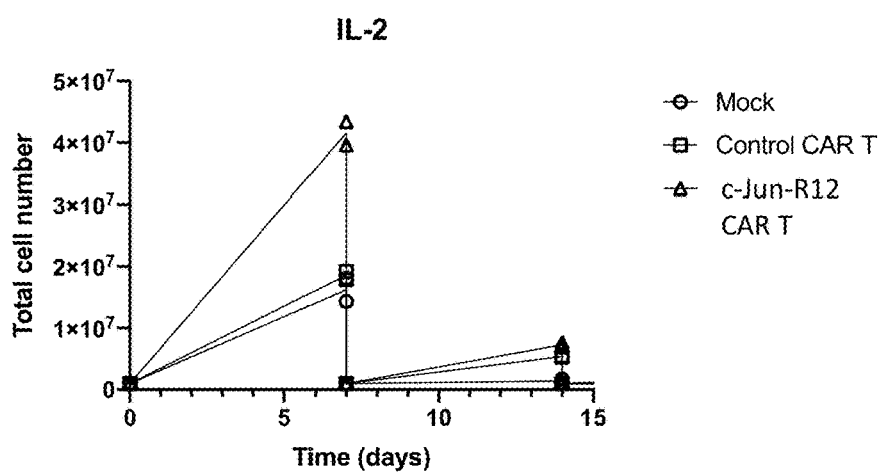
Figure 3C:
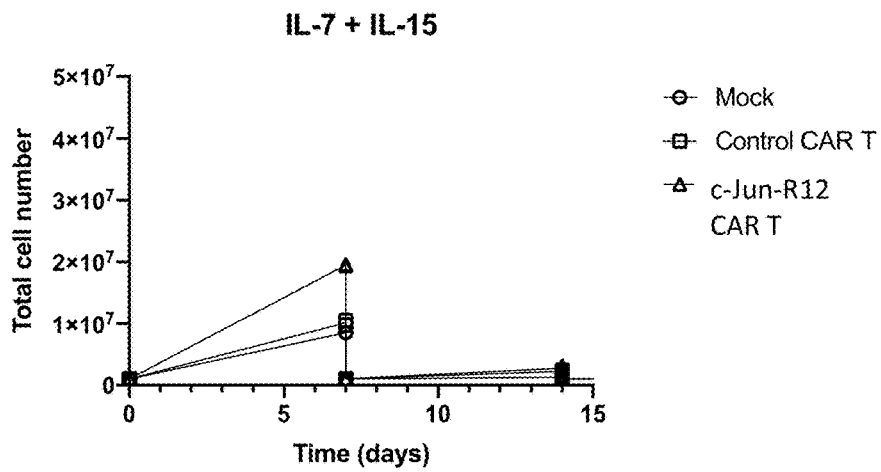

FIGS. 3A, 3B, and 3C show that c-Jun overexpression enhances cytokine-dependent proliferative capacity of anti-ROR1 CAR T cells. Mock (untransduced) T cells, control anti-ROR1 CART cells (i.e., not overexpressing c-Jun), or anti-ROR1 CART cells overexpressing c-Jun were separately cultured in a Grex 24 well plate with either basal T-cell media (FIG. 3A), T-cell media+200 IU/ml IL-2 (FIG. 3B), or T-cell media+1200 IU/ml IL-7+200 IU/mL IL-15 (FIG. 3C). On Day 0, 1 million cells were seeded for each condition and every 7 days, and cells were counted and reseeded at 1 million cells. Total cell number (y-axis) shows actual T cell numbers at the end of each expansion.

Figure 4A:
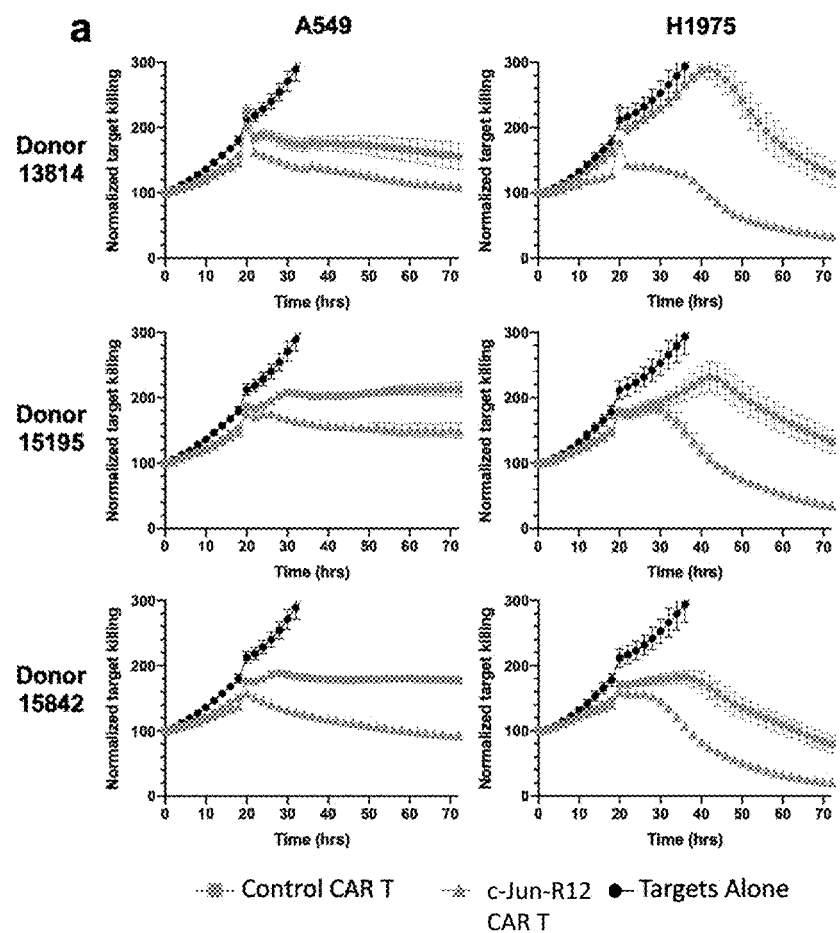
Figure 4B:
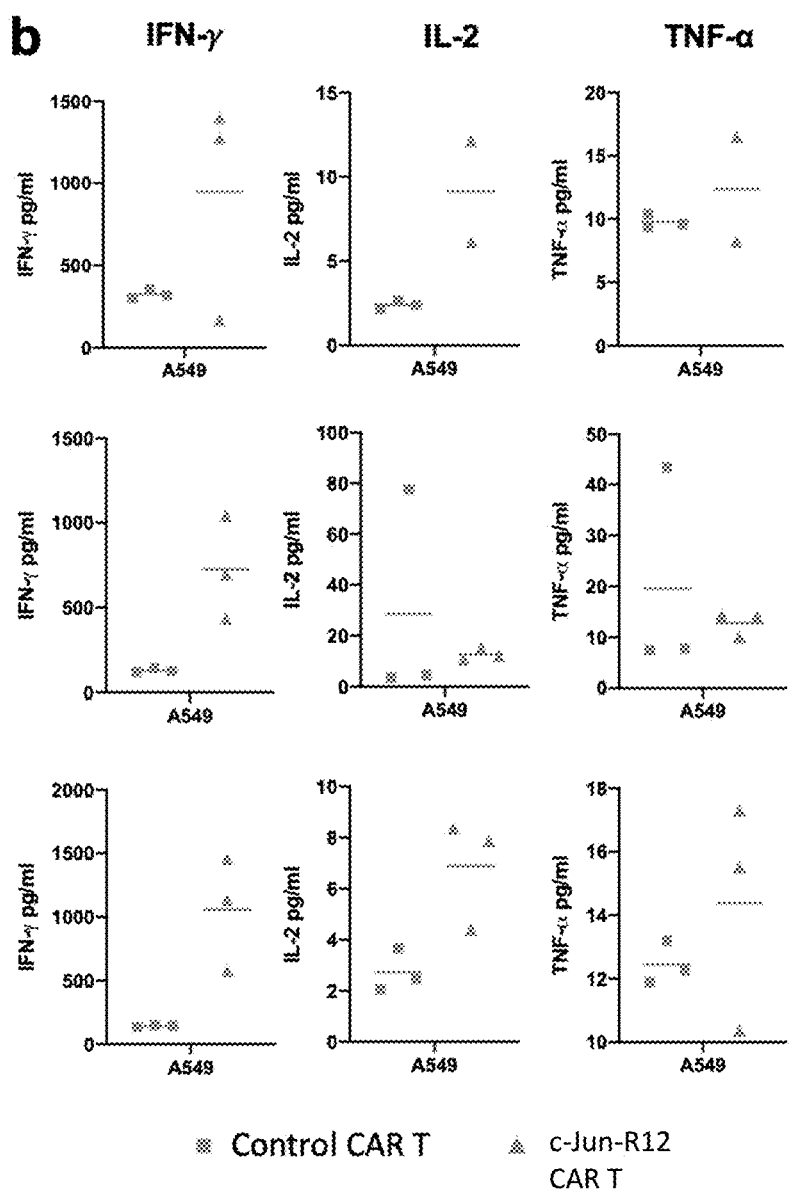

FIGS. 4A and 4B show that c-Jun overexpression prolongs cytolytic activity and IFN-γ secretion by anti-ROR1 CAR T cells following chronic exposure to ROR1-expressing NSCLC tumor cell lines. Control anti-ROR1 CAR T cells (i.e., not overexpressing c-Jun) or anti-ROR1 CAR T cells overexpressing c-Jun were chronically stimulated by exposure to ROR1+ A549 NSCLC tumor cells for 7 days. Chronic antigen exposure was ensured by re-plating CAR T cells with fresh target cells at a 1:1 E:T ratio every 2 days. On Day 7 post chronic stimulation, CAR T cells were collected and coincubated with either A549-NLR (E:T cell ratio 1:1) or $H_{1975}$-NLR (E:T 1:5). Lysis of target cells was evaluated by tracking total NLR intensity, normalized to time 0 h of assay setup (FIG. 4A). 24-h supernatants were collected for IFN-γ, IL-2, and TNF-α quantification by MSD (FIG. 4B). n=3 donors (D13814, D15195, and D15842).

Figure 5B:
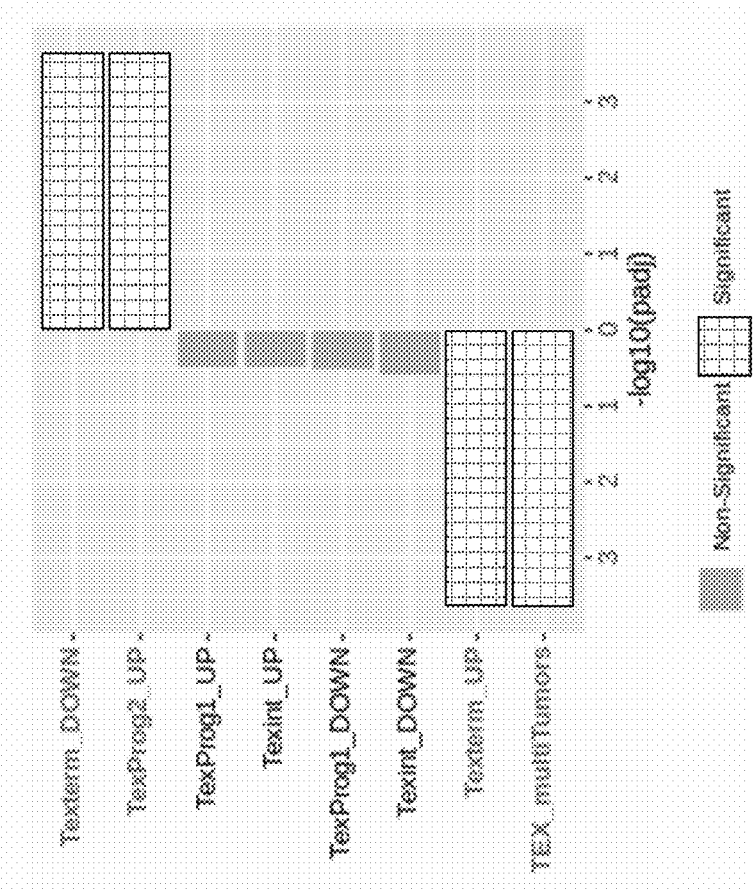
Figure 5A:
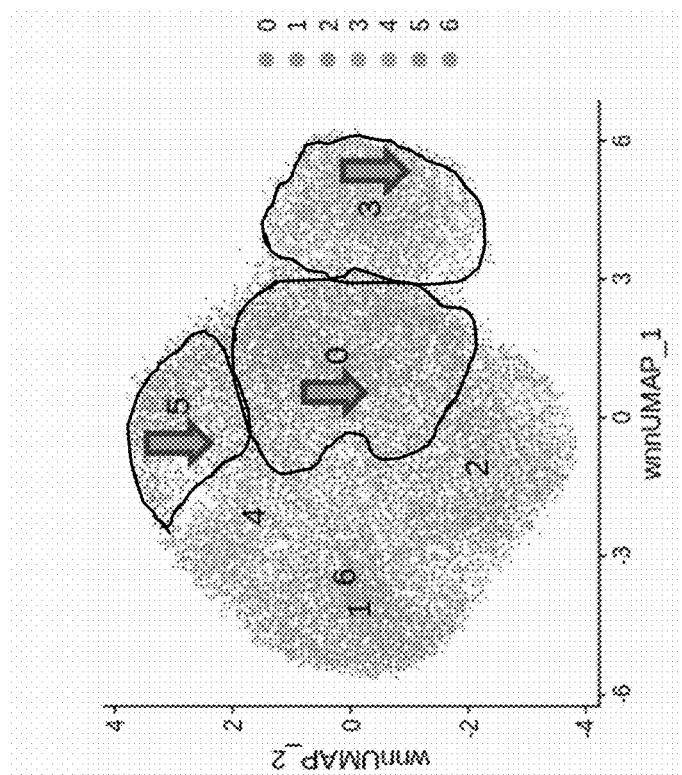
Figure 5C:
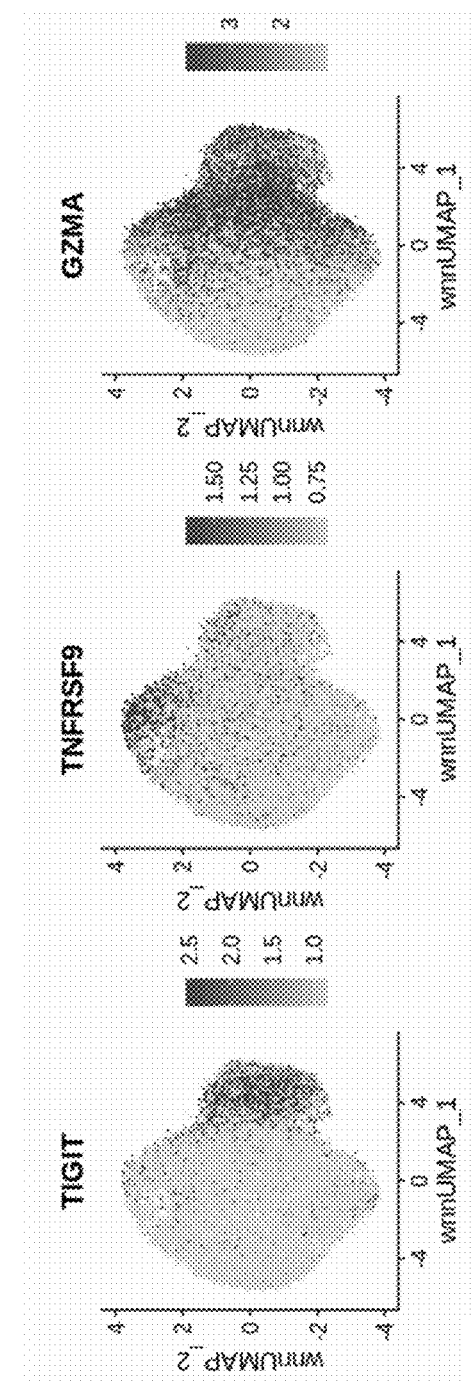
Figure 5D:
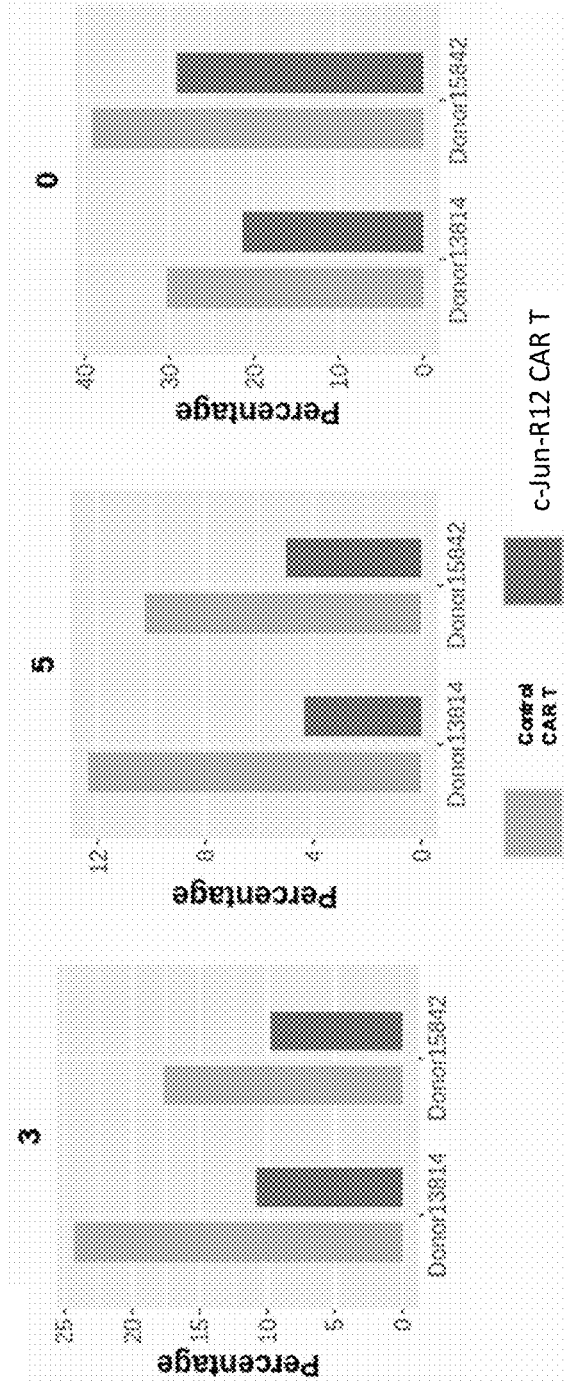

FIGS. 5A, 5B, 5C, and 5D show that c-Jun overexpression reduces exhaustion-associated transcriptional profile in anti-ROR1 CAR T cells following chronic antigen stimulation. Results shown are from single-cell CITE-seq (using Seurat) in 2 donors. FIG. 5A shows gene-set enrichment (fgsea) on differential expression of genes between ±CAR+ T cells overexpression c-Jun at Day 7 after chronic stimulation. FIG. 5B shows uniform manifold approximation and projection of ±CAR+ cells overexpressing c-Jun from single cells. Each dot represents a cell projected onto a 2-dimensional space. Markers for clusters with decreasing frequencies (clusters 0, 3, and 5) when c-Jun is added and corresponding frequencies are shown (see arrows). Cluster 3 was comprised of cells predominantly enriched for literature-based exhaustion markers. Clusters 0 and 5 were comprised of cells predominantly enriched for literature-based T cell differentiated/activated markers (e.g., TIGIT, TNFRSF9, granzyme A). FIG. 5C shows the expression of TIGIT (1' graph), CD137 (TNFRSF9; $2n^d$ graph), and granzyme A (GZMA; $3^{rd}$ graph) in the anti-ROR1 CAR T cells overexpression c-Jun from FIG. 5B on a 2-dimensional space. FIG. 5D shows that clusters 0, 3 and 5, which are enriched for exhaustion markers (cluster 3) and differentiated/activated markers (0, 5) decreased in frequency (decrease in percentage of cells) with addition of c-Jun.

Figure 6:
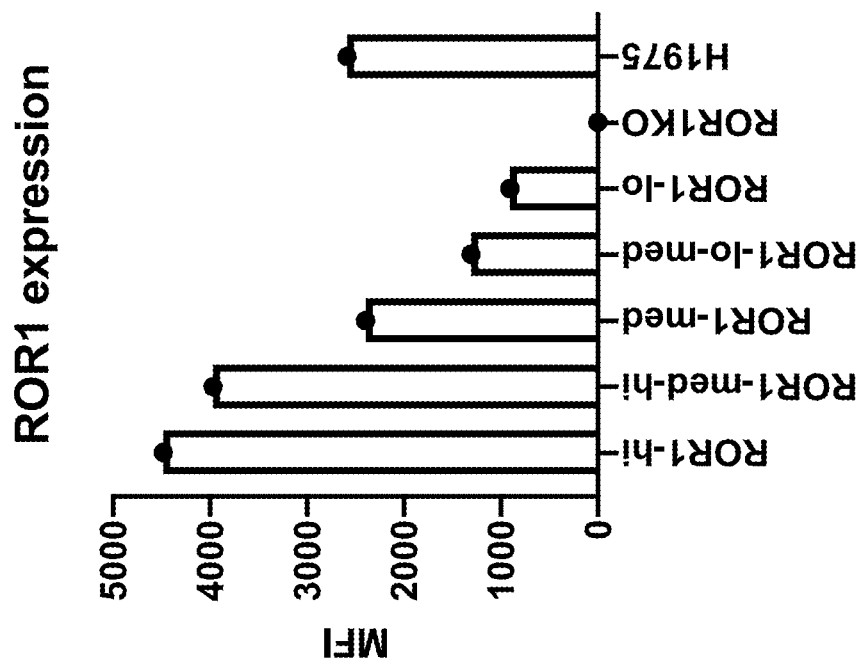

FIG. 6 shows varying ROR1 expression levels on engineered NSCLC cell line $H_{1975}$. A set of mutated encephalomyocarditis virus internal ribosome entry site elements with varying strengths was used to control the relative expression of human ROR1 over a wide range and introduced into $H_{1975}$ cell line lacking ROR1 expression. The expression levels of ROR1 by the cell lines (x-axis) is represented as geometric MFI (y-axis).

FIG. 7 shows that c-Jun overexpression does not alter the antigen density threshold required for cytolytic activity of anti-ROR1 CART cells against NSCLC cell lines expressing low levels of ROR1. Mock (untransduced) T cells, control anti-ROR1 CAR T cells (i.e., not overexpressing c-Jun), or anti-ROR1 CAR T cells overexpressing c-Jun were incubated with NSCLC cell line ($H_{1975}$) expressing NLR and varying levels of ROR1 (as described in FIG. 6) for 148 hours, during which the total number of NLR-positive cells were counted and normalized to the count at time point 0 h to calculate normalized target killing (4 donors; effector-to-target [E:T] ratio=1:16). ROR1 knock out and ROR1-low expressing cells are shown in the top left and top right panels, respectively. ROR1-low-medium and ROR1-medium expressing cells are shown in the middle left and right panels, respectively. ROR1-medium-high and ROR1-high expressing cells are shown in the bottom left and bottom right panels, respectively.

Figure 8B:
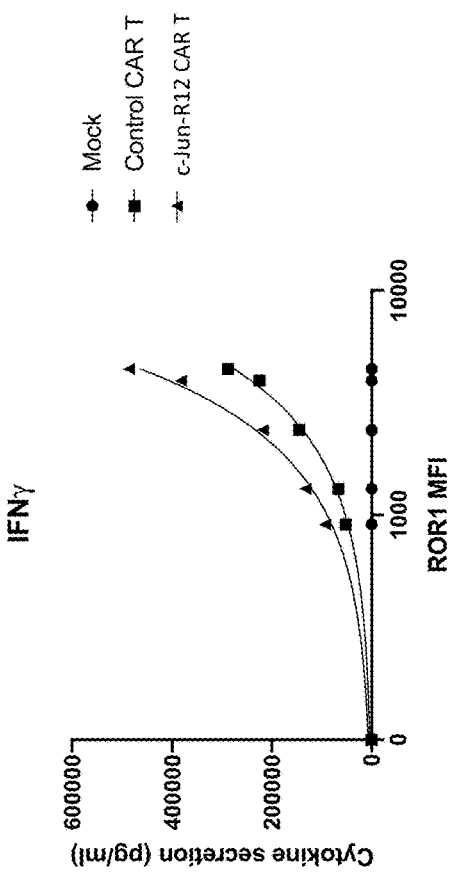
Figure 8A:
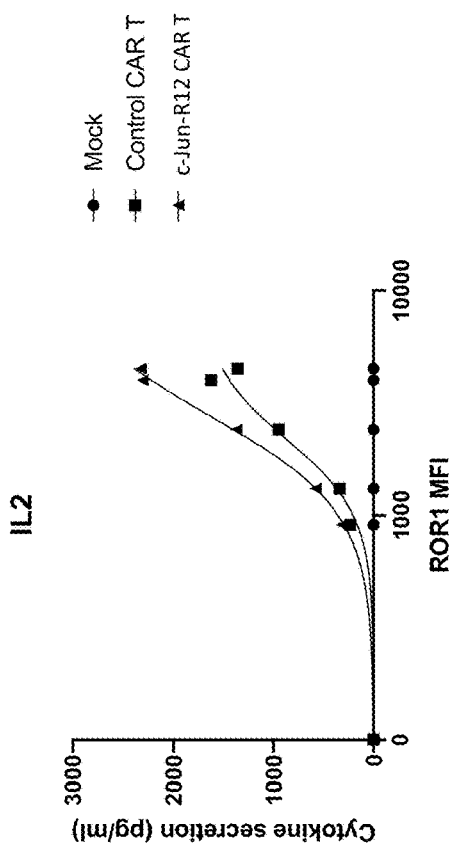

FIGS. 8A and 8B show that c-Jun overexpression does not substantially alter the antigen density threshold required for cytokine secretion by the anti-ROR1 CAR T cells in response to $H_{1975}$ NSCLC cell lines expressing low levels of ROR1. Mock (untransduced) T cells (circle), control anti-ROR1 CAR T cells (i.e., not overexpressing c-Jun) (square), or anti-ROR1 CAR T cells overexpressing c-Jun (triangle) were incubated in wells containing $H_{1975}$ cells expressing varying levels of ROR1 (as described in FIG. 6) for 24 hours, at which point supernatant from the wells were collected for IL-2 (FIG. 8A) and IFN-γ (FIG. 8B) quantification. The concentrations were measured using the Meso Scale Discovery (MSD) U-Plex (4 donors; effector-to-target [E:T] ratio=1:1).

Figure 9A:
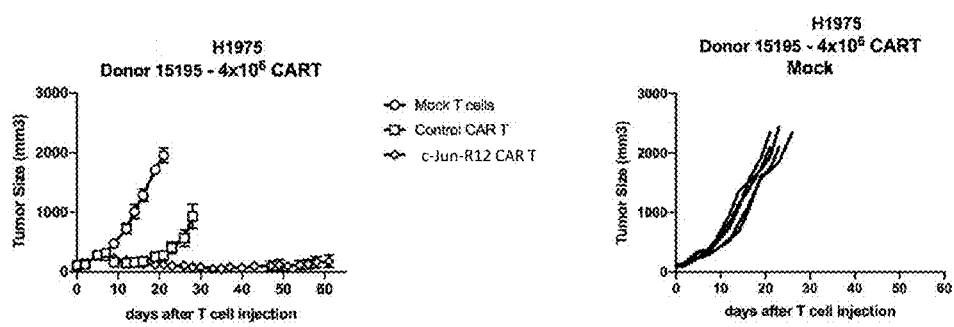
Figure 9B:
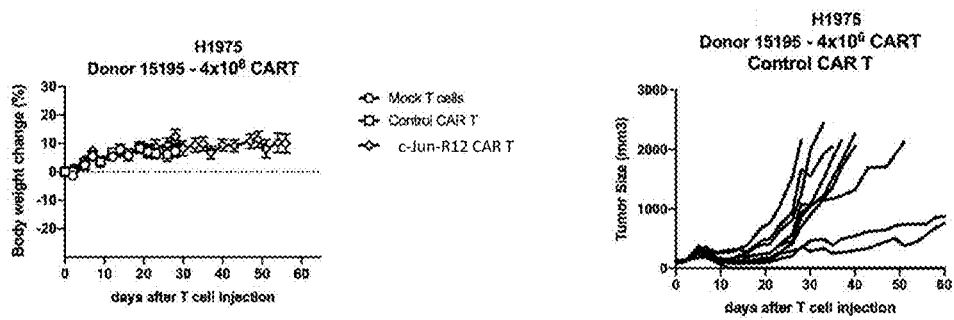
Figure 9C:
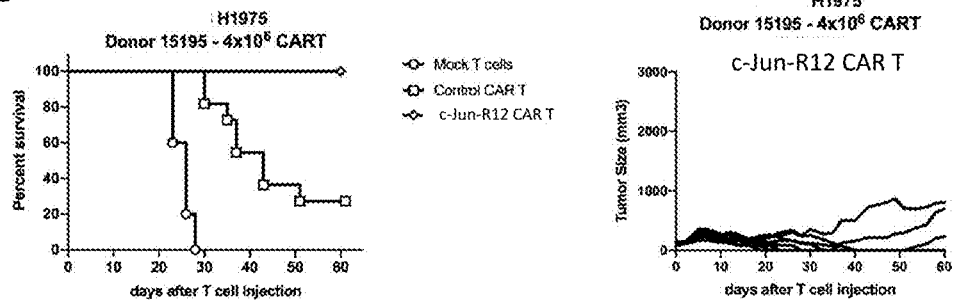

FIGS. 9A, 9B, and 9C provide comparison of the anti-tumor effects of anti-ROR1 CAR T cells described herein (e.g., overexpressing c-Jun). Animals implanted subcutaneously with human ROR1-positive $H_{1975}$ NSCLC cells were treated intravenously with a single dose ($4\times10^6$ cells) of one of the following: (i) high dose of mock (untransduced) T cells, (ii) control anti-ROR1 CAR T cells (i.e., not overexpressing c-Jun), and (iii) anti-ROR1 CAR T cells overexpressing c-Jun. Then, tumor size (FIG. 9A), body weight (FIG. 9B), and survival (FIG. 9C) of the animals were assessed at various time points post CAR T cell administration.

Figure 10:
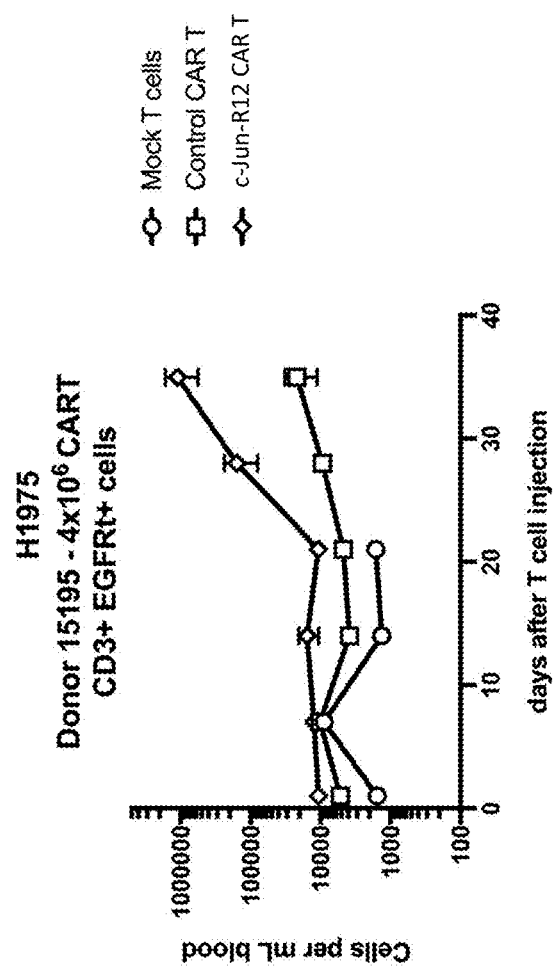

FIG. 10 shows the persistence of anti-ROR1 CART cells in $H_{1795}$ tumor-bearing NSG mice. As shown, the animals received a single intravenous administration of one of the following: (i) mock (untransduced) T cells (circle), (ii) control anti-ROR1 CAR T cells (i.e., not overexpressing c-Jun) (triangle), and (iii) anti-ROR1 CAR T cells overexpressing c-Jun (diamond). Then, at various time points post-administration, peripheral blood was collected and the number of CART cells per mL of blood was quantified using flow cytometry.

DETAILED DESCRIPTION OF THE DISCLOSURE

The present disclosure is directed to a polynucleotide (e.g., isolated polynucleotide) encoding a chimeric binding protein (e.g., CAR). In some aspects, the polynucleotide comprises one or more additional nucleotide sequences encoding a c-Jun protein and/or a truncated EGFR. As described herein, in some aspects, the expression of these additional components (i.e., c-Jun protein and/or the truncated EGFR) can improve one or more properties of a cell modified to express the chimeric binding protein. The present disclosure provides engineered cells, such as T cells, that express the polynucleotides described herein. The engineered T cells, e.g., ROR-specific CAR T cells, overexpress c-Jun. Overexpression of c-Jun in T cells helps sustain the active state of the cells by, e.g., alleviating or preventing T cell dysfunction (e.g., T cell exhaustion). The present engineered T cells exhibit sustained, potent cytotoxicity against ROR1-bearing tumor cells. As compared to T cells that do not overexpress c-Jun, the present engineered T cells display fewer signs of T cell exhaustion and increased signs of persistent effector cells.

Before the present disclosure is described in greater detail, it is to be understood that this disclosure is not limited to the particular compositions or process steps described, as such can, of course, vary. As will be apparent to those of skill in the art upon reading this disclosure, each of the individual aspects described and illustrated herein has discrete components and features which can be readily separated from or combined with the features of any of the other several aspects without departing from the scope or spirit of the present disclosure. Any recited method can be carried out in the order of events recited or in any other order which is logically possible.

The headings provided herein are not limitations of the various aspects of the disclosure, which can be defined by reference to the specification as a whole. It is also to be understood that the terminology used herein is for the purpose of describing particular aspects only, and is not intended to be limiting, since the scope of the present disclosure will be limited only by the appended claims.

Accordingly, the terms defined immediately below are more fully defined by reference to the specification in its entirety.

Terms

In order that the present description can be more readily understood, certain terms are first defined. Except as otherwise expressly provided herein, each of the following terms shall have the meaning set forth below. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, 'a' represents adenine, 'c' represents cytosine, 'g' represents guanine, 't' represents thymine, and 'u' represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The terms "administration," "administering," and grammatical variants thereof refer to introducing a composition of the present disclosure (e.g., a polynucleotide encoding a CAR or a cell expressing a CAR), into a subject via a pharmaceutically acceptable route. The introduction of a composition of the present disclosure (e.g., a polynucleotide encoding a CAR or a cell expressing a CAR), into a subject is by any suitable route, including intratumorally, orally, pulmonarily, intranasally, parenterally (intravenously, intraarterially, intramuscularly, intraperitoneally, or subcutaneously), rectally, intralymphatically, intrathecally, periocularly or topically.

Administration includes self-administration and the administration by another. A suitable route of administration allows the composition or the agent to perform its intended function. For example, if a suitable route is intravenous, the composition is administered by introducing the composition or agent into a vein of the subject.

The term "amino acid substitution" refers to replacing an amino acid residue present in a parent or reference sequence (e.g., a wild type sequence) with another amino acid residue. An amino acid can be substituted in a parent or reference sequence (e.g., a wild type polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In some aspects, substitution patterns can be described according to the schema An(YZ), wherein A is the single letter code corresponding to the amino acid residue substituting the amino acid naturally or originally present at position n, and Y and Z are alternative substituting amino acid residues that can replace A.

As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some aspects, two or more sequences are said to be "completely conserved" or "identical" if they are 100% identical to one another. In some aspects, two or more sequences are said to be "highly conserved" if they are at least about 70% identical, at least about 75% identical, at least about 80% identical, at least about 85% identical, at least about 90% identical, or at least about 95% identical to one another. In some aspects, two or more sequences are said to be "highly conserved" if they are about 70% identical, about 75% identical, about 80% identical, about 85% identical, about 90% identical, about 95% identical, about 98% identical, or about 99% identical to one another. In some aspects, two or more sequences are said to be "conserved" if they are at least about 30% identical, at least about 35% identical, at least about 40% identical, at least about 45% identical, at least about 50% identical, at least about 55%, at least about 60% identical, at least about 65% identical, at least about 70% identical, at least about 75% identical, at least about 80% identical, at least about 85% identical, at least about 90% identical, or at least about 95% identical to one another. In some aspects, two or more sequences are said to be "conserved" if they are about 30% identical, about 35% identical, about 40% identical, about 45% identical, about 50% identical, about 55% identical, about 60% identical, about 65% identical, about 70% identical, about 75% identical, about 80% identical, about 85% identical, about 90% identical, about 95% identical, about 98% identical, or about 99% identical to one another. Conservation of sequence can apply to the entire length of a polynucleotide or polypeptide or can apply to a portion, region or feature thereof.

"Derived from" as that term is used herein, indicates a relationship (e.g., structural similarity) between a first and a second molecule. For example, in the case of a CAR spacer of the present disclosure comprising an amino acid sequence derived from a human immunoglobulin sequence (e.g., a hinge and/or a constant region sequence), the sequence that is derived from the human immunoglobulin sequence (e.g., a hinge and/or a constant region sequence) can comprise or consist of a full hinge, a hinge fragment, a full hinge or a fragment of an hinge plus additional residues adjacent to the hinge in a wild type immunoglobulin (e.g., one or more amino acids from a constant domain such as a $CH_1$ or $CH_2$ domain), or can comprise or consist of the full sequence of a loop region, a loop region fragment, or a loop region fragment plus additional residues adjacent to the loop in a wild type immunoglobulin (e.g., one or more amino acids from a secondary structure element, e.g., a β-sheet, adjacent to a loop region in a $CH_1$, $CH_2$ or $CH_3$ domain). In some aspects, a spacer derived from constant domain can be derived from a light chain constant domain (CL).

The term "loop region" as used herein refers to a primary sequence of amino acid residues which connects two regions comprising secondary structure, such as an α-helix or β-sheet, in the immediate N-terminal and C-terminal directions of primary structure from the loop region. Examples of loop regions include, but are not limited to, $CH_2$ or $CH_3$ loop regions. The immunoglobulin fold comprises a 2-layer sandwich of 7-9 antiparallel β-strands arranged in two β-sheets with a Greek key topology. Accordingly, constant domain derived CAR spacers of the present disclosure can comprise, consist, or consist essentially of a loop sequence (or a fragment thereof) connecting β-sheet A and β-sheet B, β-sheet B and β-sheet C, β-sheet C and β-sheet C', β-sheet C' and β-sheet C", β-sheet C" and β-sheet D, β-sheet D and β-sheet E, β-sheet E and β-sheet F, or β-sheet F and β-sheet G, in an immunoglobulin domain, e.g., a constant immunoglobulin domain (e.g., $CH_1$, $CH_2$, $CH_3$, or CL).

CAR spacers derived from a human Ig immunoglobulin (e.g., a hinge and/or a constant region sequence), disclosed herein also encompass sequences generated by covalently linking via peptidic bonds a hinge region derived sequence as described above, i.e., the spacer can be a polymer comprising multiple repeats of a full hinge, fragments thereof, or combinations thereof.

In some aspects, a nucleic acid sequence that is "derived from" a second nucleic acid sequence (e.g., a TM domain sequence of the presently disclosed CAR derived from a CD8a TM sequence) can include a nucleotide sequence that is identical or substantially similar to the nucleotide sequence of the second nucleic acid sequence. In some aspects, a nucleic acid sequence can be obtained by, for example, naturally occurring mutagenesis, artificial directed mutagenesis or artificial random mutagenesis. The mutagenesis used to derive nucleotides can be intentionally directed or intentionally random, or a mixture of each. The mutagenesis of a nucleotide to create a different nucleotide derived from the first can be a random event (e.g., caused by polymerase infidelity) and the identification of the derived nucleotide can be made by appropriate screening methods, e.g., as discussed herein.

In some aspects, a nucleotide or amino acid sequence that is derived from a second nucleotide sequence has a sequence identity of at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% to the second nucleotide sequence, respectively, wherein the first nucleotide sequence retains the biological activity of the second nucleotide sequence.

The terms "complementary" and "complementarity" refer to two or more oligomers (i.e., each comprising a nucleobase sequence), or between an oligomer and a target gene, that are related with one another by Watson-Crick base-pairing rules. For example, the nucleobase sequence "T-G-A (5'→3')," is complementary to the nucleobase sequence "A-C-T (3'→5')." Complementarity can be "partial," in which less than all of the nucleobases of a given nucleobase sequence are matched to the other nucleobase sequence according to base pairing rules. For example, in some aspects, complementarity between a given nucleobase sequence and the other nucleobase sequence can be about 70%, about 75%, about 80%, about 85%, about 90% or about 95%. Or, there can be "complete" or "perfect" (100%) complementarity between a given nucleobase sequence and the other nucleobase sequence to continue the example. The degree of complementarity between nucleobase sequences has significant effects on the efficiency and strength of hybridization between the sequences.

The term "downstream" refers to a nucleotide sequence that is located 3' to a reference nucleotide sequence. In certain aspects, downstream nucleotide sequences relate to sequences that follow the starting point of transcription. For example, the translation initiation codon of a gene is located downstream of the start site of transcription. The term "upstream" refers to a nucleotide sequence that is located 5' to a reference nucleotide sequence.

As used herein, the terms "antigen-binding domain" and "antibody" encompass an immunoglobulin whether natural or partly or wholly synthetically produced, and antigen-binding portions thereof. The term also covers any protein having a binding domain that is homologous to an immunoglobulin binding domain. "Antigen-binding domain" and "antibody" further include a polypeptide comprising a framework region from an immunoglobulin protein or portions thereof that specifically binds and recognizes an antigen, and comprises at least one CDR. Use of the terms "antigen-binding domain" and "antibody" is meant to include whole antibodies, polyclonal, monoclonal and recombinant antibodies, portions thereof, and further includes single-chain antibodies, humanized antibodies, murine antibodies, chimeric, mouse-human, mouse-primate, primate-human monoclonal antibodies, anti-idiotype antibodies, antibody constructs, such as, e.g., scFv, (scFv)$_2$, Fab, Fab', and F(ab')$_2$, F(ab1)$_2$, Fv, dAb, and Fd, disulfide-linked Fvs (dsFcs), and antibody-related polypeptides.

In some aspects, an "antigen-binding portion" refers to a polypeptide sequence that makes contacts with the antigen, including but not limited to CDRs derived from an antibody.

An antigen-binding portion can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen-binding portions can also be grafted into scaffolds based on polypeptides such as a fibronectin type III (Fn3)(see U.S. Pat. No. 6,703,199, which describes fibronectin polypeptide minibodies). Thus, the terms "antigen-binding domain" and "antibody" include also antibody mimics based on the scaffold of the fibronectin type III domain (monobodies), other scaffolding systems (e.g., tenascin) in which one or more CDRs are grafted, aptamers, etc.

The terms "antigen-binding domain" and "antibody" also include other suitable antigen-binding domains that can be used according to the present disclosure, e.g., nanobody, VHH antibody, DARPin (designed ankyrin repeat proteins), affibody, monobody, adnectin, alphabody, Albumin-binding domain, Adhiron, Affilin and other gamma-B crystallin-derived artificial proteins, Affimer, Affitin (NANOFITIN™), Anticalin, Armadillo repeat proteins (ARM-repeat protein such as, e.g., β-catenin, a-importing, plakoglobin, adenomatous polyposis coli, ARMC4, ARMCX3, etc.), Atrimer (e.g., tetranectin and derived proteins), Avimer/Maxibody, Centyrin, Fynomer and other Fyn SH$_3$ domain-derived proteins, Kunitz domain, Obody/OB-fold, Pronectin, Repebody, or any synthetic and/or computationally designed binding-protein or scaffold.

The modular architecture of antibodies has been exploited to create more than 60 different bispecific or multispecific antibody formats. Accordingly, in some aspects, the antibody can be in a format selected, e.g., from crossMab, DAF (Dual Action Fab) (two-in-one), DAF (four-in-one), Duta-Mab, DT-IgG, Knobs-in-holes common LC, Knobs-in-holes assembly, Charge pair, Fab-arm exchange, SEEDbody, Tri-omab, LUZ-Y (bispecific antibody with a leucize zipper inducing heterodimerization of two HCs), Fcab, KX-body, Orthogonal Fab, DVD-IgG (dual variable domain IgG), IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG (four-in-one), Nanobody, Nanobody-HSA, BiTE (bispecific T cell engager), Diabody, DART (dual-affinity-retargeting), TandAb (tandem antibody), scDiabody, scDiabody-CH$_3$, Triple Body, Miniantibody, Minibody, TriBi minibody, scFv-CH$_3$ KIH, Fab-scFv, scFv-CH-CL-scFv, F(ab')2, F(ab') 2-ScFv2, scFv-KIH, Fab-scFv-Fc, Tetravalent HC Ab, scDiabody-Fc, Diabody-Fc, Tandem scFv-Fc, Intrabody, Dock and Locck, ImmTAC, HSAbody, scDiabody-HSA, Tandem scFv-Toxin, IgG-IgG, Cov-X-Body, and scFv1-PEG-scFV2.

"Antigen-binding domain" and "antibody" also include bispecific antibodies and multispecific antibodies so long as they exhibit the desired biological activity or function. In some aspects, the chimeric binding protein (e.g., CAR) of the present disclosure comprising an extracellular antigen-binding domain, e.g., an scFv.

The term "scFv" refers to a fusion protein comprising at least one antibody portion comprising a variable region of a light chain and at least one antibody portion comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv can have the VL and VH variable regions in either order, e.g., with respect to the N-terminal and C-terminal ends of the polypeptide, the scFv can comprise VL-linker-VH or can comprise VH-linker-VL.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme), or a combination thereof. Under the Kabat numbering scheme, in some aspects, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some aspects, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some aspects, the CDRs correspond to the amino acid residues that are part of a Kabat CDR, a Chothia CDR, or both. For instance, in some aspects, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

As used herein, "cell engineering" or "cell modification" (including derivatives thereof) refers to the targeted modification of a cell, e.g., an immune cell disclosed herein. In some aspects, the cell engineering comprises viral genetic engineering, non-viral genetic engineering, introduction of receptors to allow for tumor specific targeting (e.g., an anti-ROR1 CAR) introduction of one or more endogenous genes that improve T cell function, introduction of one or more synthetic genes that improve immune cell, e.g., T cell, function (e.g., a polynucleotide encoding a c-Jun polypeptide, such that the immune cell exhibits increased c-Jun expression compared to a corresponding cell that has not been modified), or any combination thereof. As further described elsewhere in the present disclosure, in some aspects, a cell can be engineered or modified with a transcription activator (e.g., CRISPR/Cas system-based transcription activator), wherein the transcription activator is capable of inducing and/or increasing the endogenous expression of a protein of interest (e.g., c-Jun).

The term "antigen" refers to a molecule that provokes an immune response. This immune response can involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA.

As used herein, the term "epitope" refers to the moieties of an antigen that specifically interact with an antibody molecule. Such moieties, referred to herein as epitopic determinants, typically comprise, or are part of, elements such as amino acid side chains or sugar side chains. An epitopic determinate can be defined, e.g., by methods known in the art, e.g., by crystallography or by hydrogen-deuterium exchange. At least one or some of the moieties on the antibody molecule that specifically interact with an epitopic determinant are typically located in a CDR(s). Typically an epitope has a specific three dimensional structural characteristics. Typically an epitope has specific charge characteristics. Some epitopes are linear epitopes while others are conformational epitopes.

The term "autologous" refers to any material derived from the same individual to whom it is later to be re-introduced into the individual.

The term "chimeric antigen receptor" or alternatively a "CAR" refers to a set of polypeptides, typically two in the simplest form, which when in an immune effector cell, provides the cell with specificity for a target cell, typically a cancer cell, and with intracellular signal generation. In some aspects, a CAR comprises at least an extracellular antigen-binding domain, a transmembrane domain and a cytoplasmic signaling domain (also referred to herein as "an intracellular signaling domain") comprising a functional signaling domain derived from a stimulatory molecule and/or costimulatory molecule as defined below. In some aspects, the set of polypeptides are in the same polypeptide chain, e.g., comprise a chimeric fusion protein. In some aspects, the set of polypeptides are not contiguous with each other, e.g., are in different polypeptide chains. In some aspects, the set of polypeptides include a dimerization switch that, upon the presence of a dimerization molecule, can couple the polypeptides to one another, e.g., can couple an antigen-binding domain to an intracellular signaling domain. In some aspects, the stimulatory molecule of the CAR is the zeta chain associated with the T cell receptor complex (e.g., CD3 zeta). In some aspects, the cytoplasmic signaling domain comprises a primary signaling domain (e.g., a primary signaling domain of CD3-zeta). In some aspects, the cytoplasmic signaling domain further comprises one or more functional signaling domains derived from at least one costimulatory molecule as defined below. In some aspects, the costimulatory molecule is chosen from the costimulatory molecules described herein, e.g., 4-1BB (i.e., CD137), CD27, and/or CD28.

In some aspects, the CAR comprises a chimeric fusion protein comprising an antigen-binding domain, a transmembrane domain, and an intracellular signaling domain comprising a functional signaling domain derived from a stimulatory molecule, wherein the antigen-binding domain and the transmembrane domain are linked by a CAR spacer. In some aspects, the CAR comprises a chimeric fusion protein comprising an antigen-binding domain linked to a transmembrane domain via a CAR spacer and an intracellular signaling domain comprising a functional signaling domain derived from a costimulatory molecule and a functional signaling domain derived from a stimulatory molecule. In some aspects, the CAR comprises a chimeric fusion protein comprising an antigen-binding domain linked to a transmembrane domain via a CAR spacer and an intracellular signaling domain comprising two functional signaling domains derived from one or more costimulatory molecule(s) and a functional signaling domain derived from a stimulatory molecule. In some aspects, the CAR comprises a chimeric fusion protein comprising an antigen-binding domain linked to a transmembrane domain via a CAR spacer and an intracellular signaling domain comprising at least two functional signaling domains derived from one or more costimulatory molecule(s) and a functional signaling domain derived from a stimulatory molecule. In some aspects, the CAR comprises an optional leader sequence at the amino-terminus (N-terminus) of the CAR. In some aspects, the CAR further comprises a leader sequence at the N-terminus of the antigen-binding domain, wherein the leader sequence is optionally cleaved from the antigen-binding domain (e.g., a scFv) during cellular processing and localization of the CAR to the cellular membrane.

While the present application often uses CARs to illustrate the different aspects of the disclosed subject matter, it will be apparent to a skilled artisan that the relevant disclosures provided herein can equally apply to other chimeric binding proteins. As used herein, the term "chimeric binding protein" refers to proteins that are capable of binding to one or more antigens (e.g., comprising an antigen-binding moiety) and are created through the joining of two or more heterologous polynucleotides which originally coded for separate proteins or fragments of proteins or multiple fragments of the same protein connected in a non-naturally occurring orientation. Non-limiting examples of other chimeric binding proteins include a T cell receptor (TCR) (e.g., engineered TCR), chimeric antibody-T cell receptor (caTCR), chimeric signaling receptor (CSR), T cell receptor mimic (TCR mimic), and combinations thereof. Accordingly, unless indicated otherwise, the term CARs, in some aspects, can encompass other types of chimeric binding proteins known in the art, e.g., those described herein.

The term "cancer" refers to a disease characterized by the uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors.

The terms "cancer associated antigen" or "tumor antigen" or variants thereof interchangeably refer to a molecule (typically protein, carbohydrate or lipid) that is preferentially expressed on the surface of a cancer cell, either entirely or as a fragment (e.g., MHC/peptide), in comparison to a normal cell, and which is useful for the preferential targeting of a pharmacological agent to the cancer cell. In some aspects, a tumor antigen is a marker expressed by both normal cells and cancer cells, e.g., a lineage marker, e.g., CD19 on B cells. In certain aspects, the tumor antigen is derived from, cancers including but not limited to primary or metastatic melanoma, thymoma, lymphoma, sarcoma, lung cancer, liver cancer, non-Hodgkin lymphoma, Hodgkin lymphoma, leukemias, uterine cancer, cervical cancer, bladder cancer, kidney cancer and adenocarcinomas such as breast cancer, prostate cancer, ovarian cancer, pancreatic cancer, and the like.

In some aspects, the tumor antigen is an antigen that is common to a specific proliferative disorder. In some aspects, a cancer-associated antigen is a cell surface molecule that is overexpressed in a cancer cell in comparison to a normal cell, for instance, about 1-fold over expression, about 2-fold overexpression, about 3-fold overexpression or more in comparison to a normal cell. In some aspects, a cancer-associated antigen is a cell surface molecule that is inappropriately synthesized in the cancer cell, for instance, a molecule that contains deletions, additions or mutations in comparison to the molecule expressed on a normal cell. In some aspects, a cancer-associated antigen will be expressed exclusively on the cell surface of a cancer cell, entirely or as a fragment (e.g., MHC/peptide), and not synthesized or expressed on the surface of a normal cell.

The term "anti-cancer effect" refers to a biological effect which can be manifested by various means, including but not limited to, e.g., a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In some aspects, a string of amino acids can be conservatively replaced with a structurally similar string that differs in order and/or composition of side chain family members.

Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can also be used. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

In the content of the present disclosure, the terms "mutation" and "amino acid substitution" as defined above (sometimes referred simply as a "substitution") are considered interchangeable.

In the context of the present disclosure, substitutions (even when they are referred to as amino acid substitution) are conducted at the nucleic acid level, i.e., substituting an amino acid residue with an alternative amino acid residue is conducted by substituting the codon encoding the first amino acid with a codon encoding the second amino acid.

As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present disclosure, the term homology encompasses both to identity and similarity.

In some aspects, polymeric molecules are considered to be "homologous" to one another if at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% of the monomers in the molecule are identical (exactly the same monomer) or are similar (conservative substitutions). The term "homologous" necessarily refers to a comparison between at least two sequences (polynucleotide or polypeptide sequences).

As used herein, the term "identity" refers to the overall monomer conservation between polymeric molecules, e.g., between polypeptide molecules or polynucleotide molecules (e.g. DNA molecules and/or RNA molecules). The term "identical" without any additional qualifiers, e.g., protein A is identical to protein B, implies the sequences are 100% identical (100% sequence identity). Describing two sequences as, e.g., "70% identical," is equivalent to describing them as having, e.g., "70% sequence identity."

Calculation of the percent identity of two polypeptide sequences, for example, can be performed by aligning the two sequences for optimal comparison purposes (e.g., gaps can be introduced in one or both of a first and a second polypeptide sequences for optimal alignment and non-identical sequences can be disregarded for comparison purposes). In certain aspects, the length of a sequence aligned for comparison purposes is at least about 30%, at least about 40%, at least about 50%, at least about 60%, at least about 70%, at least about 80%, at least about 90%, at least about 95%, or about 100% of the length of the reference sequence. The amino acids at corresponding amino acid positions are then compared.

When a position in the first sequence is occupied by the same amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity (% ID) or of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art. It is understood that percentage of similarity is contingent on the comparison scale used, i.e., whether the amino acids are compared, e.g., according to their evolutionary proximity, charge, volume, flexibility, polarity, hydrophobicity, aromaticity, isoelectric point, antigenicity, or combinations thereof.

As used herein, the terms "isolated," "purified," "extracted," and grammatical variants thereof are used interchangeably and refer to the state of a preparation of desired composition of the present disclosure, e.g., a CAR of the present disclosure, that has undergone one or more processes of purification. In some aspects, isolating or purifying as used herein is the process of removing, partially removing (e.g., a fraction) of a composition of the present disclosure, e.g., a CAR of the present disclosure from a sample containing contaminants.

In some aspects, an isolated composition has no detectable undesired activity or, alternatively, the level or amount of the undesired activity is at or below an acceptable level or amount. In some aspects, an isolated composition has an amount and/or concentration of desired composition of the present disclosure, at or above an acceptable amount and/or concentration and/or activity. In some aspects, the isolated composition is enriched as compared to the starting material from which the composition is obtained. This enrichment can be by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, at least about 99.9%, at least about 99.99%, at least about 99.999%, at least about 99.9999%, or greater than 99.9999% as compared to the starting material.

In some aspects, isolated preparations are substantially free of residual biological products. In some aspects, the isolated preparations are 100% free, at least about 99% free, at least about 98% free, at least about 97% free, at least about 96% free, at least about 95% free, at least about 94% free, at least about 93% free, at least about 92% free, at least about 91% free, or at least about 90% free of any contaminating biological matter. Residual biological products can include abiotic materials (including chemicals) or unwanted nucleic acids, proteins, lipids, or metabolites.

"Nucleic acid," "nucleic acid molecule," "nucleotide sequence," "polynucleotide," and grammatical variants thereof are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Single stranded nucleic acid sequences refer to single-stranded DNA (ssDNA) or single-stranded RNA (ssRNA). Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alfa, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the disclosure comprises one or more nucleic acids as described herein.

The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose) and polyribonucleotides (containing D-ribose), including mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA.

In some aspects, a polynucleotide disclosed herein comprises a DNA, e.g., a DNA inserted in a vector. In some aspects, a polynucleotide disclosed herein comprises an mRNA. In some aspects, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine).

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a nucleotide sequence "encoding" an amino acid "sequence," e.g., a polynucleotide "encoding" a CAR of the present disclosure, includes all nucleotide sequences that are degenerate versions of each other and that encode the same amino acid sequence.

The term "expression" refers to the transcription and/or translation of a particular nucleotide sequence driven by a promoter.

The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term "polypeptide," as used herein, refers to proteins, polypeptides, and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some aspects, a "peptide" can be less than or equal to 50 amino acids long, e.g., about 5, 10, 15, 20, 25, 30, 35, 40, 45, or 50 amino acids long.

A "recombinant" polypeptide or protein refers to a polypeptide or protein produced via recombinant DNA technology. Recombinantly produced polypeptides and proteins expressed in engineered host cells are considered isolated for the purpose of the disclosure, as are native or recombinant polypeptides which have been separated, fractionated, or partially or substantially purified by any suitable technique. The polypeptides encoded by the polynucleotides disclosed herein (e.g., anti-ROR1 CAR, c-Jun, and/or EGFRt) can be recombinantly produced using methods known in the art. In some aspects, the polypeptides encoded by the polynucleotides of the present disclosure (e.g., anti-ROR1 CAR, c-Jun, and/or EGFRt) are produced by cells, e.g., T cells, following transfection with at least one polynucleotide or vector encoding the polypeptides described here.

As used herein, the term "fragment" of a polypeptide (e.g., a c-Jun polypeptide) refers to an amino acid sequence of a polypeptide that is shorter than the naturally-occurring sequence, N- and/or C-terminally deleted or any part of the polypeptide deleted in comparison to the naturally occurring polypeptide. Thus, a fragment does not necessary need to have only N- and/or C-terminal amino acids deleted. A polypeptide in which internal amino acids have been deleted with respect to the naturally occurring sequence is also considered a fragment.

As used herein, the term "functional fragment" refers to a polypeptide fragment that retains polypeptide function. Accordingly, in some aspects, a functional fragment of an Ig hinge, retains the ability to position an antigen-binding domain (e.g., an scFv) in a CAR at a distance from a target epitope (e.g., a tumor antigen) such that the antigen-binding domain (e.g., an scFv) can effectively interact with the target epitope (e.g., a tumor antigen). Similarly, in some aspects, a c-Jun functional fragment is a fragment that when expressed in a CAR T cell, results in a CAR T cell with, e.g., at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100% of the activity of a reference CAR T cell expressing a corresponding full length c-Jun. Non-limiting examples of such activity are further described elsewhere in the present disclosure.

As used herein, the term "reference CAR T cell" refers to a corresponding CAR T cell comprising the same structural CAR components but does not overexpress c-Jun.

As further described elsewhere in the present disclosure, a polynucleotide encoding a CAR (e.g., anti-ROR1 CAR) described herein can comprise additional nucleotide sequences encoding a c-Jun protein or a functional fragment thereof. Whether a c-Jun fragment is a functional fragment can be assessed by any known methods to determine c-Jun activation (e.g., a colorimetric c-Jun transcription factor assay kit (colorimetric) from abcam™), etc. Overexpression of c-Jun in T cells, such as CAR T cells described herein, helps sustain the active state of the cells by alleviating or preventing T cell dysfunction (e.g., T cell exhaustion). Accordingly, functional fragments of c-Jun can be assessed based on their ability to confer this activity in engineered immune cells, such as CAR T cells described herein. Such activity includes, but are not limited to, sustained, potent cytotoxicity against target-bearing tumor cells (e.g., ROR1+ tumor cells) (e.g., ability to lyse or kill the tumor cells) or reduced signs of T cell exhaustion (e.g., decreased expression of inhibitory receptors, such as PD-1) and increased signs of persistent effector cells. Such methods for assessing T cell exhaustion and thereby assessing functional fragments of c-Jun include, for example, assays useful for measuring exhaustion, cell phenotype, persistence, cytotoxicity and/or killing, proliferation, cytokine release, and gene expression profiles known in the art such as, flow cytometry, intracellular cytokine staining (ICS), IncuCyte immune cell killing analysis, Meso Scale Discovery (MSD) or similar assay, persistent antigen stimulation assay, sequential antigen stimulation assay (similar to persistent antigen stimulation assay but without resetting E:T cell ratio with each round of restimulation), bulk and single cell RNAseq (see e.g., Fron Genet. 2020; 11:220; 2019 Bioinformatics 35:i436-445; 2019 Annual Review of Biomed. Data Sci. 2:139-173); cytotoxicity/killing assays, ELISA, western blot and other standard molecular and cell biology methods such as described herein or as described, for example, in Current Protocols in Molecular Biology or Current Protocols in Immunology (John Wiley & Sons, Inc., 1999-2021) or elsewhere.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, variants or derivatives include, e.g., modified polypeptides. In some aspects, variants or derivatives of, e.g., polypeptides, polynucleotides, lipids, glycoproteins, are the result of chemical modification and/or endogenous modification. In some aspects, variants or derivatives are the result of in vivo modification. In some aspects, variants or derivatives are the result of in vitro modification. In some aspects, variant or derivatives are the result of intracellular modification in producer cells, e.g., T cells.

Modifications present in variants and derivatives include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination.

The term "signaling domain" refers to the functional portion of a protein which acts by transmitting information within the cell to regulate cellular activity via defined signaling pathways by generating second messengers or functioning as effectors by responding to such messengers.

An "intracellular signaling domain," as the term is used herein, refers to an intracellular portion of a molecule. The intracellular signaling domain can generate a signal that promotes an immune effector function of the CAR containing cell, e.g., an anti-ROR1 CAR T cell described herein. Non-limiting examples of immune effector function, e.g., in a CAR T cell, include cytolytic activity and helper activity, including the secretion of cytokines. In some aspects, the intracellular signal domain is the portion of the protein which transduces the effector function signal and directs the cell to perform a specialized function. While the entire intracellular signaling domain can be employed, in many cases, it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

In some aspects, the intracellular signaling domain can comprise a primary intracellular signaling domain. Exemplary primary intracellular signaling domains include those derived from the molecules responsible for primary stimulation, or antigen dependent simulation. In some aspects, the intracellular signaling domain can comprise a costimulatory intracellular domain. Exemplary costimulatory intracellular signaling domains include those derived from molecules responsible for costimulatory signals, or antigen independent stimulation. For example, in the case of a CART cell (e.g., anti-ROR1 CART cells described herein), a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, common FcR gamma (FCER1G), Fc gamma RIIa, FcR beta (Fc Epsilon Rib), CD3 gamma, CD3 delta, CD3 epsilon, CD22, CD79a, CD79b, CD278 (ICOS), FcεRI, CD66d, CD32, DAP10, and DAP12.

The terms "covalently linked," "fused," and grammatical variants thereof are used interchangeably and refer to a first moiety, e.g., a first amino acid sequence or nucleotide sequence, covalently or non-covalently joined to a second moiety, e.g., a second amino acid sequence or nucleotide sequence, respectively. The first moiety can be directly joined or juxtaposed to the second moiety or alternatively an intervening moiety can covalently join the first moiety to the second moiety. The term "linked" means not only a fusion of a first moiety to a second moiety at the C-terminus or the N-terminus, but also includes insertion of the whole first moiety (or the second moiety) into any two points, e.g., amino acids, in the second moiety (or the first moiety, respectively). In some aspects, the first moiety is linked to a second moiety by a peptide bond or a linker. The first moiety can be linked to a second moiety by a phosphodiester bond or a linker. The linker can be a peptide or a polypeptide (for polypeptide chains) or a nucleotide or a nucleotide chain (for nucleotide chains) or any chemical moiety (for polypeptide or polynucleotide chains or any chemical molecules).

As used herein, the term "pharmaceutical composition" refers to one or more of the compounds described herein, such as, e.g., a CAR of the present disclosure or a cell expressing a CAR, or a cell expressing a CAR and overexpressing c-Jun, of the present disclosure, mixed or intermingled with, or suspended in one or more other chemical components, such as pharmaceutically-acceptable carriers and excipients. One purpose of a pharmaceutical composition is to facilitate administration of preparations of, e.g., cell expressing a CAR and overexpressing c-Jun as described herein to a subject.

The terms "excipient" and "carrier" are used interchangeably and refer to an inert substance added to a pharmaceutical composition to further facilitate administration of a compound, e.g., a CAR of the present disclosure or a cell engineered to express a CAR, c-Jun and in certain aspects, a truncated EGFR.

The terms "pharmaceutically-acceptable carrier," "pharmaceutically-acceptable excipient," and grammatical variations thereof, encompass any of the agents approved by a regulatory agency of the U.S. Federal government or listed in the U.S. Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

The terms "subject," "patient," "individual," and "host," and variants thereof are used interchangeably herein and refer to any mammalian subject, including without limitation, humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired, particularly humans. The methods described herein are applicable to both human therapy and veterinary applications.

As used herein, the phrase "subject in need thereof" includes subjects, such as mammalian subjects, that would benefit from administration of a composition described herein (e.g., anti-ROR1 CAR T cells of the present disclosure), e.g., to improve one or more symptoms associated with a disease or disorder described herein (e.g., cancer).

The terms "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In some aspects, the term "treating" or "treatment" means inducing an immune response in a subject against an antigen.

The terms "prevent," "preventing," and variants thereof as used herein, refer partially or completely delaying onset of an disease, disorder and/or condition; partially or completely delaying onset of one or more symptoms, features, or clinical manifestations of a particular disease, disorder, and/or condition; partially or completely delaying onset of one or more symptoms, features, or manifestations of a particular disease, disorder, and/or condition; partially or completely delaying progression from a particular disease, disorder and/or condition; and/or decreasing the risk of developing pathology associated with the disease, disorder, and/or condition. In some aspects, preventing an outcome is achieved through prophylactic treatment.

As used herein the term "therapeutically effective amount" is the amount of reagent or pharmaceutical compound comprising a composition disclosed herein (e.g., anti-ROR1 CAR T cells of the present disclosure) that is sufficient to a produce a desired therapeutic effect, pharmacologic and/or physiologic effect on a subject in need thereof.

A therapeutically effective amount can be a "prophylactically effective amount" as prophylaxis can be considered therapy. As used herein, "prophylactic" refers to a therapeutic or course of action used to prevent the onset of a disease or condition, or to prevent or delay a symptom associated with a disease or condition. As used herein, a "prophylaxis" refers to a measure taken to maintain health and prevent the onset of a disease or condition, or to prevent or delay a symptom associated with a disease or condition.

ROR1

As is apparent from the present disclosure, a polynucleotide described herein comprises a nucleotide sequence encoding a chimeric binding protein (e.g., CAR) which specifically binds to ROR1. Receptor tyrosine kinase—like orphan receptor 1 (ROR1) is overexpressed in approximately 57% of patients with triple negative breast cancer (TNBC) and 42% of patients with non-small cell lung carcinoma (NSCLC) adenocarcinomas (Balakrishnan 2017), and represents a highly attractive target for chimeric antigen receptor (CAR) T cells. Receptor tyrosine kinase—like orphan receptor 1-positive (ROR1$^+$) solid tumors can be safely targeted with anti-ROR1 CAR T cells (Specht 2020); however, efficacy has been limited, in part, because the CAR T cells exhibit exhaustion or dysfunction following infusion in patients with solid-tumor malignancies. In addition, solid tumors have immune-suppressive barriers that limit antitumor activity of immunotherapies, such as CART cells (Newick 2016, Srivastava 2018, Martinez 2019). Without wishing to be bound by any one theory, cells expressing the anti-ROR1 chimeric binding proteins described herein have been modified to overexpress the transcription factor c-Jun and are more resistant to exhaustion and exhibit improved effector functions compared to other anti-ROR1 cells available in the art.

In some aspects, the nucleotide sequence encoding a CAR of the present disclosure, i.e., an anti-ROR1 CAR, comprises an antigen-binding domain comprising an antibody or an antigen-binding fragment thereof (e.g., an ScFv) that specifically binds to an epitope on a tumor antigen, e.g., a protein kinase such as a tyrosine protein kinase.

In some aspects, the tumor antigen is the tyrosine-protein kinase transmembrane receptor "ROR1," also known as neurotrophic tyrosinase kinase, receptor-related 1 (NTRKR1). The human amino acid and nucleic acid sequences can be found in a public database, such as GenBank, UniProt and Swiss-Prot. For example, the amino acid sequences of isoforms 1 and 2 precursors of human ROR1 can be found at Accession Nos. NP_005003.2 and NP_001077061.1, respectively, and the mRNA sequences encoding them can be found at Accession Nos. NM_005012.3 and NM_001083592.1, respectively. As used herein, "ROR1" includes proteins comprising mutations, e.g., point mutations, fragments, insertions, deletions and splice variants of full length wild-type ROR1. In some aspects the antigen-binding portion of the CAR recognizes and binds an antigen within the extracellular domain of the ROR1 protein. In some aspects, the ROR1 protein is expressed on a cancer cell.

ROR1 is a member of the receptor tyrosine kinase-like orphan receptor (ROR) family. In humans ROR1 is encoded by the ROR1 gene. The protein encoded by this gene is a receptor tyrosine kinase that modulates growth in the central nervous system and has a role in the metastasis of cancer cells. ROR1 is considered a pseudokinase that lacks significant catalytic activity and interacts with the non-canonical Wnt signaling pathway. Increased expression of ROR1 is associated with cancer, e.g., with B-cell chronic lymphocytic leukemia. ROR1 is highly expressed in circulating tumor cells and promotes invasion of pancreatic cancer cells (Xu et al., 2018, Mol. Med. Rep. 18:5087-5094). ROR1 also appears to promote tumor progression in endometrial cancer, similar to its role in ovarian cancer (Henry et al, 2018, Gynecol. Oncol. 148:576-584). ROR1 is expressed in epithelial tumors (e.g., highly expressed in multiple epithelial cancer histologies) and is homogenously expressed on a subset of ovarian cancer, triple-negative breast cancer, and lung cancer (Balakrishnan et al., 2017, Clin, Cancer Res. 23:3061-3071). ROR1 expression has also been positively associated with lymph-node metastasis in colorectal cancer patients (Zhou et al., 2017, Oncotarget 8:32864-32872). Prior clinical data from ROR1 CAR T and ADC studies report no on-target off-tumor toxicity and no significant toxicity in non-human primates. Moreover, as demonstrated herein, the c-Jun overexpressing anti-ROR1 CAR T cells demonstrate anti-tumor efficacy both in vitro and in vivo. Specifically, improved cytokine production, prolonged cytotoxicity, and reduced exhaustion-associated gene expression profile were observed after chronic stimulation (e.g., in vitro), and in NSCLC mouse xenograft model, showed improved antitumor efficacy.

c-Jun

As described herein, in some aspects, a polynucleotide of the present disclosure (e.g., comprising a nucleotide sequence encoding a chimeric binding protein, e.g., CAR) comprises an additional nucleotide sequence encoding a c-Jun protein. In some aspects, the polynucleotide provided herein is a polycistronic polynucleotide wherein the polynucleotide encodes multiple proteins including c-Jun and a CAR and in some aspects, one or more additional proteins (e.g., a safety switch protein such as EGFRt). In certain aspects, a polynucleotide provided herein encodes a chimeric polypeptide (e.g., chimeric binding protein), which comprise a c-Jun polypeptide and a ROR1-binding protein. In some aspects, such a chimeric polypeptide can include cleavable linkers such that the c-Jun polypeptide and the ROR1-binding protein are cleaved into separate functioning proteins after translation.

In humans, the c-Jun protein is encoded by the JUN gene, which is located on chromosome 1 (nucleotides 58,780,791 to 58,784,047 of GenBank Accession No. NC_000001.11, minus strand orientation). Synonyms of the JUN gene, and the encoded protein thereof, are known and include "Jun proto-oncogene, AP-1 transcription factor subunit," "v-Jun avian sarcoma virus 17 oncogene homolog," "transcription factor AP-1," "Jun oncogene," "AP-1," "Jun activation domain binding protein," "p39" and "enhancer-binding protein API." The wild-type human c-Jun protein sequence is 331 amino acids in length. The amino acid and nucleic acid sequences of the wild-type human c-Jun are provided in Tables 1 and 2, respectively.

The wild type human c-Jun (UniProt identifier: P05412-1) protein sequence is 331 amino acids in length (SEQ ID NO: 1). The amino acid and nucleic acid sequences are shown in Table 1 and 2, respectively.

TABLE 1 c-Jun Protein sequence c-Jun (UniProt: P05412-1) (SEQ ID NO: 1)
MTAKMETTFYDDALNASFLPSESGPYGYSNPKILKQSMTLNLADPVGSLKPHLRAKNSDL
LTSPDVGLLKLASPELERLIIQSSNGHITTTPTPTQFLCPKNVTDEQEGFAEGFVRALAE
LHSQNTLPSVTSAAQPVNGAGMVAPAVASVAGGSGSGGFSASLHSEPPVYANLSNFNPGA
LSSGGGAPSYGAAGLAFPAQPQQQQQPPHHLPQQMPVQHPRLQALKEEPQTVPEMPGETP
PLSPIDMESQERIKAERKRMRNRIAASKCRKRKLERIARLEEKVKTLKAQNSELASTANM
LREQVAQLKQKVMNHVNSGCQLMLTQQLQTF

TABLE 2 c-Jun nucleic acid sequence

Wild-type JUN (GenBank Accession No. NM_002228.4) (SEQ ID NO: 2) *coding region is bolded and capitalized gctcagagttgcactgagtgtggctgaagcagcgaggcgggagtggaggtgcg
cggagtcaggcagacagacagacacagccagccagccaggtcggcagtatagt
ccgaactgcaaatcttattttcttttcaccttctctctaactgcccagagcta
gcgcctgtggctcccgggctggtgtttcgggagtgtccagagagcctggtctc
cagccgcccccggaggagagccctgctgcccagcgctgttgacagcggcgg
aaagcagcggtacccacgcgcccgccggggaagtcggcgagcggctgcagca
gcaaagaactttcccggctgggaggaccggagacaagtggcagagtcccggag
ccaacttttgcaagcctttcctgcgtcttaggcttctccacggcggtaaagac
cagaaggcgggagagccacgcaagagaagaaggacgtgcgctcagcttcgc
tcgcaccggttgttgaacttgggcgagcgcgagccgcggctgccgggcgcccc
ctcccccctagcagcggaggaggggacaagtcgtcggagtccgggcggccaaga
cccgccgccggccggccactgcagggtccgcactgatcgctccgcggggaga
gccgctgctctggaagtgagttcgcctgcggactccgaggaaccgctgcgca
cgaagagcgctcagtgagtgaccgcgacttttcaaagccgggtagcgcgcgcg
agtcgacaagtaagagtgcgggaggcatcttaattaaccctgcgctccctgga
gcgagctggtgaggagggcgcagcggggacgacagccagcgggtgcgtgcgct
cttagagaaactttccctgtcaaaggctccggggggcgcggggtgtcccccgct
tgccacagccctgttgcggccccgaaacttgtgcgcgcagcccaaactaacct
cacgtgaagtgacggactgttctATGACTGCAAAGATGGAAACGACCTTCTAT
GACGATGCCCTCAACGCCTCGTTCCTCCCGTCCGAGAGCGGACCTTATGGCTA
CAGTAACCCCAAGATCCTGAAACAGAGCATGACCCTGAACCTGGCCGACCCAG
TGGGGAGCCTGAAGCCGCACCTTCCGCGCCAAGAACTCGGACCTCCTCACCTCG
CCCGACGTGGGGCTGCTCAAGCTGGCGTCGCCCGAGCTGGAGCGCCTGATAAT
CCAGTCCAGCAACGGGCACATCACCACCACGCCGACCCCCACCCAGTTCCTGT
GCCCCAAGAACGTGACAGATGAGCAGGAGGGCTTCGCCGAGGGCTTCGTGCGC
GCCCTGGCCGAACTGCACAGCCAGAACACGCTGCCCAGCGTCACGTCGGCGGC
GCAGCCGGTCAACGGGGCAGGCATGGTGGCTCCCGCGGTAGCCTCGGTGGCAG
GGGGCAGCGGCAGCGGCGGCTTCAGCGCCAGCCTGCACAGCGAGCCGCCGGTC
TACGCAAACCTCAGCAACTTCAACCCAGGCGCGCTGAGCAGCGGCGGCGGGGC
GCCCTCCTACGGCGCGGCCGGCCTGGCCTTTCCCGCGCAACCCCAGCAGCAGC
AGCAGCCGCCGCACCACCTGCCCCAGCAGATGCCCGTCAGCACCCGCGGCTG
CAGGCCCTGAAGGAGGAGCCTCAGACAGTGCCCGAGATGCCCGGCGAGACACC
GCCCCTGTCCCCCATCGACATGGAGTCCCAGGAGCGGATCAAGGCGGAGAGGA
AGCGCATGAGGAACCGCATCGCTGCCTCCAAGTGCCGAAAAAGGAAGCTGGAG
AGAATCGCCCGGCTGGAGGAAAAAGTGAAAACCTTGAAAGCTCAGAACTCGGA
GCTGGCGTCCACGGCCAACATGCTCAGGGAACAGGTGGCACAGCTTAAACAGA
AAGTCATGAACCACGTTAACAGTGGGTGCCAACTCATGCTAACGCAGCAGTTG
CAAACATTTtgaagagagaccgtcgggggctgaggggcaacgaagaaaaaaaa
taacacagagagacagacttgagaacttgacaagttgcgacggagagaaaaaa
gaagtgtccgagaactaaagccaagggtatccaagttggactgggttgcgtcc
tgacggcgcccccagtgtgcacgagtgggaaggacttggcgcgcccccttg
gcgtggagccagggagcggccgcctgcgggctgccccgctttgcggacgggct
gtccccgcgcgaacgaacgttggacttttcgttaacattgaccaagaactgc
atgaaacctaacattcgatctcattcagtattaaagggggagggggaggggt
tacaaactgcaatagagactgtagattgcttctgtagtactccttaagaacac
aaagcggggggaggttgggagggcggcaggagggaggtttgtgagagcga
ggctgagcctacagatgaactctttctggcctgccttcgttaactgtgtatgt
acatatatatttttttaattgatgaaagctgattactgtcaataaacagct
tcatgcctttgtaagttatttcttgttgtttgtttgggtatcctgcccagtg
ttgtttgtaaataagagatttggagcactctgagtttaccatttgtaataaag
tatataattttttttatgttttgtttctgaaaattccagaaaggatatttaaga
aaatacaataaactattggaaagtactcccctaacctcttttctgcatcatct
gtagatactagctatctaggtggagttgaaagagttaagaatgtcgattaaaa
tcactctcagtgcttcttactattaagcagtaaaaactgttctctattagact
ttagaaataaatgtacctgatgtacctgatgctatggtcaggttatactcctc
ctccccccagctatctatatgaattgcttaccaaaggatagtgcgatgtttca
ggaggctgaggaagggggggttgcagtggagagggacagcccactgagaagtc
aaacatttcaaagtttggattgtatcaagtggcatgtgctgtgaccatttata
atgttagtagaaattttacaataggtgcttattctcaaagcaggaattggtgg
cagattttacaaaagatgtatccttccaatttggaatcttctctttgacaatt
cctagataaaaagatggcctttgcttatgaatatttataacagcattcttgtc
acaataaatgtattcaaataccaa Alternatively, c-Jun useful for the present disclosure can be a mutant human c-Jun, so long as the mutant c-Jun does not impact the mutant's ability to rescue dysfunctional (exhausted) T cells. In some aspects, a mutant c-Jun comprises at least about 70% (e.g., at least about 75%, at least about 80%, at least about 85%, at least about 90%, at least about 95%, at least about 96%, at least about 97%, at least about 98%, or at least about 99%) sequence identity with the C-terminal amino acid residues (e.g., C-terminal 50, 75, 100, 150, 200, or 250 or more residues), the C-terminal portion (e.g., quarter, third, or half) or C-terminal domains (e.g., epsilon, bZIP, and amino acids C-terminal thereof) of a wildtype c-Jun. In some aspects, the N-terminal amino acid residues (e.g., N-terminal 50, 75, 100, or 150 or more), the N-terminal portion (e.g., quarter, third, or half) or N-terminal domains (e.g., delta, transactivation domain, and amino acids N-terminal thereof) of a wildtype c-Jun are deleted, mutated, or otherwise inactivated.

In some aspects, the c-Jun comprises an inactivating mutation (e.g., substitutions, deletions, or insertions) in its transactivation domain and/or its delta domain. In some aspects, the c-Jun comprises one or both of S63A and S73A mutations (the positions are double underlined above). In some aspects, the c-Jun has a deletion between residues 2 and 102 or between residues 30 and 50 as compared to wildtype human c-Jun.

In some aspects, the c-Jun polypeptide comprises a truncated c-Jun polypeptide, as disclosed in WO2019/118902, which is expressly incorporated herein by reference in its entirety. In some aspects, the c-Jun polypeptide comprises an amino acid sequence having at least about 60%, at least about 70%, at least about 80%, at least about 90%, at least about 95%, at least about 96%, at least about 97%, at least about 98%, or at least about 99% sequence identity to SEQ ID NO: 1. In certain aspects, the c-Jun polypeptide comprises the amino acid sequence set forth in SEQ ID NO: 1.

In some aspects, the c-Jun nucleotide sequence disclosed herein can be codon-optimized using any methods known in the art. See, e.g., U.S. Publ. Nos. 2011/0081708 A1, 2014/0244228 A1, and 2019/0325989 A1, each of which is herein incorporated by reference in its entirety. For instance, in certain aspects, the codons of a c-Jun nucleotide sequence disclosed herein has been optimized to modify (e.g., increase or decrease) one or more of the following parameters compared to the wild-type nucleotide sequence (i.e., SEQ ID NO: 2): (i) codon adaptation index (i.e., codon usage bias), (ii) guanine-cytosine (GC) nucleotide content, and (iii) combinations thereof.

Not to be bound by any one theory, in some aspects, such codon optimization can increase the expression of the protein encoded by the nucleotide sequence. Accordingly, in some aspects, a codon-optimized c-Jun nucleotide sequence of the present disclosure is capable of increasing the expression of the encoded c-Jun protein when transfected in a cell, compared to a corresponding expression in a cell transfected with the wild-type nucleotide sequence (i.e., SEQ ID NO: 2).

In some aspects, the c-Jun polypeptide is capable of preventing and/or reducing exhaustion of a cell (e.g., anti-ROR1 CART cell) when overexpressed in the cell. Without wishing to be bound by any one theory, in some aspects, cells overexpressing c-Jun are exhaustion-resistant, thereby addressing a major barrier to progress for adoptive cellular therapy (e.g., CAR T cell therapies). In certain aspects, the resistance to exhaustion is increased by at least about 0.01-fold, at least about 0.02-fold, at least about 0.03-fold, at least about 0.04-fold, at least about 0.05-fold, at least about 0.06-fold, at least about 0.07-fold, at least about 0.08-fold, at least about 0.09-fold, at least about 0.1-fold, at least about 0.2-fold, at least about 0.3-fold, at least about 0.4-fold, at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more, compared to a reference cell (e.g., corresponding cell that does not overexpress c-Jun). In some aspects, the overexpression of the c-Jun polypeptide in an exhausted cell (e.g., immune cell) can decrease exhaustion by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%, compared to a reference cell (e.g., corresponding exhausted cell that was not modified to have increased c-Jun expression).

Overexpression of c-Jun in immune cells, such as T cells, helps sustain the active state of the cells by, e.g., alleviating or preventing T cell dysfunction (e.g., T cell exhaustion). The present engineered immune cells, such as T cells, exhibit sustained, potent cytotoxicity against ROR1-bearing tumor cells. As compared to T cells that do not overexpress c-Jun, the present engineered T cells display fewer signs of T cell exhaustion and increased signs of effector cells that can persist and function longer.

As used herein, the term "overexpression" or "overexpress" (or grammatical variants thereof) refers to an expression (at the gene level and/or protein level) which is increased compared to a reference cell. As is apparent from the present disclosure, in some aspects, cells (e.g., T cells) described herein have been modified such that they overexpress c-Jun, e.g., compared to a corresponding cell that has not been modified to overexpress c-Jun (e.g., corresponding T cells that exist in nature). In some aspects, compared to the corresponding cell, expression of the c-Jun polypeptide is increased in the cells of the present disclosure. In some aspects, compared to the corresponding cells, the expression of the c-Jun polypeptide is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more. Exemplary methods of modifying cells to overexpress c-Jun are provided elsewhere in the present disclosure.

In certain aspects, the anti-ROR1 CAR engineered cells described herein (i.e., overexpressing c-Jun) have reduced expression of one or more exhaustion markers, including but not limited to, TIGIT, PD-1, TNFRSF9, Granzyme A (GZMA), and CD39. Expression of such markers (e.g., exhaustion markers) can be measured in bulk populations by flow cytometry, using bulk RNASeq transcriptome analysis or in certain aspects, individual cell transcriptome analysis can be carried out using single cell RNASeq. In certain aspects, expression of one or more markers (e.g., exhaustion markers) in anti-ROR1 CAR engineered T cells overexpressing c-Jun is reduced by at least about 1.5-fold, at least about 2-fold, at least about 2.5-fold, at least about 3.0-fold, at least about 3.5-fold, at least about 4-fold, at least 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding anti-ROR1 CAR T cell that has not been engineered to overexpress c-Jun). In some aspects, expression of the one or more markers (e.g., exhaustion markers) in the immune cells described herein (e.g., anti-ROR1 CAR T cells overexpressing c-Jun) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the corresponding expression on the reference cell.

In certain aspects, expression of TIGIT in anti-ROR1 CAR engineered T cells overexpressing c-Jun (e.g., those described herein) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding anti-ROR1 CAR T cell that has not been engineered to overexpress c-Jun). In some aspects, expression of TIGIT in the immune cells described herein (e.g., anti-ROR1 CAR T cells overexpressing c-Jun) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the corresponding expression on the reference cell.

In certain aspects, expression of PD-1 in anti-ROR1 CAR engineered T cells overexpressing c-Jun (e.g., those described herein) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding anti-ROR1 CAR T cell that has not been engineered to overexpress c-Jun). In some aspects, expression of PD-1 in the immune cells described herein (e.g., anti-ROR1 CAR T cells overexpressing c-Jun) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the corresponding expression on the reference cell.

In certain aspects, expression of CD39 in anti-ROR1 CAR engineered T cells overexpressing c-Jun (e.g., those described herein) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding anti-ROR1 CAR T cell that has not been engineered to overexpress c-Jun). In some aspects, expression of CD39 in the immune cells described herein (e.g., anti-ROR1 CAR T cells overexpressing c-Jun) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the corresponding expression on the reference cell.

In some aspects, expression of TNFRSF9 in the immune cells described herein (e.g., anti-ROR1 CAR T cells overexpressing c-Jun) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding cell that has not been engineered to overexpress c-Jun). In some aspects, expression of TNFRSF9 in the immune cells described herein (e.g., anti-ROR1 CAR T cells overexpressing c-Jun) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the corresponding expression on the reference cell.

In some aspects, expression of GZMA in the immune cells described herein (e.g., anti-ROR1 CAR T cells overexpressing c-Jun) is reduced by at least about 1.5-fold, at least about 2-fold, at least about 2.5-fold, at least about 3.0-fold, at least about 3.5-fold, at least about 4-fold, at least about 4.5-fold, at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, or at least about 100-fold or more compared to a reference cell (e.g., corresponding cell that has not been engineered to overexpress c-Jun). In some aspects, expression of GZMA in the immune cells described herein (e.g., anti-ROR1 CAR T cells overexpressing c-Jun) is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the corresponding expression on the reference cell.

In some aspects, a population of immune cells described herein (e.g., modified to comprise a CAR, truncated EGFRt, and overexpression of a c-Jun polypeptide) comprises a reduced number of TIGIT-positive immune cells after an antigen stimulation, as compared to a reference population of corresponding cells which do not overexpress the c-Jun polypeptide. In some aspects, the number of TIGIT-positive immune cells present in the population after the antigen stimulation is reduced by at least about 30%, at least about 35%, at least about 40%, at least about 45%, at least about 50%, at least about 55%, or at least about 60%, compared to the reference population. In some aspects, the population of immune cells comprises less than about 15%, less than about 14%, less than about 13%, less than about 12%, less than about 11%, less than about 10%, less than about 9%, less than about 8%, less than about 7%, less than about 6%, or less than about 5% of TIGIT-positive immune cells after the antigen stimulation. In certain aspects, a population of engineered anti-ROR1 CAR T cells overexpressing c-Jun as described herein, has no more than about 5%, about 6%, about 7%, about 8%, about 9%, or about 10% TIGIT positive cells after 14 days of persistent antigen stimulation. In some aspects, a population of engineered anti-ROR1 CAR T cells over-expressing c-Jun as described herein, has no more than about 5%-10%, about 5%-15%, about 8%-12%, or about 8%-15% TIGIT positive cells after 14 days of persistent antigen stimulation. In this regard, % TIGIT positive cells within a population of engineered T cells such as CD4+ or CD8+ T cells can be measured using flow cytometry.

In certain aspects, a population of engineered anti-ROR1 CAR T cells overexpressing c-Jun as described herein, has no more than about, 2%, 3%, 4%, 5%, 6%, 7%, 8%, 9% or 10% PD1 positive cells after about 14 days of persistent stimulation. In some aspects, a population of engineered anti-ROR1 CAR T cells overexpressing c-Jun as described herein, has no more than about 2%-5% PD1 positive cells after 14 days of persistent antigen stimulation. In this regard, % PD1 positive cells within a population of CD4+ and/or CD8+ CAR$^+$c-Jun$^+$T cells can be measured using methods known in the art such as by flow cytometry.

In certain aspects, a population of engineered anti-ROR1 CAR T cells overexpressing c-Jun as described herein, has no more than about 20%-60% CD39 positive cells after 14 days of persistent stimulation. In some aspects, a population of engineered anti-ROR1 CAR T cells overexpressing c-Jun as described herein, has no more than about 20%-40% or 25%-45% or 30%-40% CD39 positive cells after 14 days of persistent stimulation. Percent CD39 positive cells within a population of CAR$^+$c-Jun$^+$ T cells can be measured using methods known in the art such as by flow cytometry.

In some aspects, a population of immune cells described herein (e.g., modified to comprise a CAR, truncated EGFRt, and overexpression of a c-Jun polypeptide) comprises a reduced number of TNFRSF9-positive immune cells after an antigen stimulation, as compared to a reference population of corresponding cells which do not overexpress the c-Jun polypeptide. In some aspects, the number of TNFRSF9-positive immune cells present in the population after the antigen stimulation is reduced by at least about 40%, at least about 45%, at least about 50%, at least about 55%, at least about 60%, at least about 65%, or at least about 70%, compared to the reference population. In some aspects, the population of immune cells comprises less than about 5%, less than about 4.5%, less than about 4%, less than about 3.5%, or less than about 2% of TNFRSF9-positive immune cells after the antigen stimulation.

In some aspects, a population of immune cells described herein (e.g., modified to comprise a CAR, truncated EGFRt, and overexpression of a c-Jun polypeptide) comprises a reduced number of GZMA-positive immune cells after an antigen stimulation, as compared to a reference population of corresponding cells which do not overexpress the c-Jun polypeptide. In some aspects, the number of GZMA-positive immune cells present in the population after the antigen stimulation is reduced by at least about 40%, at least about 35%, at least about 30%, at least about 25%, or at least about 20%, compared to the reference population. In some aspects, the population of immune cells comprises less than about 30%, less than about 25%, less than about 20%, less than about 15%, or less than about 10% of GZMA-positive immune cells after the antigen stimulation.

In certain aspects, a population of engineered anti-ROR1 CAR T cells overexpressing c-Jun as described herein, secretes at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, at least about 100-fold, at least about 125-fold, or at least about 150-fold more of IL-2, INF-γ, and/or TNFα as compared to a control population of T cells that do not overexpress c-Jun. In certain aspects, a population of engineered anti-ROR1 CAR T cells overexpressing c-Jun as described herein, express at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 8-fold, at least about 10-fold, at least about 15-fold, at least about 20-fold, at least about 30-fold, at least about 40-fold, at least about 50-fold, or at least about 100-fold or more IL-2, INF-γ, and/or TNFα at day 0 and/or day 14 of persistent antigen stimulation at 1:1, 1:5, 1:10 and/or 1:20

E:T ratio as compared to a control population of engineered T cells that do not overexpress c-Jun. Cytokine secretion can be measured using methods known in the art such as by ELISA or MSD analysis.

In certain aspects, a population of engineered anti-ROR1 CAR T cells overexpressing c-Jun as described herein, demonstrate at least about 2-fold, at least about 4-fold, at least about 6-fold, at least about 8-fold, at least about 10-fold, at least about 15-fold, at least about 20-fold, at least about 25-fold, at least about 30-fold, at least about 40-fold, at least about 50-fold, at least about 75-fold, at least about 100-fold, at least about 150-fold, at least about 200-fold, or at least about 250-fold or higher enhanced killing efficiency as compared to a control population of engineered T cells that do not overexpress c-Jun, for example, as quantified by area under curve (AUC).

In certain aspects, a population of engineered anti-ROR1 CAR T cells overexpressing c-Jun as described herein, demonstrate at least equal or at least about 1.5-fold, at least about 2-fold, at least about 2.5-fold, at least about 3-fold, at least about 3.5-fold, at least about 4-fold, at least about 5-fold, at least about 8-fold, at least about 10-fold, at least about 15-fold, at least about 20-fold, at least about 25-fold, at least about 30-fold, at least about 50-fold, at least about 75-fold, at least about 100-fold, at least about 125-fold, at least about 150-fold, at least about 200-fold, at least about 225-fold, at least about 250-fold, at least about 300-fold, at least about 400-fold, or at least about 500-fold or more enhanced proliferation in response to antigen as compared to a control population of engineered T cells that do not overexpress c-Jun. Antigen induced proliferation can be tested using proliferation assays known in the art, such as those described herein.

Assays useful for measuring one or more properties of a cell described herein (e.g., anti-ROR1 CAR T cell), such as exhaustion, cell phenotype, persistence, cytotoxicity and/or killing, proliferation, cytokine release, and gene expression profiles, are known in the art and include, for example, flow cytometry, intracellular cytokine staining (ICS), IncuCyte immune cell killing analysis, Meso Scale Discovery (MSD) or similar assay, persistent antigen stimulation assay, sequential antigen stimulation assay (similar to persistent antigen stimulation assay but without resetting E:T cell ratio with each round of restimulation), bulk and single cell RNAseq (see e.g., Fron Genet. 2020; 11:220; 2019 Bioinformatics 35:i436-445; 2019 Annual Review of Biomed. Data Sci. 2:139-173), cytotoxicity/killing assays, ELISA, western blot and other standard molecular and cell biology methods such as described herein or as described, for example, in Current Protocols in Molecular Biology or Current Protocols in Immunology (John Wiley & Sons, Inc., 1999-2021) or elsewhere.

EGFRt

In some aspects, a polynucleotide of the present described herein (e.g., comprising a nucleotide sequence encoding a chimeric binding protein, e.g., CAR) further comprises a nucleotide sequence encoding a truncated epidermal growth factor receptor (EGFRt). Accordingly, in certain aspects, a polynucleotide of the present disclosure encodes a chimeric polypeptide (e.g., chimeric binding protein), which comprises (i) a c-Jun polypeptide, (ii) a ROR-1 binding protein (e.g., anti-ROR1 CAR), and (iii) EGFRt.

Epidermal growth factor receptor (EGFR) is a receptor tyrosine kinase which binds ligands of the EGF family, activating several signaling cascades to convert extracellular cues into appropriate cellular responses. As used herein, "truncated epidermal growth factor receptor" or "EGFRt" comprises only a partial sequence of the full-length EGFR protein (e.g., SEQ ID NO: 3). In some aspects, the EGFRt comprises EGFR extracellular Domains III and IV and an EGFR transmembrane domain, but lacks EGFR extracellular Domains I and II and EGFR intracellular sequence.

In some aspects, the EGFRt described herein additionally comprises a juxtamembrane domain. As used herein, the term "juxtamembrane domain" refers to an intracellular portion of a cell surface protein (e.g., EGFR) immediately C-terminal to the transmembrane domain. Not to be bound by any one theory, in some aspects, the addition of the juxtamembrane domain can increase the expression of the protein encoded by the polynucleotides of the present disclosure. Accordingly, in some aspects, the EGFRt comprises the extracellular domain, the transmembrane domain, and the first three amino acids of the intracellular domain. In some aspects, the EGFRt comprises an EGFR Domain III, an EGFR Domain I, a transmembrane domain, and amino acids Arg-Arg-Arg) (SEQ ID NO: 3; see Table 3).

TABLE 3

| EGFRt amino acid sequence | |
|---|---|
| EGFRt (SEQ ID NO: 3) | RKVCNGIGIGEFKDSLSINATNIKHFKNCTSISGDLHILPVAFRGDSFTHTPPLDPQELD ILKTVKEITGFLLIQAWPENRTDLHAFENLEIIRGRTKQHGQFSLAVVSLNITSLGLRSL KEISDGDVIISGNKNLCYANTINWKKLFGTSGQKTKIISNRGENSCKATGQVCHALCSPE GCWGPEPRDCVSCRNVSRGRECVDKCNLLEGEPREFVENSECIQCHPECLPQAMNITCTG RGPDNCIQCAHYIDGPHCVKTCPAGVMGENNTLVWKYADAGHVCHLCHPNCTYGCTGPGL EGCPTNGPKIPSIATGMVGALLLLLVVALGIGLFMRRR |

As is apparent from the present disclosure, the inclusion of a nucleotide sequence encoding EGFRt provides the polynucleotides of the present disclosure (e.g., comprising a nucleotide sequence encoding a chimeric binding protein, e.g., CAR) certain advantages.

In some aspects, the EGFRt can function as a kill switch. In some aspects, when the engineered cells (e.g., anti-ROR1 CAR T cells overexpression c-Jun described herein) are no longer needed in the body, a pharmaceutical grade anti-EGFR antibody such as cetuximab, panitumumab, nimotuzumab, or necitumumab can be administered to the patient, thereby removing the engineered cells, e.g., through antibody-dependent cellular cytotoxicity (ADCC), complement-dependent cytotoxicity (CDC), and/or antibody-dependent cellular phagocytosis (ADCP).

In some aspects, the EGFRt comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 3. In certain aspects, the EGFRt comprises the amino acid sequence set forth in SEQ ID NO: 3.

Spacers

In some aspects, a polynucleotide of the present disclosure (e.g., comprising a nucleotide sequence encoding a chimeric binding protein, e.g., CAR) comprises one or more nucleotide sequences encoding a spacer. The term "spacer" as used herein refers to a polypeptide sequence which is capable of covalently linking together two spaced moieties: e.g., an antigen-binding domain and the transmembrane domain of the chimeric binding protein (e.g., CAR). In some aspects, the chimeric binding proteins (e.g., CARs) disclosed herein comprise a spacer between the antibody or antigen binding portion thereof that specifically binds to ROR1 and the transmembrane domain.

In some aspects, the spacer is derived from an immunoglobulin (e.g., derived from hinge regions or loop regions). In certain aspects, these spacers comprise, e.g., IgA1, IgA2, IgG1, IgG2, IgG3, IgG4, IgD, IgE, or IgM hinge regions, fragments thereof (alone or capped by additional sequences, e.g., $CH_1$ or $CH_2$ regions sequences), or combinations of fragments from IgA1, IgA2, IgG1, IgG2, IgG3, IgG4, IgD, IgE, or IgM hinge regions. In some aspects, the spacers comprise, e.g., IgA1, IgA2, IgG1, IgG2, IgG3, IgG4, IgD, IgE, or IgM constant domain loop regions, fragments thereof (alone or capped by additional sequences, e.g., from adjacent (3-strands), or combinations of fragments from IgA1, IgA2, IgG1, IgG2, IgG3, IgG4, IgD, IgE, or IgM loop regions. In some aspects, the spacer of the present disclosure comprise hinge region derived sequences, loop region derived sequences, or combinations thereof.

Accordingly, in some aspects, the present disclosures provide polynucleotides encoding a chimeric polypeptide (e.g., chimeric binding protein, e.g., CAR), wherein the CAR comprises (i) an antigen-binding domain (e.g., anti-ROR1 scFv), (ii) a transmembrane domain, and (iii) an intracellular domain. In certain aspects, the polynucleotide herein further encodes (iv) a c-Jun polypeptide and (v) an EGFRt peptide. In certain aspects, the polynucleotide described herein also encodes one or more spacers comprising an amino acid sequence derived from a human immunoglobulin (Ig) hinge region and/or loop region, and optionally a linker (e.g., a gly-ser rich linker), wherein the spacer is located between the antigen-binding domain and the transmembrane domain. In some aspects, the present disclosure provides a recombinant nucleic acid construct comprising a transgene encoding a CAR of the present disclosure. The present disclosure also provides a CAR encoded by one or more of the polynucleotide sequences or the vectors disclosed herein. In some aspects, the CAR of present disclosure is designed as a standard CAR, a split CAR, an off-switch CAR, an on-switch CAR, a first-generation CAR, a second-generation CAR, a third-generation CAR, a fourth-generation CAR, or a fifth generation CAR.

The terms "spacer of the present disclosure" and "Ig derived spacer" are used interchangeably to refers to
(i) a "hinge region derived spacer," i.e., a spacer comprising an amino acid sequence derived from a hinge region located between the $CH_1$ and $CH_2$ constant domains of a human immunoglobulin, e.g., IgA1, IgA2, IgG1, IgG2, IgG3, IgG4, IgD, IgE, or IgM, and optionally one or more amino acids from an adjacent $CH_1$ and/or $CH_2$ domain, or a combination thereof (e.g., several concatenated hinge region derived spacer);
(ii) a "loop region derived spacer," i.e., a spacer comprising an amino acid sequence derived from a loop region of a constant domain of a human immunoglobulin, e.g., IgA1, IgA2, IgG1, IgG2, IgG3, IgG4, IgD, IgE, or IgM, and optionally one or more amino acids from an adjacent β-strand, or a combination thereof (e.g., several concatenated loop region derived spacers); or,
(iii) a combination thereof (e.g., two or more concatenated hinge region derived spacers and loop region derived spacers).

In some aspects, the term spacer of the present disclosure refers to a subsequence of an immunoglobulin heavy chain selected the group consisting of human IgA1 (Uniprot: P01876, IGHA1_HUMAN, immunoglobulin heavy constant alpha 1; SEQ ID NO: 5), human IgA2 (Uniprot P01877, IGHA2 HUMAN, immunoglobulin heavy constant alpha 2; SEQ ID NO: 6), murine IgG2A (Uniprot P01665, GCAM MOUSE, immunoglobulin gamma 2A chain C region; SEQ ID NO: 7), human IgG1 (Uniprot P01857, IGHG1 HUMAN, immunoglobulin heavy constant gamma 1; SEQ ID NO: 8), human IgG2 (Uniprot P01859, IGHG2 HUMAN, immunoglobulin heavy constant gamma 2; SEQ ID NO: 9), human IgG3 (Uniprot P01860, IGHG3 HUMAN, immunoglobulin heavy constant gamma 3; SEQ ID NO: 10), human IgG4 (Uniprot P01861, IGHG4, immunoglobulin heavy constant gamma 4; SEQ ID NO: 11), human IgD (Uniprot P01880, IGHD HUMAN, immunoglobulin heavy constant delta; SEQ ID NO: 12), human IgE (Uniprot P01854, IGHE HUMAN, immunoglobulin heavy constant chain epsilon; SEQ ID NO: 13), or IgM (Uniprot P01871, IGHM HUMAN, immunoglobulin heavy constant mu; SEQ ID NO: 14), wherein the subsequence comprises the $CH_1$-$CH_2$ hinge region or a portion thereof. In some aspects, the subsequence further comprises an adjacent portion of a $CH_1$ and/or $CH_2$ constant domain.

In some aspects, the term spacer of the present disclosure refers to a subsequence of an immunoglobulin heavy chain selected the group consisting of human IgA1 (Uniprot: P01876, IGHA1_HUMAN, immunoglobulin heavy constant alpha 1; SEQ ID NO: 5), human IgA2 (Uniprot P01877, IGHA2 HUMAN, immunoglobulin heavy constant alpha 2; SEQ ID NO: 6), murine IgG2A (Uniprot P01665, GCAM MOUSE, immunoglobulin gamma 2A chain C region; SEQ ID NO: 7), human IgG1 (Uniprot P01857, IGHG1 HUMAN, immunoglobulin heavy constant gamma 1; SEQ ID NO: 8), human IgG2 (Uniprot P01859, IGHG2 HUMAN, immunoglobulin heavy constant gamma 2; SEQ ID NO: 9), human IgG3 (Uniprot P01860, IGHG3 HUMAN, immunoglobulin heavy constant gamma 3; SEQ ID NO: 10), human IgG4 (Uniprot P01861, IGHG4, immunoglobulin heavy constant gamma 4; SEQ ID NO: 11), human IgD (Uniprot P01880, IGHD HUMAN, immunoglobulin heavy constant delta; SEQ ID NO: 12), human IgE (Uniprot P01854, IGHE HUMAN, immunoglobulin heavy constant chain epsilon; SEQ ID NO: 13), or IgM (Uniprot P01871, IGHM HUMAN, immunoglobulin heavy constant mu; SEQ ID NO: 14), wherein the subsequence comprises a loop region from a constant domain or a portion thereof. In some aspects, the subsequence further comprises an adjacent portion of a β-strand.

In some aspects, a CAR spacer of the present disclosure comprises, consists, or consists essentially of a sequence of an IgG2 hinge, e.g., a murine IgG2A hinge, derived CAR spacer, e.g., Spacer 1, e.g., KPCPPCKCP (SEQ ID NO: 15).

In some aspects, a spacer of the present disclosure has at least about 70%, at least about 75%, at least about 80%, at least about 85%, at least about 90%, at least about 95%, at least about 96%, at least about 97%, at least about 98%, or at least about 99% sequence identity to a sequence set forth in SEQ ID NO: 15. In some aspects, a CAR spacer of the present disclosure comprises a sequence identical to any one of the sequences set forth in SEQ ID NO: 15 except for one, 2, 3, 4, 5, 6, 7, 8, 9, or 10 amino acid substitutions. In some aspects, the amino acid substitutions are conservative amino acid substitutions. In some aspects, the amino acid substitution comprises at least one non-conservative amino acid substitution.

In some aspects, a spacer of the present disclosure comprises of the sequence set forth in SEQ ID NO: 15, wherein the spacer sequence further comprises an optional flexible linker (e.g., the linker of GGGSG (SEQ ID NO: 16)). Thus, in some aspects, a spacer of the present disclosure comprises a spacer sequence (e.g., SEQ ID NO: 15) and an optional C-terminal or N-terminal flexible linker. In some aspects, any optional flexible linkers (e.g., gly/ser rich linker) disclosed herein can be appended to the C-terminus and/or the N-terminus of a spacer.

Accordingly, in some aspects, a polynucleotide of the present disclosure comprises a nucleotide sequence encoding a chimeric binding protein (e.g., CAR), which comprises (i) a ROR1-binding protein; (ii) a spacer; and (iii) a nucleotide encoding a EGFRt. In some aspects, the polynucleotide comprises a CAR comprising (i) a ROR1-binding protein comprising a heavy chain variable region (VH) comprising CDR1, CDR2, and CDR3 of the R12 antibody and a light chain variable region (VL) comprising CDR1, CDR2, and CDR3 of the R12 antibody; (ii) a spacer comprising the amino acid sequence as set forth in SEQ ID NO: 15; and (iii) a nucleotide sequence encoding a truncated EGF receptor (EGFRt). As further described elsewhere in the present disclosure, in some aspects, the VH of the ROR1 binding portion comprises SEQ ID NO: 44 and the VL of the ROR1 binding portion comprises SEQ ID NO: 48. In some aspects, the EGFRt comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 3.

Signal Peptides

As described herein, in some aspects, a polynucleotide of the present disclosure (e.g., comprising a nucleotide sequence encoding a chimeric binding protein, e.g., CAR) also comprises a nucleotide sequence encoding a signal peptide. The signal peptide can facilitate the cell surface expression of the encoded protein and then can be subsequently cleaved from the mature protein.

Any suitable signal peptide known in the art can be used with the present disclosure. Non-limiting examples of signal peptides are provided in Table 4 (below). In certain aspects, the signal peptide is derived from human Ig kappa. In some aspects, the signal peptide comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 17 (MVLQTQVFISLLLWISGAYG). In certain aspects, the signal peptide comprises the amino acid sequence set forth in SEQ ID NO: 17 (MVLQTQVFISLLL-WISGAYG). In some aspects, the signal peptide is derived from GM-CSF. In certain aspects, such a signal peptide comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 18 (MLLLVTSLLL-CELPHPAFLLIP). In some aspects, the signal peptide comprises the amino acid sequence set forth in SEQ ID NO: 18 (MLLLVTSLLLCELPHPAFLLIP).

In some aspects, a polynucleotide described herein comprises a single signal peptide (e.g., SEQ ID NO: 17 or 18). In some aspects, the polynucleotide comprises multiple signal peptides (e.g., at least two, three, four, or more). In certain aspects, a polynucleotide described herein encodes a chimeric polypeptide (e.g., chimeric binding protein, e.g., CAR) wherein the CAR comprises (i) an antigen-binding domain (e.g., anti-ROR1 scFv), (ii) a transmembrane domain, and (iii) an intracellular domain. In certain aspects the polynucleotide herein further encodes (iv) a c-Jun polypeptide and (v) an EGFRt polypeptide. In certain aspects, the polynucleotides herein also encode one or more signal peptides (e.g., those set forth in Table 4).

TABLE 4

Signal Peptide Sequences

| Source | Sequence |
|---|---|
| EGFR | MRPSGTAGAALLALLAALCPASRA (SEQ ID NO: 19) |
| GM-CSF | MLLLVTSLLLCELPHPAFLLIP (SEQ ID NO: 18) |
| human ig kappa | MVLQTQVFISLLLWISGAYG (SEQ ID NO: 17) |
| human CD33 | MPLLLLLPLLWAGALA (SEQ ID NO: 20) |

Linkers

In some aspects, any CAR spacer of the present can comprise an optional N-terminal linker and/or an optional C-terminal linker. In some aspects, the linker can link any components of the CAR described herein. Flexible linker sequences known the art can be used as optional linkers. In some aspects, the optional linker is a glycine/serine linker according to the formula [(Gly)n-Ser]m (SEQ ID NO: 21) where n is any integer from 1 to 100 and m is any integer from 1 to 100. In some aspects, the glycine/serine linker is according to the formula [(Gly)x-(Ser)y]z (SEQ ID NO: 22) wherein x in an integer from 1 to 4, y is 0 or 1, and z is an integers from 1 to 50. In some aspects, the optional linker comprises the sequence (G)n (SEQ ID NO: 23), where n can be an integer from 1 to 100. In some aspects, the optional linker can comprise the sequence (GlyAla)n (SEQ ID NO: 24), wherein n is an integer between 1 and 100.

In some aspects, the sequence of the optional linker is GGGG (SEQ ID NO: 25). In some aspects, the sequence of the optional linker is GGGSG (SEQ ID NO: 26).

In some aspects, the optional linker comprises the sequence (GGGSG)n (SEQ ID NO: 27). In some aspects, the optional linker comprises the sequence (GGGGS)n (SEQ ID NO:28). In some aspects, the optional linker can comprise the sequence (GGGS)n (SEQ ID NO: 29). In some aspects, the optional linker can comprise the sequence (GGS)n (SEQ ID NO: 30). In these instances, n can be an integer from 1 to 100. In other instances, n can be an integer from one to 20, i.e., 1, 2, 3, 4, 5, 6, 7, 8, 9, 10, 11, 12, 13, 14, 15, 16, 17, 18, 19, or 20. In some aspects n is an integer from 1 to 100.

Examples of the optional linker include, but are not limited to, e.g., GSGSGS (SEQ ID NO: 31), GGSGG (SEQ ID NO: 32), SGGSGGS (SEQ ID NO: 33), GGSGGSGGSGGSGGG (SEQ ID NO: 34), GGSGGSGGGGSGGGS (SEQ ID NO: 35), GGSGGSGGSGGSGGS (SEQ ID NO: 63), or GGGGSGGGGSGGGGS (SEQ ID NO: 36).

In some aspects, the optional linker comprises the sequence PGG. In some aspects, the optional linker comprises additional amino acids in addition to Glycine and Serine. In some aspects, the optional linker comprises 1, 2, 3, 4, or 5 non-gly/non-ser amino acids. In some aspects, the Gly/Ser-linker comprises at least about 60%, at least about 65%, at least about 70%, at least about 80%, at least about 85%, at least about 90%, or at least 95% glycine or serine amino acids.

In some specific aspects, the optional linker is between 1 and 10 amino acids in length. In some aspects, the optional linker as between about 5 and about 10, between about 10 and about 20, between about 20 and about 30, between about 30 and about 40, between about 40 and about 50, between about 50 and about 60, between about 60 and about 70, between about 70 and about 80, between about 80 and about 90, or between about 90 and about 100 amino acids in length.

In some aspects, the linker is a non-cleavable linker, such that the linker and the different components of a polynucleotide provided herein (e.g., c-Jun and chimeric binding protein) are expressed as a single polypeptide. In certain aspects, the linker is a cleavable linker. As used herein, the term "cleavable linker" refers to a linker that comprises a cleavage site, such that when expressed can be selectively cleaved to produce two or more products. In some aspects, the linker is selected from a P2A linker, a T2A linker, an F2A linker, an E2A linker, a furin cleavage site, or any combination thereof (see Table 5 below). In some aspects, the linker further comprises a GSG linker sequence. In some aspects, a linker useful for the present disclosure comprises an Internal Ribosome Entry Site (IRES), such that separate polypeptides encoded by the first and second genes are produced during translation. Additional description of linkers that can be used with the present disclosure are provided, e.g., in WO 2020/223625 A1 and US 2019/0276801 A1, each of which is incorporated herein by reference in its entirety.

TABLE 5

| | Linker Sequences |
|---|---|
| P2A | ATNFSLLKQAGDVEENPGP (SEQ ID NO: 37) |
| T2A | EGRGSLLTCGDVEENPGP (SEQ ID NO: 38) |
| F2A | VKQTLNFDLLKLAGDVESNPGP (SEQ ID NO: 39) |
| E2A | QCTNYALLKLAGDVESNPGP (SEQ ID NO: 40) |
| Furin Cleavage Site | RAKR (SEQ ID NO: 41) |

In some aspects, the linker comprises a P2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 37. In some aspects, the linker comprises the amino acid sequence set forth in SEQ ID NO: 37.

In some aspects, the linker comprises a T2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 38. In some aspects, the linker comprises the amino acid sequence set forth in SEQ ID NO: 38.

In some aspects, the linker comprises an F2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 39. In some aspects, the linker comprises the amino acid sequence set forth in SEQ ID NO: 39.

In some aspects, the linker comprises an E2A linker. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 40. In some aspects, the linker comprises the amino acid sequence set forth in SEQ ID NO: 40.

In some aspects, the linker comprises an amino acid sequence comprising a furin cleavage site. In some aspects, the linker comprises an amino acid sequence having at least about 80%, at least about 85%, at least about 90%, at least about 95%, at least about 96%, at least about 97%, at least about 98%, or at least about 99% sequence identity to the amino acid sequence set forth in SEQ ID NO: 41. In some aspects, the linker comprises the amino acid sequence set forth in SEQ ID NO: 41.

Antigen-Binding Domains

In some aspects, the antigen-binding domain of a chimeric binding protein (e.g., CAR) encoded by a polynucleotide of the present disclosure comprises an Ig NAR, a Fab, a Fab', a F(ab)'2, a F(ab)'3, an Fv, a single chain variable fragment (scFv), a bis-scFv, a (scFv)2, a minibody, a diabody, a triabody, a tetrabody, an intrabody, a disulfide stabilized Fv protein (dsFv), a unibody, or a nanobody. In certain aspects, the antigen-binding domain is scFv. In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of, e.g., at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence can comprise any naturally occurring amino acid. In some aspects, the linker sequence comprises amino acids glycine and serine. In some aspects, the linker sequence comprises sets of glycine and serine repeats such as $(Gly_4Ser)n$, where n is a positive integer equal to or greater than 1 (SEQ ID NO: 42). In some aspects, the linker can be $(Gly_4Ser)4$ (SEQ ID NO: 43) or $(Gly_4Ser)_3$ (SEQ ID NO: 36), or any gly-ser rich linker disclosed above.

Variation in the linker length can retain or enhance activity, giving rise to superior efficacy in activity studies.

In some aspects, the amino acid sequence of the antigen-binding domain or other portions or the entire CAR can be modified, e.g., an amino acid sequence described herein can be modified, e.g., by a conservative substitution. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

An exemplary anti-ROR1 CAR is described in Hudecek, et al. Clin. Cancer Res. 19.12(2013):3153-64, incorporated herein by reference in its entirety. In some aspects, a CAR T cell of the present disclosure comprising an anti-ROR1 CAR is generated as described in Hudecek et al. (for example, as described in Hudecek et al. at page 3155, first full paragraph, incorporated herein by reference in its entirety), wherein the spacer disclosed in Hudecek has been replaced by a CAR spacer of the present disclosure. In some aspect, an anti-ROR1 CAR of the present disclosure includes an antibody or fragment thereof comprising the VH and/or VL sequences of the 2A2, R11, and R12 anti-ROR1 monoclonal antibodies described in Hudecek et al. at paragraph bridging pages 3154-55; Baskar et al. MAbs 4(2012): 349-61; and Yang et al. PLoS ONE 6(2011):e21018, incorporated herein by reference in their entirety.

In some aspects, an antigen-binding domain of the present disclosure is capable of cross-competing with an anti-ROR1 antibody, e.g., R12, antibody. The R12 antibody sequences are shown in TABLE 6. In some aspects, the antigen-binding domain useful for the present disclosure binds to the same epitope of the R12 antibody. As will be apparent to those skilled in the arts, any anti-ROR1 antibody known in the art can be used with the present disclosure. Non-limiting examples of such antibodies include the 2A2 and R11 antibodies described in Hudecek, et al. Clin. Cancer Res. 19.12(2013):3153-64; Baskar et al. MAbs 4(2012):349-61; and Yang et al. PLoS ONE 6(2011):e21018; U.S. Pat. No. 9,316,646 B2; and U.S. Pat. No. 9,758,586 B2; each of which is incorporated herein by reference in its entirety.

TABLE 6

R12 antibody CDRs

| | |
|---|---|
| R12 VH (SEQ D NO: 44) | QEQLVESGGRLVTPGGSLTLSCKASGFDFSAYYMSWVRQAPGKGLEWIATIYPSSGK TYYATWVNGRFTISSDNAQNTVDLQMNSLTAADRATYFCARDSYADDGALFNIWGPG TLVTISS |
| R12 VH CDR1 (SEQ ID NO: 45) | AYYMS |
| R12 VH CDR2 (SEQ ID NO: 46) | TIYPSSGKTYYATWVNG |
| R12 VH CDR3 (SEQ ID NO: 47) | DSYADDGALFNI |
| R12 VL (SEQ ID NO: 48) | ELVLTQSPSVSAALGSPAKITCTLSSAHKTDTIDWYQQLQGEAPRYLMQVQSDGSYT KRPGVPDRFSGSSSGADRYLIIPSVQADDEADYYCGADYIGGYVFGGGTQLTVTG |
| R12 VL CDR1 (SEQ ID NO: 49) | TLSSAHKTDTID |
| R12 VL CDR2 (SEQ ID NO: 50) | GSYTKRP |
| R12 VL CDR3 (SEQ ID NO: 51) | GADYIGGYV |

In some aspects, the antigen-binding domain of the present disclosure comprises VH CDR3 of the R12 antibody. In some aspects, the antigen-binding domain of the present disclosure comprises VH CDR1, VH CDR2 and VH CDR3 of the R12 antibody. In some aspects, the antigen-binding domain of the present disclosure comprises VH CDR1, VH CDR2, VH CDR3, VL CDR1, VL CDR2, and VL CDR3 of the R12 antibody. In some aspects, the antigen-binding domain of the present disclosure, e.g., R12 scFv, comprises the VH and the VL of the R12 antibody. In some aspects, the R12 scFv is linked to a transmembrane domain by an IgG2 linker, e.g., Spacer 1 (SEQ ID NO: 15), and optionally a linker of SEQ ID NO: 16.

In some aspects, the ROR1-binding antibody or antigen binding portion thereof comprises an amino acid sequence having at least about 60%, at least about 70%, at least about 80%, at least about 90%, at least about 95%, at least about 96%, at least about 97%, at least about 98%, at least about 99%, or about 100% sequence identity to SEQ ID NO: 52.

In some aspects, a CAR of the present disclosure targeting ROR1 includes an antibody or fragment thereof (e.g., single chain variable fragment (scFv)) that targets ROR1, including those described in U.S. Pat. No. 9,316,646B2, issued Sep. 12, 2017, or U.S. 9,758,586B2, issued Apr. 19, 2016, each of which is incorporated herein by reference in its entirety.

In some aspects, a CAR of the present disclosure comprises an antigen-binding domain, a transmembrane domain, and an intracellular domain, wherein the antigen-binding domain and the transmembrane domain are linked by a CAR spacer comprising KPCPPCKCP (SEQ ID NO: 15) and optionally a linker of SEQ ID NO: 16, and wherein the antigen-binding domain comprises VH CDR1, VH CDR2, VH CDR3, VL CDR1, VL CDR2, and VL CDR3 of the R12 antibody, e.g., VH and VL of the R12 antibody.

In some aspects, anti-ROR1 antigen-binding antibody fragments (e.g., scFvs) are conjugated or fused to a biologically active molecule, e.g., to form a CAR of the present disclosure that directs immune cells, e.g., T cells to respond to ROR1-expressing cells.

In some aspects, a chimeric antigen receptor (CAR) of the present disclosure (i.e., anti-ROR1 CAR overexpressing c-Jun) includes an anti-ROR1 monoclonal antibody called UC-961 (Cirmtuzumab) o an antigen-binding portion thereof. See, e.g., Clinical Trial Identifier No. NCT02222688. Cirmtuzumab can be used to treat cancers, such as chronic lymphocytic leukemia (CLL), ovarian cancer, and melanoma. See, e.g., Hojjat-Farsangi et al. PLoS One. 8(4): e61167; and NCT02222688.

Signaling, Transmembrane, Costimulatory Domains

In some aspects, the intracellular domain of a chimeric binding protein (e.g., CAR) encoded by a polynucleotide of the present disclosure comprises a signaling domain, such as that derived from CD3 zeta, FcR gamma, FcR beta, CD3 gamma, CD3 delta, CD3 epsilon, CD5, CD22, CD79a, CD79b, or CD66d. In some aspect, the CAR further comprises a co-stimulatory domain, such as that derived from 2B4, HVEM, ICOS, LAG3, DAP10, DAP12, CD27, CD28, 4-1BB (CD137), OX40 (CD134), CD30, CD40, ICOS (CD278), glucocorticoid-induced tumor necrosis factor receptor (GITR), lymphocyte function-associated antigen-1 (LFA-1), CD2, CD7, LIGHT, NKG2C, or B7-$H_3$. In some aspects, the CAR comprises a 4-1BB costimulatory domain. In some aspects, the 4-1BB costimulatory domain comprises the sequence set forth in SEQ ID NO: 53.

In some aspects, the chimeric binding protein (e.g., CAR) encoded by a polynucleotide of the present disclosure comprises a transmembrane domain (TM), such as that selected from the group consisting of the alpha, beta or zeta chain of the T-cell receptor, CD28, CD3 epsilon, CD45, CD2, CD4, CD5, CD8, CD9, CD16, CD22, CD33, CD37, CD45, PD1, CD64, CD80, CD86, CD134, CD137, CD152, and CD154. The transmembrane domain can be derived either from a natural or from a recombinant source. Where the source is natural, the domain can be derived from any membrane-bound or transmembrane protein. In some aspects, the transmembrane domain is capable of signaling to the intracellular domain(s) whenever the CAR of the present disclosure has bound to a target.

In some aspects, a transmembrane domain can include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, $IL_2R$ beta, $IL_2R$ gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, or CD19.

In some aspects, the TM domain is derived from CD8a, CD2, CD4, CD28, CD45, PD1, CD152, or any combination thereof. In some aspects, the TM domain is derived from CD28. In some aspects, the TM domain comprises an amino acid sequence having at least about 60%, at least about 70%, at least about 80%, at least about 90%, at least about 95%, at least about 96%, at least about 97%, at least about 98%, or at least about 99% sequence identity to SEQ ID NO: 54.

In certain aspects, the TM domain comprises the amino acid sequence set forth in SEQ ID NO: 54.

In some aspects, the chimeric binding protein (e.g., CAR) encoded by a polynucleotide of the present disclosure further comprises a sequence encoding a costimulatory domain, e.g., a costimulatory domain described herein. In some aspects, the costimulatory domain comprises a costimulatory domain of interleukin-2 receptor (IL-2R), interleukin-12 receptor (IL-12R), IL-7, IL-21, IL-23, IL-15, CD2, CD3, CD4, CD7, CD8, CD27, CD28, CD30, CD40, 4-1BB/CD137, ICOS, lymphocyte function-associated antigen-1 (LFA-1), LIGHT, NKG2C, OX40, DAP10, B7-$H_3$, CD28 deleted for Lck binding (ICA), BTLA, GITR, HVEM, LFA-1, LIGHT, NKG2C, PD-1, TILR2, TILR4, TILR7, TILR9, Fc receptor gamma chain, Fc receptor c chain, a ligand that specifically binds with CD83, or any combination thereof.

In some aspects, the chimeric binding protein (e.g., CAR) of the present disclosure (e.g., anti-ROR1 CAR) further comprises a sequence encoding an intracellular signaling domain, e.g., an intracellular signaling domain described herein. In some aspects, the intracellular signaling domain comprises a CD3ζ activating domain, a CD3δ activating domain, a CD3ε activating domain, a CD3η activating domain, a CD79A activating domain, a DAP 12 activating domain, a FCER1G activating domain, a DAP10/CD28 activating domain, a ZAP70 activating domain, or any combination thereof. In some aspects, the intracellular signaling domain comprises a CD3 activating domain. In some aspects, the CD3 ζ activating domain comprises an amino acid sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 55. In certain aspects, the intracellular signaling domain comprises the sequence set forth in SEQ ID NO: 55.

In some aspects, the transmembrane domain of a chimeric binding protein (e.g., CAR) of the present disclosure (e.g., a CAR targeting ROR1) comprises a transmembrane domain is which linked to the intracellular domain of the chimeric binding protein (e.g., CAR) by a linker.

In some aspects, the intracellular signaling domain comprises a 4-1BB co-stimulatory domain. In some aspects, the 4-1BB co-stimulatory domain comprises an amino acid sequence having at least about 70%, at least about 75%, at least about 80%, at least about 85%, at least about 90%, at least about 95%, at least about 96%, at least about 97%, at least about 98%, or at least about 99% sequence identity to SEQ ID NO: 53. In certain aspects, the 4-1BB co-stimulatory domain comprises the sequence set forth in SEQ ID NO: 53.

As is apparent from the above disclosure, in some aspects, a polynucleotide described herein comprises (from 5' to 3') (i) a first nucleotide sequence encoding a c-Jun polypeptide, (ii) a second nucleotide sequence encoding a first linker (e.g., P2A linker), (iii) a third nucleotide sequence encoding a first signal peptide (e.g., hIgκ), (iv) a fourth nucleotide sequence encoding an antigen-binding domain (e.g., anti-ROR1 scFv), (v) a fifth nucleotide sequence encoding a second linker (e.g., GGGSG; SEQ ID NO: 16), (vi) a sixth nucleotide sequence encoding a spacer (e.g., IgG2 hinge derived spacer), (vii) a seventh nucleotide sequence encoding a transmembrane domain (e.g., CD28), (viii) an eighth nucleotide sequence encoding a costimulatory domain (e.g., 4-1BB), (ix) a ninth nucleotide sequence encoding an intracellular signaling domain (e.g., CD3), (x) a tenth nucleotide sequence encoding a third linker (e.g., P2A linker), (xi) an eleventh nucleotide sequence encoding a second signal peptide (e.g., GMCSFRaSP), and (xii) a twelfth nucleotide sequence encoding a EGFRt.

Bispecific CARs

In some aspects, the CARs of the present disclosure are bispecific CARs. Accordingly, in some aspects, the polynucleotide encoding a CAR of the present disclosure encodes at least a polypeptide of a bispecific CAR (e.g., a CAR targeting a first antigen and second antigen).

In some aspects, the antigen-binding domain of a CAR of the present disclosure is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In some aspects, the first and second epitopes are on the same antigen, e.g., the same protein (or subunit of a multimeric protein). In some aspects, the first and second epitopes overlap. In some aspects, the first and second epitopes do not overlap. In some aspects, the first and second epitopes are on different antigens, e.g., different proteins (or different subunits of a multimeric protein).

In some aspects, a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In some aspects, a bispecific antibody molecule comprises a half antibody having binding specificity for a first epitope and a half antibody having binding specificity for a second epitope. In some aspects, a bispecific antibody molecule comprises a half antibody, or fragment thereof, having binding specificity for a first epitope and a half antibody, or fragment thereof, having binding specificity for a second epitope. In some aspects, a bispecific antibody molecule comprises a scFv, or fragment thereof, have binding specificity for a first epitope and a scFv, or fragment thereof, have binding specificity for a second epitope.

In certain aspects, the antibody molecule is a multispecific (e.g., a bispecific or a trispecific) antibody molecule. Protocols for generating bispecific or heterodimeric antibody molecules are known in the art.

Within each antibody or antigen-binding antibody fragment (e.g., scFv) of a bispecific antibody molecule, the VH can be upstream or downstream of the VL. In some aspects, the upstream antibody or antibody fragment (e.g., scFv) is arranged with its VH (VH$_1$) upstream of its VL (VL$_1$) and the downstream antibody or antibody fragment (e.g., scFv) is arranged with its VL (VL$_2$) upstream of its VH (VH$_2$), such that the overall bispecific antibody molecule has the arrangement VH$_1$-VL$_1$-VL$_2$-VH$_2$. In some aspects, the upstream antibody or antibody fragment (e.g., scFv) is arranged with its VL (VL$_1$) upstream of its VH (VH$_1$) and the downstream antibody or antibody fragment (e.g., scFv) is arranged with its VH (VH$_2$) upstream of its VL (VL$_2$), such that the overall bispecific antibody molecule has the arrangement VL$_1$-VH$_1$-VH$_2$-VL$_2$. Optionally, a linker is disposed between the two antibodies or antibody fragments (e.g., scFvs), e.g., between VL$_1$ and VL$_2$ if the construct is arranged as VH$_1$-VL$_1$-VL$_2$-VH$_2$, or between VH$_1$ and VH$_2$ if the construct is arranged as VL$_1$-VH$_1$-VH$_2$-VL$_2$. The linker can be a linker as described herein, e.g., a (Gly$_4$Ser)n linker, wherein n is 1, 2, 3, 4, 5, or 6, e.g., 4 (SEQ ID NO: 43). In general, the linker between the two scFvs should be long enough to avoid mispairing between the domains of the two scFvs. Optionally, a linker is disposed between the VL and VH of the first scFv. Optionally, a linker is disposed between the VL and VH of the second scFv. In constructs that have multiple linkers, any two or more of the linkers can be the same or different. Accordingly, in some aspects, a bispecific CAR comprises VLs, VHs, and optionally one or more linkers in an arrangement as described herein.

In some aspects, the antibody molecule is a bispecific antibody molecule having a first epitope located on a first tumor antigen (e.g., ROR1) and a second epitope located on a second antigen, e.g., CD10, CD19, CD20, CD22, CD34, CD123, FLT-3, ROR1, CD79b, CD179b, or CD79a. In some aspects, the bispecific antibody binds to a first epitope, wherein the first epitope is located on CD19, and to a second epitope, wherein the second epitope is located on CD20. In some aspects, the bispecific antibody binds to a first epitope, wherein the first epitope is located on CD19, and to a second epitope, wherein the second epitope is located on CD22. In some aspects, the bispecific antibody binds to a first epitope, wherein the first epitope is located on CD20, and to a second epitope, wherein the second epitope is located on CD22. In certain aspects, the antibody molecule is a bispecific antibody molecule having a first binding specificity for a first B-cell epitope and a second binding specificity for another B-cell antigen. For instance, in some aspects the bispecific antibody molecule has a first binding specificity for a first B-cell epitope, e.g., for ROR1, and a second binding specificity for one or more of CD10, CD19, CD20, CD22, CD34, CD123, FLT-3, ROR1, CD79b, CD179b, or CD79a B-cell epitopes.

In some aspects, the second antigen is selected from the group consisting of ROR1, HER2, AFP, CD19, TRAC, TCRβ, BCMA, CLL-1, CS1, CD38, CD19, TSHR, CD123, CD22, CD30, CD70, CD171, CD33, EGFRvIII, GD2, GD3, Tn Ag, PSMA, ROR2, GPC1, GPC2, FLT3, FAP, TAG72, CD44v6, CEA, EPCAM, B7H$_3$, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gplOO, bcr-abl, tyrosinase, EphA2, Fucosyl GM1, sLe, GM3, TGSS, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WTI, NY-ESO-1, LAGE-1a, MAGE-A1, legumain, HPV E6,E7, MAGE Al, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin Bl, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3ε, CD4, CD5, CD7, the extracellular portion of the APRIL protein, and any combinations thereof.

Inducible Expression Constructs

In some aspects, the expression of a polycistronic polynucleotide herein encoding a CAR (e.g., anti-ROR1 CAR), c-Jun, and/or EGFRt as described herein is regulated by a constitutive promoter, e.g., immediate early cytomegalovirus (CMV) promoter, Elongation Growth Factor-1α (EF-1α), simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, ubiquitin promoter, the myosin promoter, the hemoglobin promoter, and the creatine kinase promoter. However, the regulation of the expression of polypeptides encoded by the polynucleotide (e.g., an anti-ROR1 CAR, c-Jun, and/or EGFRt) of the present disclosure is not limited to the use of a constitutive promoter.

Thus, in some aspects, the expression of the proteins encoded by the polynucleotides described herein (e.g., the anti-ROR1 CARs, c-Jun, EGFRt proteins, signal peptides, and/or spacers) is inducible. The term "inducible" refers to the presence of an "inducible promoter," i.e., a nucleotide sequence which, when operably linked with a polynucleotide which encodes or specifies a gene product, e.g., a CAR, c-Jun, EGFRt of the present disclosure, causes the gene product to be produced in a cell substantially only when an inducer which corresponds to the promoter is present in the cell. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some aspects, a polynucleotide encoding a CAR, c-Jun, and/or EGFRt of the present disclosure comprises a "tissue-specific" promoter, i.e., a nucleotide sequence which, when operably linked with a polynucleotide which encodes or specifies a gene product, e.g., a CAR of the present disclosure, causes the gene product(s) to be produced in a cell substantially only if the cell is a cell of the tissue type corresponding to the promoter.

Vectors

The present disclosure also provides a vector comprising a polynucleotide encoding an anti-ROR1 CAR, a c-Jun, and an EGFRt protein of the present disclosure (i.e., a c-Jun-anti-ROR1 CAR construct) operably linked to a regulatory element. In some aspects, the polycistronic polynucleotide encoding a CAR, c-Jun, EGFRt of the present disclosure is a DNA molecule, or a RNA molecule.

In some aspects, the vector is a transfer vector. The term "transfer vector" refers to a composition of matter which comprises an isolated nucleic acid (e.g., a polynucleotide of the present disclosure) and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

In some aspects, the vector is an expression vector. The term "expression vector" refers to a vector comprising a recombinant polynucleotide (e.g., a polypeptide of the present disclosure) comprising expression control sequences operatively linked to a nucleotide sequence to be expressed. In some aspects, an expression vector is a polycistronic expression vector. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

In some aspects, the vector is a viral vector, a mammalian vector, or bacterial vector. In some aspects, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector.

In some aspects, the adenoviral vector is a third generation adenoviral vector. ADEASY™ is by far the most popular method for creating adenoviral vector constructs. The system consists of two types of plasmids: shuttle (or transfer) vectors and adenoviral vectors. The transgene of interest is cloned into the shuttle vector, verified, and linearized with the restriction enzyme PmeI. This construct is then transformed into ADEASIER-1 cells, which are BJ5183 E. coli cells containing PADEASY™. PADEASY™ is a ~33 Kb adenoviral plasmid containing the adenoviral genes necessary for virus production. The shuttle vector and the adenoviral plasmid have matching left and right homology arms which facilitate homologous recombination of the transgene into the adenoviral plasmid. One can also co-transform standard BJ5183 with supercoiled PADEASY™ and the shuttle vector, but this method results in a higher background of non-recombinant adenoviral plasmids. Recombinant adenoviral plasmids are then verified for size and proper restriction digest patterns to determine that the transgene has been inserted into the adenoviral plasmid, and that other patterns of recombination have not occurred. Once verified, the recombinant plasmid is linearized with PacI to create a linear dsDNA construct flanked by ITRs. 293 or 911 cells are transfected with the linearized construct, and virus can be harvested about 7-10 days later. In addition to this method, other methods for creating adenoviral vector constructs known in the art at the time the present application was filed can be used to practice the methods disclosed herein.

In some aspects, the viral vector is a retroviral vector, e.g., a lentiviral vector (e.g., a third or fourth generation lentiviral vector). The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that can be used in the clinic, include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

Lentiviral vectors are usually created in a transient transfection system in which a cell line is transfected with three separate plasmid expression systems. These include the transfer vector plasmid (portions of the HIV provirus), the packaging plasmid or construct, and a plasmid with the heterologous envelop gene (env) of a different virus. The three plasmid components of the vector are put into a packaging cell which is then inserted into the HIV shell. The virus portions of the vector contain insert sequences so that the virus cannot replicate inside the cell system. Current third generation lentiviral vectors encode only three of the nine HIV-1 proteins (Gag, Pol, Rev), which are expressed from separate plasmids to avoid recombination-mediated generation of a replication-competent virus. In fourth generation lentiviral vectors, the retroviral genome has been further reduced (see, e.g., TAKARA® LENTI-X™ fourth-generation packaging systems).

In some aspects, the present disclosure comprises a lentiviral vector comprising a polynucleotide sequence encoding: (i) R12 scFv comprising SEQ ID NO: 52; (ii) a c-Jun polypeptide; (iii) a truncated EGF receptor (EGFRt).

In some aspects, the present disclosure comprises a vector (e.g., lentiviral vector) comprising a polynucleotide sequence encoding: (i) R12 scFv comprising SEQ ID NO: 52; (ii) a c-Jun polypeptide; (iii) a truncated EGF receptor (EGFRt); (iv) a transmembrane domain; (v) an intracellular signaling domain; (vi) an intracellular co-stimulatory signaling region. In some aspects, the vector (e.g., lentiviral vector) comprises a spacer between the antibody or antigen binding portion thereof that specifically binds to ROR1 and the TM domain. In some aspects, the vector (e.g., lentiviral vector) comprises the spacer which further comprises a linker. In some aspects, the vector (e.g., lentiviral vector) comprises a polynucleotide sequence encoding a linker in between the c-Jun polypeptide and the CAR peptide. In some aspects, the vector (e.g., lentiviral vector) comprises a polynucleotide sequence encoding a linker in between the CAR peptide and the EGFRt peptide. Accordingly, in certain aspects, a vector described herein comprises a polynucleotide, which comprises (from 5' to 3') (i) a first nucleotide sequence encoding a c-Jun polypeptide, (ii) a second nucleotide sequence encoding a first linker (e.g., P2A linker), (iii) a third nucleotide sequence encoding a signal peptide (e.g., hIgx), (iv) a fourth nucleotide sequence encoding an antigen-binding domain (e.g., anti-ROR1 scFv), (v) a fifth nucleotide sequence encoding a second linker (e.g., GGGSG; SEQ ID NO: 16), (vi) a sixth nucleotide sequence encoding a spacer (e.g., IgG2 hinge derived spacer), (vii) a seventh nucleotide sequence encoding a transmembrane domain (e.g., CD28), (viii) an eighth nucleotide sequence encoding a costimulatory domain (e.g., 4-1BB), (ix) a ninth nucleotide sequence encoding an intracellular signaling domain (e.g., CD3), (x) a tenth nucleotide sequence encoding a third linker (e.g., P2A linker), (xi) an eleventh nucleotide sequence encoding a signal peptide (e.g., GMCSFRaSP), and (xii) a twelfth nucleotide sequence encoding a EGFRt.

In some aspects, non-viral methods can be used to deliver a nucleic acid comprising a polynucleotide encoding a CAR and other polypeptides of the present disclosure into a cell or tissue of a subject. In some aspects, the non-viral method includes the use of a transposon. In some aspects, use of a non-viral method of delivery permits reprogramming of cells, e.g., T or NK cells, and direct infusion of the cells into the subject. In some aspects, a nucleic acid sequence comprising a polynucleotide of the present disclosure can be inserted into the genome of a target cell (e.g., a T cell) or a host cell (e.g., a cell for recombinant expression of the CAR polypeptide) by using CRISPR/Cas systems and genome edition alternatives such as zinc-finger nucleases (ZFNs), transcription activator-like effector nucleases (TALENs), and meganucleases (MNs).

In some aspects, a construct of the present disclosure (e.g., c-Jun-anti-ROR1 CAR construct) can be expressed in a cell using bicistronic or multicistronic expression vectors. In some aspects, bicistronic or multicistronic vectors include, but are not limited to, (1) multiple promoters fused to multiple open reading frames; (2) insertion of splicing signals between open reading frames; fusion of proteins expression of which is driven by a single promoter; (3) insertion of proteolytic cleavage sites between the proteins expressed by the construct (self-cleavage peptide, e.g., P2A); and (iv) insertion of internal ribosomal entry sites (TRES s).

In some aspects, multiple protein units of the constructs herein are expressed in a single open reading frame (ORF), thereby creating a single polypeptide having multiple protein units, wherein at least one is a CAR and one is a c-Jun polypeptide of the present disclosure. In some aspects, an amino acid sequence or linker containing a high efficiency cleavage site is disposed between each protein expressed by the expression construct described herein. As used herein, high cleavage efficiency is defined as more than 50%, more than 70%, more than 80%, or more than 90% of the translated protein is cleaved. Cleavage efficiency can be measured by Western Blot analysis.

Non-limiting examples of high efficiency cleavage sites include porcine teschovirus-1 2A (P2A), FMDV 2A (abbreviated herein as F2A); equine rhinitis A virus (ERAV) 2A (E2A); and Thoseaasigna virus 2A (T2A), cytoplasmic polyhedrosis virus 2A (BmCPV2A) and flacherie Virus 2A (BmIFV2A), or a combination thereof. In some aspects, the high efficiency cleavage site is P2A. High efficiency cleavage sites are described in Kim et al. (2011) High Cleavage Efficiency of a 2A Peptide Derived from Porcine Teschovirus-1 in Human Cell Lines, Zebrafish and Mice. PLoS ONE 6(4): e18556, the contents of which are incorporated herein by reference.

In some aspects, P2A comprises or consists of a self-cleavage peptide sequence (accession #QKV27547.1, amino acids #1-22 (SEQ ID NO: 56)) derived from porcine teschovirus-1. In some aspects, the P2A sequences are codon-optimized and codon-diverged to prevent recombination. In some aspects, the P2A sequences are placed after (e.g., C-terminally) the c-Jun and anti-ROR1 CAR portions of the polynucleotides disclosed herein. In some aspects, P2A is cleaved at the polypeptide level.

In some aspects, multiple proteins are expressed in a single open reading frame (ORF), and expression is under the control of a strong promoter. In some aspects, the promoter comprises a myeloproliferative sarcoma virus enhancer, negative control region deleted, d1587rev primer-binding site substituted (MND) promoter, EFla promoter, ubiquitin promoter.

In some aspects, the vector of the present disclosure further comprises an accessory gene. In some aspects, the accessory gene is a non-immunogenic selection tool, a tracking marker, or a suicide gene. In some aspects, the accessory gene is a truncated EGFR gene (EGFRt). An example of a truncated EGFR (EGFRt) gene that can be used in accordance with the aspects described herein comprises SEQ ID NO: 3.

Polynucleotide Modifications

In some aspects, a polynucleotide encoding the proteins (e.g., c-Jun, anti-ROR1 CAR, and/or EGFRt) of the present disclosure (e.g., a c-Jun-anti-ROR1 CAR construct) can comprise at least one chemically modified nucleobase, sugar, backbone, or any combination thereof. Thus, a polynucleotide encoding the proteins of the present disclosure can comprise one or more modifications. In some aspects, a polynucleotide encoding a CAR, a c-Jun and/or an EGFRt of the present disclosure comprises at least one nucleotide analogue. In some aspects, at least one nucleotide analogue introduced by using IVT (in vitro transcription) or chemical synthesis is selected from the group consisting of a 2'-O-methoxyethyl-RNA (2'-MOE-RNA) monomer, a 2'-fluoro-DNA monomer, a 2'-O-alkyl-RNA monomer, a 2'-amino-DNA monomer, a locked nucleic acid (LNA) monomer, a cEt monomer, a cMOE monomer, a 5'-Me-LNA monomer, a 2'-(3-hydroxy)propyl-RNA monomer, an arabino nucleic acid (ANA) monomer, a 2'-fluoro-ANA monomer, an anhydrohexitol nucleic acid (HNA) monomer, an intercalating nucleic acid (INA) monomer, and a combination of two or more of said nucleotide analogues. In some aspects, the optimized nucleic acid molecule comprises at least one backbone modification, for example, a phosphorothioate internucleotide linkage.

In some aspects, a polynucleotide encoding a protein of the present disclosure (e.g., anti-ROR1, c-Jun, and/or EGFRt) can be chemically modified at terminal locations, for example, by introducing M (2'-O-methyl), MS (2'-O-methyl 3' phosphorothioate), or MSP (2'-O-methy 3'thio-PACE, phosphonoacetate) modifications, or combinations thereof at positions 1, 2, 3 respect to the 5' and/or 3' termini.

Modified polynucleotides encoding a c-Jun, CAR and/or EGFRt protein of the present disclosure (i.e., c-Jun-anti-ROR1 CAR construct) need not be uniformly modified along the entire length of the molecule. Different nucleotide modifications and/or backbone structures can exist at various positions in the nucleic acid. One of ordinary skill in the art will appreciate that the nucleotide analogs or other modification(s) can be located at any position(s) of a nucleic acid such that the function of the nucleic acid is not substantially decreased. A modification can also be a 5' or 3' terminal modification. The nucleic acids can contain at a minimum one and at maximum 100% modified nucleotides, or any intervening percentage, such as at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% modified nucleotides.

In some aspects, a polynucleotide encoding a CAR, a c-Jun and/or EGFRt of the present disclosure (e.g., c-Jun-anti-ROR1 CAR construct) can include modifications to prevent rapid degradation by endo- and exo-nucleases. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages.

Specific examples of synthetic, modified polynucleotides of the present disclosure (i.e., c-Jun-anti-ROR1 CAR constructs) useful with the methods described herein include, but are not limited to, polynucleotides containing modified or non-natural internucleoside linkages. Synthetic, modified polynucleotides having modified internucleoside linkages include, among others, those that do not have a phosphorus atom in the internucleoside linkage. In some aspects, a synthetic, modified polynucleotide has a phosphorus atom in its internucleoside linkage(s).

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, T-5' linked analogs of these, and those) having inverted polarity wherein the adjacent pairs of nucleoside units are linked 3'-5' to 5'-3' or T-5' to 5'-T. Various salts, mixed salts and free acid forms are also included.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In some aspects, a polynucleotide of the present disclosure (e.g., c-Jun-anti-ROR1 CAR construct) can be codon optimized by introducing one or more synonymous codon changes. As used herein, the terms "codon optimization," "codon optimized," and grammatical variants thereof refer to the modification of the primary sequence of a nucleic acid by replacing synonymous codons in order to increase its translational efficiency. Accordingly, codon optimization comprises switching the codons used in a polynucleotide without changing the amino acid sequence that it encodes for, which typically dramatically increases the abundance of the protein the codon optimized gene encodes because it generally removes "rare" codons and replaces them with abundant codons, or removes codon with a low tRNA recharge rate with codon with high tRNA recharge rates. Such codon optimization can, for example, (i) improve protein yield in recombinant protein expression, or (ii) improve the stability, half-life, or other desirable property of an mRNA or a DNA encoding a binding molecule disclosed herein, wherein such mRNA or DNA is administered to a subject in need thereof.

One or more of the encoding sequences of the polynucleotides of the present disclosure (e.g., c-Jun, anti-ROR1 CAR or EGFRt) can be codon optimized using any methods known in the art at the time the present application was filed.

In some aspects, a polynucleotide of the present disclosure (e.g., c-Jun-anti-ROR1 CAR construct) has been sequence optimized. As used herein, the term "sequence optimized" refers to the modification of the sequence of a nucleic acid by to introduce features that increase its translational efficiency, remove features that reduce its translational efficiency, or in general improve properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, or increasing and/or decreasing protein aggregation The present disclosure contemplates modifications to the entire construct e.g., modifications in one or more amino acid sequences of the various domains of the CAR, c-Jun, EGFRt construct in order to generate functionally equivalent molecules. The construct can be modified to retain at least about 70%, at least about 71%. at least about 72%. at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity of the starting expression construct disclosed herein (such as the construct provided in SEQ ID NO: 58). The present disclosure also contemplates modifications of specific regions of a construct, e.g., that result in modifications in one or more amino acid sequences of one or more CDRs of a CAR, or domains of c-Jun or EGFRt construct in order to generate functionally equivalent molecules.

Cells

The present disclosure also provides a genetically modified cell comprising a polynucleotide construct of the present disclosure (i.e., c-Jun-anti-ROR1 CAR construct). In some aspects, the c-Jun, anti-ROR1 CAR, and EGFRt are recombinantly expressed by a cell genetically modified to express the construct, wherein the cell comprises one or more of the polynucleotide sequences or the vectors encoding a c-Jun, CAR or EGFRt of the present disclosure.

In some aspects, the genetically modified cell disclosed herein has been transfected with a polynucleotide or vector encoding the protein components (e.g., anti-ROR1 CAR, c-Jun, and/or EGFRt) of the present disclosure. The term "transfected" (or equivalent terms "transformed" and "transduced") refers to a process by which exogenous nucleic acid, e.g., a polynucleotide or vector encoding a protein of the present disclosure (e.g., anti-ROR1, c-Jun, and/or EGFRt), is transferred or introduced into the genome of the host cell, e.g., a T cell. A "transfected" cell is one which has been transfected, transformed or transduced with exogenous nucleic acid, e.g., a polynucleotide or vector encoding the proteins of the present disclosure. The cell includes the primary subject cell and its progeny.

In some aspects, a cell described herein has been modified with a transcriptional activator, which is capable of inducing and/or increasing the endogenous expression of a protein of interest (e.g., c-Jun) in the cell. As used herein, the term "transcriptional activator" refers to a protein that increases the transcription of a gene or set of genes (e.g., by binding to enhancers or promoter-proximal elements of a nucleic acid sequence and thereby, inducing its transcription). Non-limiting examples of such transcriptional activators that can be used with the present disclosure include: Transcription Activator-like Effector (TALE)-based transcriptional activator, zinc finger protein (ZFP)-based transcriptional activator, Clustered Regularly Interspaced Short Palindromic Repeats (CRISPR)/CRISPR-associated protein (Cas) system-based transcriptional activator, or a combination thereof. See, e.g., Kabadi et al., Methods 69(2): 188-197 (September 2014), which is incorporated herein by reference in its entirety.

In some aspects, a cell described herein has been modified with a CRISPR/Cas-system-based transcriptional activator, such as CRISPR activation (CRISPRa). See, e.g., Nissim et al., Molecular Cell 54: 1-13 (May 2014), which is incorporated herein by reference in its entirety. CRISPRa is a type of CRISPR tool that comprises the use of modified Cas proteins that lacks endonuclease activity but retains the ability to bind to its guide RNA and the target DNA nucleic acid sequence. Non-limiting examples of such modified Cas proteins which can be used with the present disclosure are known in the art. See, e.g., Pandelakis et al., Cell Systems 10(1): 1-14 (January 2020), which is incorporated herein by reference in its entirety. In some aspects, the modified Cas protein comprises a modified Cas9 protein (also referred to in the art as "dCas9"). In some aspects, the modified Cas protein comprises a modified Cas12a protein. In some aspects, a modified Cas protein that is useful for the present disclosure is bound to a guide polynucleotide (e.g., small guide RNA) ("modified Cas-guide complex"), wherein the guide polynucleotide comprises a recognition sequence that is complementary to a region of a nucleic acid sequence encoding a protein of interest (e.g., c-Jun). In some aspects, the guide polynucleotide comprises a recognition sequence that is complementary to the promoter region of an endogenous nucleic acid sequence encoding a protein of interest. In some aspects, one or more transcriptional activators are attached to the modified Cas-guide complex (e.g., the N- and/or C-terminus of the modified Cas protein), such that when the modified Cas-guide complex is introduced into a cell, the one or more transcription activators can bind to a regulatory element (e.g., promoter region) of a nucleic acid sequence, and thereby induce and/or increase the expression of the encoded protein (e.g., c-Jun).

In some aspects, the one or more transcription activators can bind to a regulatory element (e.g., promoter region) of an endogenous gene, and thereby induce and/or increase the expression of the encoded protein (e.g., c-Jun). Non-limiting Illustrative examples of common general activators that can be used include the omega subunit of RNAP, VP16, VP64 and p65. See, e.g., Kabadi and Gersbach, Methods 69: 188-197 (2014), which is incorporated herein by reference in its entirety.

In some aspects, one or more transcriptional repressors (e.g., Kruppel-associated box domain (KRAB)) can be attached to the modified Cas-guide complex (e.g., the N- and/or C-terminus of the modified Cas protein), such that when introduced into a cell, the one or more transcriptional repressors can repress or reduce the transcription of a gene, e.g., such as those that can interfere with the expression of c-Jun (e.g., Bach2). See, e.g., US20200030379A1 and Yang et al., *J Transl Med* 19:459 (2021), each of which is incorporated herein by reference in its entirety. In some aspects, a modified Cas protein useful for the present disclosure can be attached to both one or more transcriptional activators and one or more transcriptional repressors.

Not to be bound by any one theory, in some aspects, the use of such modified Cas proteins can allow for the conditional transcription and expression of a gene of interest. For example, in some aspects, a cell (e.g., T cells) is modified to comprise a ligand binding protein (e.g., anti-ROR1 CAR), which is linked to a protease (e.g., tobacco etch virus (TEV)) and a single guide RNA (sgRNA) targeting the promoter region of c-Jun. In some aspects, the cell is modified to further comprise a linker for activation of T cells (LAT), complexed to the modified Cas protein attached to a transcriptional activator (e.g., dCas9-VP64-p65-Rta transcriptional activator (VPR)) via a linker (e.g., TEV-cleavable linker). Upon activation of the ligand binding protein, the modified Cas protein is released for nuclear localization and conditionally and reversibly induces the expression of c-Jun. Yang et al., J Immunother Cancer 9(Supp12): A164 (2021), which is herein incorporated by reference in its entirety.

As will be apparent to those skilled in the art, in some aspects, a cell described herein has been modified using a combination of multiple approaches. For instance, in some aspects, a cell has been modified with an exogenous polynucleotide described herein (e.g., encoding a c-Jun protein, ROR1-binding protein, and an EGFRt). In some aspects, such a cell is further modified with modified with an exogenous transcriptional activator (e.g., CRISPRa) that is capable of increasing the expression of endogenous c-Jun protein. Not to be bound by any one theory, in some aspects, such a combination approach could allow for the immune cells to have even greater level of c-Jun protein expression (e.g., both encoded by the exogenous nucleotide sequence and expressed endogenously by the immune cells).

As is apparent from the present disclosure, the immune cells described herein exhibit one or more properties that are superior compared to reference cells (e.g., corresponding cells that exists in nature). For example, in some aspects, compared to reference cells, immune cells provided herein Unless indicated otherwise, the one or more exogenous nucleotide sequences and/or transcriptional activators can be introduced into a cell using any suitable methods known in the art. Non-limiting examples of suitable methods for delivering one or more exogenous nucleotide sequences to a cell include: transfection (also known as transformation and transduction), electroporation, non-viral delivery, viral transduction, lipid nanoparticle delivery, and combinations thereof.

In some aspects, the cell (e.g., T cell) is transfected with a vector of the present disclosure, e.g., an adeno associated virus (AAV) vector or a lentiviral vector. In some such aspects, the cell can stably express the proteins of the present disclosure.

In some aspects, the cell (e.g., T cell) is transfected with a nucleic acid, e.g., mRNA, cDNA, DNA, encoding the proteins of the present disclosure (e.g., anti-ROR1, c-Jun, and/or EGFRt). In such aspects, the cell can transiently express the proteins of the present disclosure. For example, an RNA construct can be directly transfected into a cell. A method for generating mRNA for use in transfection involves in vitro transcription (IVT) of a template with specially designed primers, followed by polyA addition, to produce a construct containing 3' and 5' untranslated sequence (UTR), a 5' cap and/or Internal Ribosome Entry Site (IRES), the nucleic acid to be expressed, and a polyA tail, typically 50-2000 bases in length. RNA so produced can efficiently transfect different kinds of cells. In some aspects, the template includes sequences for the CAR, c-Jun, EGFRt, and other proteins of the present disclosure. In certain aspects, an RNA vector is transduced into a T cell by electroporation.

In some aspects, the coding sequences for proteins described herein (e.g., the CAR polypeptide and the c-Jun polypeptide) can be placed on separate expression constructs. In some aspects, the coding sequences for the proteins described herein (e.g., the CAR polypeptide, the c-Jun protein, and the EGFRt when present) can be placed on a single expression construct. The coding sequences can be placed into one or more expression cassettes on the construct, each cassette being its own transcription unit (e.g., with its own promoter and polyadenylation site and other transcription control elements). In certain aspects, the three coding sequences (e.g., encoding the CAR, c-Jun, and EGFRt, respectively) can be placed into a single expression cassette (e.g., a tri-cistronic expression cassette), with the three coding sequences being transcribed under a common promoter.

In some aspects, the cell is an immune effector cell. As used herein, term "immune effector cell" refers to a cell that is involved in an immune response, e.g., in the promotion of an immune effector response. "Immune effector function" or "immune effector response," refer to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The term "effector function" refers to a specialized function of a cell. Effector function of a T cell, for example, can be cytolytic activity or helper activity including the secretion of cytokines. The intracellular signaling domain of a CAR can generate a signal that promotes an immune effector function of the CAR containing cell, e.g., a CAR T cell. Examples of immune effector function, e.g., in a CAR T cell, include cytolytic activity and helper activity, including the secretion of cytokines. In some aspects, the intracellular signal domain is the portion of the CAR which transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion can be used in place of the intact chain as long as it transduces the effector function signal. The term intracellular signaling domain is thus meant to include any truncated portion of the intracellular signaling domain sufficient to transduce the effector function signal.

In some aspects, the intracellular signaling domain can comprise a primary intracellular signaling domain. Exemplary primary intracellular signaling domains include those derived from the molecules responsible for primary stimulation, or antigen dependent simulation. In some aspects, the intracellular signaling domain can comprise a costimulatory intracellular domain. Exemplary costimulatory intracellular signaling domains include those derived from molecules responsible for costimulatory signals, or antigen independent stimulation. For example, in the case of a CAR T cell, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, common FcR gamma (FCER1G), Fc gamma RIIk, FcR beta (Fc Epsilon Rib), CD3 gamma, CD3 delta, CD3 epsilon, CD22, CD79a, CD79b, CD278 ("ICOS"), FcεRI, CD66d, CD32, DAP10 and DAP12.

Examples of immune effector cells include, e.g., T cells, e.g., alpha/beta T cells and gamma/delta T cells, B cells, natural killer (NK) cells, natural killer T (NKT) cells, mast cells, and myeloid-derived phagocytes. Innate lymphoid cells (ILCs) are a group of innate immune cells that are derived from common lymphoid progenitor (CLP) and belong to the lymphoid lineage. These cells are defined by absence of antigen specific B or T cell receptor because of the lack of recombination activating gene (RAG). ILCs do not express myeloid or dendritic cell markers. ILCs has varying physiological functions; some functions are analogous to helper T cells, while the group also includes cytotoxic NK cells. Accordingly, in some aspects, the cell genetically modified to express a CAR of the present disclosure is, e.g., a T cell, an NK cell, an NKT cell, or an ILC cell.

T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

The source of the engineered immune cells of the present disclosure can be a patient to be treated (i.e., autologous cells) or from a donor who is not the patient to be treated (e.g., allogeneic cells). In some aspects, the engineered immune cells are engineered T cells. The engineered T cells herein can be CD4$^+$CD8$^-$ (i.e., CD4 single positive) T cells, CD4$^-$CD8$^+$ (i.e., CD8 single positive) T cells, or CD4$^+$CD8$^+$ (double positive) T cells. Functionally, the T cells can be cytotoxic T cells, helper T cells, natural killer T cells, suppressor T cells, or a mixture thereof. The T cells to be engineered can be autologous or allogeneic.

Primary immune cells, including primary T cells, can be obtained from a number of tissue sources, including peripheral blood mononuclear cells (PBMCs), bone marrow, lymph node tissue, cord blood, thymus tissue, tissue from a site of infection, ascites, pleural effusion, spleen tissue, and/or tumor tissue. Leukocytes, including PBMCs, can be isolated from other blood cells by well-known techniques, e.g., FICOLL™ separation and leukapheresis. Leukapheresis products typically contain lymphocytes (including T and B cells), monocytes, granulocytes, and other nucleated white blood cells. T cells are further isolated from other leukocytes, for example, by centrifugation through a PERCOLL™ gradient or by counterflow centrifugal elutriation. A specific subpopulation of T cells, such as CD3$^+$, CD25$^+$, CD28$^+$, CD4$^+$, CD8$^+$, CD45RA$^+$, GITR$^+$, and CD45RO$^+$ T cells, can be further isolated by positive or negative selection techniques (e.g., using fluorescence-based or magnetic-based cell sorting). For example, T cells can be isolated by incubation with any of a variety of commercially available antibody-conjugated beads, such as Dynabeads®, CELLection™, DETACHaBEAD™ (Thermo Fisher) or MACS® cell separation products (Miltenyi Biotec), for a time period sufficient for positive selection of the desired T cells or negative selection for removal of unwanted cells.

In some instances, autologous T cells are obtained from a cancer patient directly following cancer treatment. It has been observed that following certain cancer treatments, in particular those that impair the immune system, the quality of T cells collected shortly after treatment can have an improved ability to expand ex vivo and/or to engraft after being engineered ex vivo.

Whether prior to or after genetic modification, T cells can be activated and expanded generally using methods as described, for example, in U.S. Pat. Nos. 5,858,358; 5,883,223; 6,352,694; 6,534,055; 6,797,514; 6,867,041; 6,692,964; 6,887,466; 6,905,680; 6,905,681; 6,905,874; 7,067,318; 7,144,575; 7,172,869; 7,175,843; 7,232,566; 7,572,631; and 10,786,533, each of which is expressly incorporated by reference herein in its entirety. Generally, T cells can be expanded in vitro or ex vivo by contact with a surface having attached thereto an agent that stimulates a CD3/TCR complex associated signal and a ligand that stimulates a costimulatory molecule on the surface of the T cells. In particular, T cell populations can be stimulated, such as by contact with an anti-CD3 antibody or antigen-binding fragment thereof, or an anti-CD3 antibody immobilized on a surface, or by contact with a protein kinase C activator (e.g., bryostatins) in conjunction with a calcium ionophore. For co-stimulation of an accessory molecule on the surface of the T cells, a ligand that binds the accessory molecule can be used. For example, a population of T cells can be contacted with an anti-CD3 antibody and an anti-CD28 antibody under conditions appropriate for stimulating proliferation of the T cells. To stimulate proliferation of either CD4$^+$ T cells or CD8$^+$ T cells, an anti-CD3 antibody and an anti-CD28 antibody can be employed.

The cell culture conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some aspects, the culture conditions include addition of IL-2, IL-7 and/or IL-15.

In some aspects, the cells to be engineered can be pluripotent or multipotent cells that are differentiated into mature T cells after engineering. These non-T cells can be allogeneic and can be, for example, human embryonic stem cells, human induced pluripotent stem cells, or hematopoietic stem or progenitor cells. For ease of description, pluripotent and multipotent cells are collectively called "progenitor cells" herein.

Where allogeneic cells are used, in certain aspects, they are engineered to reduce graft-versus-host rejection (e.g., by knocking out the endogenous B2M and/or TRAC genes).

Pharmaceutical Compositions

The present disclosure also provides pharmaceutical compositions comprising compositions disclosed herein, e.g., a polynucleotide encoding the proteins (e.g., c-Jun, anti-ROR1 CAR, EGFRt) of the present disclosure (e.g., a c-Jun-anti-ROR1 construct), a vector comprising a polynucleotide encoding an anti-ROR1 CAR, a c-Jun and an EGFRt proteins of the present disclosure (e.g., a c-Jun-anti-ROR1 CAR construct), or a genetically modified cell comprising a polynucleotide construct or a vector encoding an anti-ROR1 CAR, a c-Jun and an EGFRt proteins of the present disclosure, which are suitable for administration to a subject.

The pharmaceutical compositions generally comprise polynucleotide, vector, or cell encoding or comprising an anti-ROR-1 CAR, a c-Jun and EGFRt protein of the present disclosure and a pharmaceutically-acceptable excipient or carrier in a form suitable for administration to a subject. Pharmaceutically acceptable excipients or carriers are determined in part by the particular composition being administered, as well as by the particular method used to administer the composition.

The present disclosure provides pharmaceutical compositions comprising engineered T cells modified with the expression constructs described herein (e.g., c-Jun-anti- ROR1 CAR constructs described herein). The pharmaceutical compositions can comprise a pharmaceutically acceptable carrier that is suitable to maintain the health of the cells before introduction into the patient.

In some aspects, engineered cells can be harvested from a culture medium, and washed and concentrated into a carrier in a therapeutically effective amount. Exemplary carriers include saline, buffered saline (e.g., phosphate buffered saline), physiological saline, water, Hanks' solution, Ringer's solution, Nonnosol-R (Abbott Labs), Plasma-Lyte A(R) (Baxter Laboratories, Inc., Morton Grove, IL), glycerol, ethanol, and combinations thereof. It is preferred that the carrier is isotonic. In some aspects, the carrier can be supplemented with ingredients such as human serum albumin (HSA) or other human serum components, 5% glucose or dextrose. Additional isotonic agents include polyhydric sugar alcohols including trihydric or higher sugar alcohols, such as glycerin, erythritol, arabitol, xylitol, sorbitol, or mannitol can also be included.

The pharmaceutical T cell compositions can be administered in a therapeutically effective amount to a cancer patient systemically (e.g., through intravenous or portal vein injection) or locally (e.g., through intratumoral injection). In some aspects, the compositions such as those targeting ROR1 are used to treat a patient with a tumor known to express ROR1. In some aspects, the compositions such as those targeting ROR1 are used to treat a patient with a cancer selected from metastatic melanoma, non-small cell lung cancer, myeloma, esophageal cancer, synovial sarcoma, gastric cancer, breast cancer, hepatocellular cancer, head and neck cancer, ovarian cancer, prostate cancer, and bladder cancer. As used herein, the term "treatment" or "treating" refers to an approach for obtaining beneficial or desired results in the treated subject. Such results include, but are not limited to: alleviating one or more symptoms resulting from the disease, diminishing the extent of the disease (e.g., reducing tumor volumes), stabilizing the disease (e.g., preventing or delaying the worsening of the disease), preventing or delaying the spread (e.g., metastasis) of the disease, preventing or delaying the recurrence or relapse of the disease, ameliorating the disease state, providing a remission (partial or total) of the disease, decreasing the dose of one or more other medications required to treat the disease, improving the quality of life, restoring body weight, and/or extension of survival (e.g., overall survival or progression-free survival).

A therapeutically effective amount of the composition refers to the number of engineered T cells sufficient to achieve a desired clinical endpoint. In some aspects, a therapeutically effective amount contains more than about $10^4$, more than about $10^5$, more than about $10^6$, more than about $10^7$, more than about $10^8$, or more than about $10^9$ of the engineered cells.

The pharmaceutical composition in some aspects comprises the cells in amounts effective to treat or prevent the disease or condition, such as a therapeutically effective or prophylactically effective amount. Therapeutic or prophylactic efficacy in some aspects is monitored by periodic assessment of treated subjects. For repeated administrations over several days or longer, depending on the condition, the treatment is repeated until a desired suppression of disease symptoms occurs. However, other dosage regimens can be useful and can be determined. The desired dosage can be delivered by a single bolus administration of the composition, by multiple bolus administrations of the composition, or by continuous infusion administration of the composition.

There is a wide variety of suitable formulations of pharmaceutical compositions comprising a CAR of the present disclosure (see, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration.

In certain aspects, the pharmaceutical composition is co-administered with of one or more additional therapeutic agents, in a pharmaceutically acceptable carrier. In some aspects, the pharmaceutical composition comprising the polynucleotide described herein (e.g., encoding an anti-ROR1 CAR, c-Jun, and/or EGFRt) is administered prior to administration of the additional therapeutic agent(s). In certain aspects, the pharmaceutical composition comprising the polynucleotide of the present disclosure (e.g., encoding an anti-ROR1 CAR, c-Jun, and/or EGFRt) is administered after the administration of the additional therapeutic agent(s). In further aspects, the pharmaceutical composition comprising the polynucleotide of the present disclosure (e.g., encoding an anti-ROR1 CAR, c-Jun, and/or EGFRt) is administered concurrently with the additional therapeutic agent(s).

Acceptable carriers, excipients, or stabilizers are nontoxic to recipients (e.g., animals or humans) at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the compositions of the present disclosure (e.g., polynucleotides, vectors, or cells), use thereof in the compositions is contemplated.

Indications

In some aspects, the compositions disclosed herein (e.g., anti-ROR1 CAR T cells overexpressing c-Jun) can be used to treat a disease or condition, e.g., a proliferative disease such as a cancer or malignancy or a precancerous condition such as a myelodysplasia, a myelodysplastic syndrome or a preleukemia.

A "cancer" refers to a broad group of various proliferative diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. As used herein the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth. In some aspects, the cancer is a tumor. "Tumor," as used herein, refers to all neoplastic cell growth and proliferation, whether malignant or benign, and all pre-cancerous and cancerous cells and tissues.

In some aspects, the engineered anti-ROR1 CAR T cells overexpressing c-Jun can be used to treat relapsed or refractory solid-tumor malignancies that are ROR1 positive. In certain aspects, the disease to be treated is breast cancer, such as triple negative breast cancer, or non-small cell lung carcinoma. In some aspects, the disease is a solid or a liquid tumor. In some aspects, the cancer is a pancreatic cancer. In some aspects, the disease is a hematologic cancer. In some aspects, the hematologic cancer is a leukemia.

In some aspects, the compositions disclosed herein (e.g., cells engineered to express polynucleotides encoding c-Jun and CARs of the present disclosure, vectors comprising polynucleotides encoding c-Jun and CARs of the present disclosure, c-Jun and CARs of the present disclosure, or cells expressing c-Jun and CARs of the present disclosure, e.g., CAR T cells) are used to reduce or decrease a size of a tumor or inhibit a tumor growth in a subject in need thereof. In some aspects, the tumor is a carcinoma (i.e., a cancer of epithelial origin). In some aspects, the tumor is, e.g., selected from the group consisting of gastric cancer, gastroesophageal junction cancer (GEJ), esophageal cancer, colorectal cancer, liver cancer (hepatocellular carcinoma, HCC), ovarian cancer, breast cancer, NSCLC, bladder cancer, lung cancer, pancreatic cancer, head and neck cancer, lymphoma, uterine cancer, renal or kidney cancer, biliary cancer, prostate cancer, testicular cancer, urethral cancer, penile cancer, thoracic cancer, rectal cancer, brain cancer (glioma and glioblastoma), cervical cancer, parotid cancer, larynx cancer, thyroid cancer, adenocarcinomas, neuroblastomas, melanoma, and Merkel Cell carcinoma.

A "cancer" or "cancer tissue" can include a tumor at various stages. In certain aspects, the cancer or tumor is stage 0, such that, e.g., the cancer or tumor is very early in development and has not metastasized. In some aspects, the cancer or tumor is stage I, such that, e.g., the cancer or tumor is relatively small in size, has not spread into nearby tissue, and has not metastasized. In some aspects, the cancer or tumor is stage II or stage III, such that, e.g., the cancer or tumor is larger than in stage 0 or stage I, and it has grown into neighboring tissues but it has not metastasized, except potentially to the lymph nodes. In some aspects, the cancer or tumor is stage IV, such that, e.g., the cancer or tumor has metastasized. Stage IV can also be referred to as advanced or metastatic cancer.

In some aspects, the cancer can include, but is not limited to, adrenal cortical cancer, advanced cancer, anal cancer, aplastic anemia, bileduct cancer, bladder cancer, bone cancer, bone metastasis, brain tumors, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, Hodgkin disease, Kaposi sarcoma, renal cell carcinoma, laryngeal and hypopharyngeal cancer, acute lymphocytic leukemia, acute myeloid leukemia, chronic lymphocytic leukemia, chronic myeloid leukemia, chronic myelomonocytic leukemia, liver cancer, non-small cell lung cancer, small cell lung cancer, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal and squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment.

In some aspects, the tumor is a solid tumor. A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" refers to a tumor arising from the melanocytic system of the skin and other organs. Melanomas include, for example, acra-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas include, e.g., acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma viflosum.

Additional cancers that can be treated with the compositions disclosed herein (e.g., cells engineered to express polynucleotides encoding c-Jun and CARs of the present disclosure, vectors comprising polynucleotides encoding c-Jun and CARs of the present disclosure, c-Jun and CARs of the present disclosure, or cells expressing c-Jun and CARs of the present disclosure, e.g., CAR T cells) include, e.g., Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, prostate cancer, Müllerian cancer, ovarian cancer, peritoneal cancer, fallopian tube cancer, or uterine papillary serous carcinoma.

Methods

The present disclosure also provide methods for using one or more of the compositions described herein (e.g., a polynucleotide encoding c-Jun and an anti-ROR1 CAR; vector comprising the polynucleotide; or cell transduced with the vector, such as an anti-ROR1 CAR T cell overexpressing c-Jun as described herein) for adoptive therapy. While the disclosures provided below largely refer to the administration of cells (e.g., anti-ROR1 CAR T cells overexpressing c-Jun), it will be apparent to those skilled in the art that the described methods can be achieved administering to the subject any of the other compositions described herein (e.g., a polynucleotide encoding c-Jun and an anti-ROR1 CAR or a vector comprising the polynucleotide).

In some aspects, the present disclosure provides a method of stimulating a T cell-mediated immune response to a target cell population or tissue in a subject, comprising administering an effective amount of a cell expressing an anti-ROR1 CAR and ovexpressing a c-Jun polypeptide of the present disclosure to the subject. Also provided is a method of providing an anti-tumor immunity in a subject in need thereof, the method comprising administering to the subject an effective amount of a cell expressing an anti-ROR1 CAR and overexpressing a c-Jun polypeptide of the present disclosure to the subject.

The disclosure also provides a method of treating cancer in a subject in need thereof comprising administering to the subject an effective amount of a cell expressing an anti-ROR1 CAR and overexpressing a c-Jun polypeptide of the present disclosure. In some aspects, a method of treating a cancer comprises administering to a subject in need thereof an immune cell, which overexpresses a c-Jun polypeptide and comprises a chimeric antigen receptor (CAR) and a truncated EGF receptor (EGFRt), wherein the CAR is specific or an antigen expressed on the tumor. Non-limiting examples of such immune cell is described throughout the present disclosure. As is apparent from the present disclosure, such methods could be useful in treating any cancers associated with ROR1 expression. Non-limiting examples of such cancers are provided elsewhere in the present disclosure.

As demonstrated herein, in some aspects, administering a modified immune cell described herein (e.g., overexpresses a c-Jun polypeptide and comprises a CAR (e.g., anti-ROR1 CAR) and EGFRt) to a subject can reduce or alleviate one or more symptoms or aspects of the cancer. For example, in some aspects, administering a modified immune cell described herein can result in decreased tumor size compared to a reference tumor size. In some aspects, the reference tumor size comprises: (i) the tumor size before the administration, (ii) the tumor size in a corresponding subject that did not receive the administration (e.g., received an administration of a corresponding immune cell that does not overexpress the c-Jun polypeptide), or (iii) both (i) and (ii). In some aspects, administering a modified immune cell provided herein can decrease the size of the tumor in the subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% compared to the reference tumor size.

In some aspects, administering a modified immune cell described herein can improve the duration of survival of the subject. In some aspects, compared to the reference duration of survival, the duration of survival is increased by at least about one week, at least about two weeks, at least about three weeks, at least about one month, at least about two months, at least about three months, at least about four months, at least about five months, at least about six months, at least about seven months, at least about eight months, at least about nine months, at least about 10 months, at least about 11 months, or at least about one year. In some aspects, the reference duration of survival comprises the duration of survival of a corresponding subject who did not receive the administration (e.g., received an administration of a corresponding immune cell that does not overexpress the c-Jun polypeptide).

As further described elsewhere in the present disclosure, in some aspects, the modified immune cells described herein exhibit improved ability to kill tumor cells compared to reference cells (e.g., corresponding cells that were not modified to overexpress c-Jun). Accordingly, in some aspects, provided herein is a method of killing tumor cells comprising contacting the tumor cells with an immune cell, which overexpresses a c-Jun polypeptide and comprises a chimeric antigen receptor (CAR) and a truncated EGF receptor (EGFRt), wherein the CAR is specific for an antigen expressed on the tumor cells. Non-limiting examples of such immune cells are provided throughout the present disclosure. In some aspects, compared to reference cells (e.g., corresponding cells that were not modified as described herein), the killing of the tumor cells is increased by at least about 0.5-fold, 1-fold, at least about 2-fold, at least about 3-fold, at least about 4-fold, or at least about 5-fold.

As is apparent from the present disclosure, modified immune cells of the present disclosure exhibit various superior properties compared to reference cells (e.g., corresponding cells that were not modified to overexpress c-Jun). For instance, in some aspects, modified cells described herein are capable of producing increased amount of cytokine (e.g., IFN-γ, IL-2, or both) when stimulated with an antigen. Accordingly, in some aspects, provided herein is a method of increasing the production of a cytokine by an immune cell in response to antigen stimulation comprising modifying an immune cell to (i) express a ROR-1 binding protein and (ii) have an increased level of a c-Jun polypeptide as compared to a corresponding immune cell that has not been modified to have increased level of the c-Jun polypeptide. In some aspects, the ROR-1 binding protein specifically binds to the same epitope as the R12 antibody. In some aspects, the production of the cytokine in response to the antigen stimulation is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more compared to the corresponding immune cell. In some aspects, the production of the cytokine is increased by at least about 5%, at least about 10%, at least about 20%, at least about 30%, at least about 40%, at least about 50%, at least about 60%, at least about 70%, at least about 80%, at least about 90%, or at least about 100% or more.

In some aspects, modified immune cells described herein exhibit increased proliferation in response to antigen stimulation compared to a reference cell (e.g., corresponding immune cell that was not modified to overexpress c-Jun). Accordingly, also provided herein is a method of increasing proliferation of an immune cell in response to antigen stimulation comprising modifying an immune cell to (i) express a ROR-1 binding protein and (ii) have an increased level of a c-Jun polypeptide as compared to a corresponding immune cell that has not been modified to have increased level of the c-Jun polypeptide. In some aspects, the ROR-1 binding protein specifically binds to the same epitope as the R12 antibody. In some aspects, after the modification, the proliferation of the immune cell in response to antigen stimulation is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more compared to the corresponding immune cell. In some aspects, the proliferation is increased by at least about 5%, at least about 10%, at least about 20%, at least about 30%, at least about 40%, at least about 50%, at least about 60%, at least about 70%, at least about 80%, at least about 90%, or at least about 100% or more.

As is apparent from the present disclosure, the methods provided herein can also be used to increase one or more effector function of an immune response in response to persistent antigen stimulation. Non-limiting examples of effector functions that can be improved include: the ability: (i) to kill tumor cells (ii) to produce a cytokine upon further antigen stimulation, or (iii) both (i) and (ii). In some aspects, such a method comprises modifying an immune cell to (i) express a ROR-1 binding protein and (ii) have an increased level of a c-Jun polypeptide as compared to a corresponding immune cell that has not been modified to have increased level of the c-Jun polypeptide. In some aspects, the ROR-1 binding protein specifically binds to the same epitope as the R12 antibody.

In some aspects, after the modification, the immune cell retains effector function for at least one, at least two, or at least three additional rounds of an antigen stimulation assay, as compared to the corresponding immune cell.

In some aspects, after the modification, the effector function of the immune cell is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more as compared to the corresponding immune cell. In some aspects, the effector function is increased by at least about 5%, at least about 10%, at least about 20%, at least about 30%, at least about 40%, at least about 50%, at least about 60%, at least about 70%, at least about 80%, at least about 90%, or at least about 100% or more.

In some aspects, methods provided herein can also be used to reduce or prevent exhaustion in immune cells (e.g., T cells) after persistent antigen stimulation. In some aspects, such a method comprises modifying an immune cell to (i) express a ROR-1 binding protein and (ii) have an increased level of a c-Jun polypeptide as compared to a corresponding immune cell that has not been modified to have increased level of the c-Jun polypeptide. In some aspects, the ROR-1 binding protein specifically binds to the same epitope as the R12 antibody.

In some aspects, after the modification, in response to the persistent antigen stimulation, the immune cells express: (i)

decreased level of genes associated with exhaustion, (ii) increased level of genes associated with activation, or (iii) both (i) and (ii), as compared to the corresponding immune cell. Non-limiting examples of such genes are described elsewhere in the present disclosure.

The disclosure also provides a method of preparing a population of cells, e.g. anti-ROR1 CAR T cells overexpressing a c-Jun polypeptide, for a therapy comprising transducing a population of cells isolated from a subject with the a polynucleotide or vector of the present disclosure. In some aspects, the transduction comprises culturing the cell under suitable condition.

The disclosure also provides a method of generating a persisting population of genetically engineered cells in a subject diagnosed with cancer, the method comprising administering to the subject a cell genetically engineered to express an anti-ROR1 CAR and overexpress a c-Jun polypeptide of the present disclosure. Not to be bound by any one theory, as described elsewhere in the present disclosure, the overexpression of c-Jun can help reduce or prevent exhaustion, such that when the modified immune cells of the present disclosure are administered to a subject, they are able to persist in the subject longer compared to reference cells (e.g., corresponding cells that were not modified to overexpress c-Jun). In some aspects, when administered to a subject, the modified immune cells of the present disclosure are capable of persisting in the subject for at least about 1 week, at least about 2 weeks, at least about three weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about a year or longer than the corresponding immune cells. Accordingly, in some aspects, compared to the corresponding immune cells when administered to a reference subject, the number of the modified immune cells present in the subject at about 1 month after the administration is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 2 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 3 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 4 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 5 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 6 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 7 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds. In some aspects, at about 8 months after the administration, compared to the corresponding immune cells in the reference subject, the number of the modified immune cells is greater by at least about 1-fold, at least about 2-fold, at least about 3-fold, at least about 4-fold, at least about 5-fold, at least about 6-fold, at least about 7-folds, at least about 8-folds, at least about 9-folds, or at least about 10-folds.

The disclosure also provides a method of expanding a population of genetically engineered cells (e.g., T cells) in a subject diagnosed with cancer, the method comprising administering to the subject a cell (e.g., a T cell) genetically engineered to express an anti-ROR1 CAR and overexpress a c-Jun polypeptide of the present disclosure. In some aspects, the cell is a T cell, e.g., an autologous T cell. In some aspects, the T cell is a heterologous T cell. In some aspects of the methods disclosed herein, the subject is a human subject.

In some aspects, administration of a composition comprising an anti-ROR1 CAR of the present disclosure (e.g., c-Jun-anti-ROR1 CAR construct) results in an increase in interleukin (e.g., interleukin-2) secretion by at least about 0.01-fold, at least about 0.02-fold, at least about 0.03-fold, at least about 0.04-fold, at least about 0.05-fold, at least about 0.06-fold, at least about 0.07-fold, at least about 0.08-fold, at least about 0.09-fold, at least about 0.1-fold, at least about 0.2-fold, at least about 0.3-fold, at least about 0.4-fold, at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more compared to the interleukin secretion observed after administration of a corresponding composition comprising an anti-ROR1 CAR (e.g., not overexpressing c-Jun) instead of a CAR of the present disclosure.

In some aspects, administration of a composition comprising an anti-ROR1 CAR of the present disclosure (e.g., c-Jun-anti-ROR1 CAR construct) results in an increase in interferon (e.g., interferon-gamma) secretion by at least about 0.01-fold, at least about 0.02-fold, at least about 0.03-fold, at least about 0.04-fold, at least about 0.05-fold, at least about 0.06-fold, at least about 0.07-fold, at least about 0.08-fold, at least about 0.09-fold, at least about 0.1-fold, at least about 0.2-fold, at least about 0.3-fold, at least about 0.4-fold, at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more compared to the interferon (e.g., interferon-gamma) secretion observed after administration of a corresponding composition comprising an anti-ROR1 CAR (e.g., not overexpressing c-Jun) instead of a CAR of the present disclosure.

In some aspects, administration of a composition comprising an anti-ROR1 CAR of the present disclosure (e.g., c-Jun-anti-ROR1 CAR construct) results in an increase in TNFα secretion by at least about 0.01-fold, at least about 0.02-fold, at least about 0.03-fold, at least about 0.04-fold, at least about 0.05-fold, at least about 0.06-fold, at least about 0.07-fold, at least about 0.08-fold, at least about 0.09-fold, at least about 0.1-fold, at least about 0.2-fold, at least about 0.3-fold, at least about 0.4-fold, at least about 0.5-fold, at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, at least about 20-fold, at least about 25-fold, at least about 30-fold, at least about 35-fold, at least about 40-fold, at least about 45-fold, at least about 50-fold, at least about 75-fold, at least about 100-fold, at least about 200-fold, at least about 300-fold, at least about 400-fold, at least about 500-fold, at least about 750-fold, or at least about 1,000-fold or more compared to the TNFα secretion observed after administration of a corresponding composition comprising an anti-ROR1 CAR (e.g., not overexpressing c-Jun) instead of a CAR of the present disclosure.

In some aspects, the present disclosure provides a polynucleotide, vector, CAR, composition, kit, cell, or the pharmaceutical composition of the present disclosure for use as a medicament. In some aspects, the present disclosure provides a polynucleotide, vector, CAR, composition, kit, cell, or the pharmaceutical composition of the present disclosure for use as a medicament for the treatment of cancer in a subject in need thereof. In some aspects, the present disclosure provides a polynucleotide, vector, CAR, composition, kit, cell, or the pharmaceutical composition of the present disclosure for the treatment of cancer in a subject in need thereof. In some aspects, the present disclosure provides the use of a polynucleotide, vector, CAR, composition, kit, cell, or the pharmaceutical composition of the present disclosure for the manufacture of a medicament. In some aspects, the present disclosure provides the use of a polynucleotide, vector, CAR, composition, kit, cell, or the pharmaceutical composition of the present disclosure for the manufacture of a medicament for treating cancer in a subject in need thereof.

The present disclosure also provides a composition comprising a polynucleotide construct (e.g., c-Jun-anti-ROR1 CAR construct), a vector comprising the construct (e.g., encoding a c-Jun, CAR or EGFRt), or a genetically modified cell comprising the construct or the vector for treating a subject in need of a CAR therapy. The present disclosure also provides a composition comprising a polynucleotide construct of the present disclosure (e.g., c-Jun-anti-ROR1 CAR construct), a vector comprising the polynucleotide construct, or a genetically modified cell comprising the polynucleotide or the vector encoding a c-Jun, CAR, or EGFRt for use as a medicament. Also provided is a composition comprising a polynucleotide construct of the present disclosure (e.g., a c-Jun-anti-ROR1 CAR construct), a vector comprising the polynucleotide construct, or a genetically modified cell comprising the polynucleotide construct or a vector encoding a c-Jun, CAR or EGFRt for use as treatment for cancer in a subject in need of a CAR therapy. Also provided is a composition comprising a polynucleotide construct (e.g., c-Jun-anti-ROR1 CAR construct), a vector comprising a polynucleotide encoding a c-Jun, CAR, or EGFRt, or a genetically modified cell comprising a polynucleotide or a vector encoding a c-Jun, CAR, or EGFRt for the manufacture of a medicament for the treatment for cancer in a subject in need of a CAR therapy.

In some aspects, the present disclosure provides methods of preparing a cell expressing a chimeric antigen receptor comprising transfecting a cell with the polynucleotides disclosed herein (e.g., c-Jun-anti-ROR1 CAR construct). In some aspects, the cell comprises a T cell, a B cell, a regulatory T cell (Treg), a tumor infiltrating lymphocyte (TIL), a natural killer (NK) cell, a natural killer T (NKT) cell, a stem cell, an induced pluripotent stem cell, and any combination thereof.

In some aspects, the present disclosure provides a method of expanding a cell expressing a chimeric antigen receptor comprising culturing a cell comprising a polynucleotide disclosed herein or a vector disclosed herein or a polypeptide disclosed herein, under suitable conditions.

In some aspects, the methods of treatment disclosed herein further comprise administering at least one additional therapeutic agent. In some aspects, the additional therapeutic agent comprises a chemotherapeutic drug, targeted anticancer therapy, oncolytic drug, cytotoxic agent, immune-based therapy, cytokine, surgical procedure, radiation procedure, activator of a costimulatory molecule, immune checkpoint inhibitor, a vaccine, a cellular immunotherapy, or any combination thereof. In some aspects, the immune checkpoint inhibitor comprises an anti-PD-1 antibody, anti-PD-L1 antibody, anti-LAG-3 antibody, anti-CTLA-4 antibody, anti-GITR antibody, anti-TIM3 antibody, or any combination thereof.

Kits

The present disclosure also provides kits, or products of manufacture comprising (i) one or more polynucleotides encoding an anti-ROR1 CAR, a c-Jun, and/or EGFRt proteins of the present disclosure (e.g., c-Jun-anti-ROR1 CAR construct), one or more vectors encoding the one or more polynucleotides described herein (e.g., anti-ROR1 CAR, c-Jun, and/or EGFRt), or a composition comprising the polynucleotide(s) or vector(s), and optionally (ii) instructions for use, e.g., instructions for use according to the methods disclosed herein.

The disclosure also provides a kits comprising (i) a cell genetically modified to express an anti-ROR1 CAR, a c-Jun, and EGFRt protein of the present disclosure, i.e., a cell comprising one or more polynucleotides encoding an anti- ROR1 CAR, a c-Jun polypeptide, and/or a EGFRt protein of the present disclosure, or one or more vectors comprising the one or more polynucleotides described herein (e.g., a T cell, a natural killer (NK) cell, an natural killer T (NKT) cell, or an ILC cell), or a pharmaceutical composition comprising the cell, and optionally (ii) instructions for use.

In some aspects, the kit or product of manufacture comprises at least a polynucleotide or vector encoding an anti-ROR1 CAR, a c-Jun polypeptide, and/or a EGFRt protein of the present disclosure, a cell genetically modified to express an anti-ROR1 CAR, a c-Jun polypeptide, and/or a EGFRt protein of the present disclosure, or a composition (e.g., a pharmaceutical composition) comprising a polynucleotide, vector, or cell disclosed herein, in one or more containers.

In some aspects, the kit or product of manufacture comprises at least a polynucleotide or vector encoding an anti-ROR1 CAR, a c-Jun polypeptide, and a EGFRt protein of the present disclosure, a cell genetically modified to express an anti-ROR1 CAR, a c-Jun, and a EGFRt of the present disclosure, or a composition (e.g., a pharmaceutical composition) comprising a polynucleotide, vector, or cell disclosed herein, and optionally a brochure.

One skilled in the art will readily recognize that the polynucleotides, vectors, cells, and compositions of the present disclosure, pharmaceutical composition comprising the polynucleotides, vectors, or cells of the present disclosure, or combinations thereof can be readily incorporated into one of the established kit formats which are well known in the art.

In some aspects, the kit or product of manufacture comprises, e.g., a polynucleotide or vector encoding an anti-ROR1 CAR, a c-Jun polypeptide, and a EGFRt protein of the present disclosure, or a composition (e.g., a pharmaceutical composition) comprising a polynucleotide, vector, in dry form in a container (e.g., a glass vial), and optionally a vial with a solvent.

In some aspects, the kit or product of manufacture comprises, e.g., a polynucleotide or vector encoding an anti-ROR1 CAR, a c-Jun peptide, and a EGFRt protein of the present disclosure, or a composition (e.g., a pharmaceutical composition) comprising a polynucleotide, vector, in at least one container, and another or more containers with transfection reagents.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, N.Y.); D. N. Glover ed., (1985) DNA Cloning, Volumes I and II; Gait. ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooke, Antisense drug Technology: Principles, Strategies and Applications, 2nd Ed. CRC Press (2007) and in Ausubel et al. (1989) Current Protocols in Molecular Biology (John Wiley and Sons, Baltimore, Md.).

The following examples are offered by way of illustration and not by way of limitation.

EXAMPLES

TABLE 7 c-Jun-anti-ROR1 CAR sequences
c-Jun-anti-ROR1 CAR

| SEQ ID NO | Description | Sequence |
|---|---|---|
| 57 | Full sequence 1,198aa | MTAKMETTFYDDALNASFLPSESGPYGYSNPKILKQSMTLNLADPVGSLKPH LRAKNSDLLTSPDVGLLKLASPELERLIIQSSNGHITTTPTPTQFLCPKNVT DEQEGFAEGFVRALAELHSQNTLPSVTSAAQPVNGAGMVAPAVASVAGGSGS GGFSASLHSEPPVYANLSNFNPGALSSGGGAPSYGAAGLAFPAQPQQQQQPP HHLPQQMPVQHPRLQALKEEPQTVPEMPGETPPLSPIDMESQERIKAERKRM RNRIAASKCRKRKLERIARLEEKVKTLKAQNSELASTANMLREQVAQLKQKV MNHVNSGCQLMLTQQLQTFGSGATNFSLLKQAGDVEENPGPMVLQTQVFISL LLWISGAYGQEQLVESGGRLVTPGGSLTLSCKASGFDFSAYYMSWVRQAPGK GLEWIATIYPSSGKTYYATWVNGRFTISSDNAQNTVDLQMNSLTAADRATYF CARDSYADDGALFNIWGPGTLVTISSGGGGSGGGGSGGGGSELVLTQSPSVS AALGSPAKITCTLSSAHKTDTIDWYQQLQGEAPRYLMQVQSDGSYTKRPGVP DRFSGSSSGADRYLIIPSVQADDEADYYCGADYIGGYVFGGGTQLTVTGGGG SGKPCPPCKCPMFWVLVVVGGVLACYSLLVTVAFIIFWVKRGRKKLLYIFKQ PFMRPVQTTQEEDGCSCRFPEEEEGGCELRVKFSRSADAPAYQQGQNQLYNE LNLGRREEYDVLDKRRGRDPEMGGKPRRKNPQEGLYNELQKDKMAEAYSEIG MKGERRRGKGHDGLYQGLSTATKDTYDALHMQALPPRSGATNFSLLKQAGDV EENPGPMLLLVTSLLLCELPHPAFLLIPRKVCNGIGIGEFKDSLSINATNIK HFKNCTSISGDLHILPVAFRGDSFTHTPPLDPQELDILKTVKEITGFLLIQA WPENRTDLHAFENLEIIRGRTKQHGQFSLAVVSLNITSLGLRSLKEISDGDV IISGNKNLCYANTINWKKLFGTSGQKTKIISNRGENSCKATGQVCHALCSPE |

TABLE 7-continued c-Jun-anti-ROR1 CAR sequences
c-Jun-anti-ROR1 CAR

| SEQ ID NO | Description | Sequence |
|---|---|---|
|  |  | GCWGPEPRDCVSCRNVSRGRECVDKCNLLEGEPREFVENSECIQCHPECLPQ AMNITCTGRGPDNCIQCAHYIDGPHCVKTCPAGVMGENNTLVWKYADAGHVC HLCHPNCTYGCTGPGLEGCPTNGPKIPSIATGMVGALLLLLVVALGIGLFMR RR |
| 1 | c-Jun<br>331aa<br>aa 1-331 | MTAKMETTFYDDALNASFLPSESGPYGYSNPKILKQSMTLNLADPVGSLKPH LRAKNSDLLTSPDVGLLKLASPELERLIIQSSNGHITTTPTPTQFLCPKNVT DEQEGFAEGFVRALAELHSQNTLPSVTSAAQPVNGAGMVAPAVASVAGGSGS GGFSASLHSEPPVYANLSNFNPGALSSGGGAPSYGAAGLAFPAQPQQQQQPP HHLPQQMPVQHPRLQALKEEPQTVPEMPGETPPLSPIDMESQERIKAERKRM RNRIAASKCRKRKLERIARLEEKVKTLKAQNSELASTANMLREQVAQLKQKV MNHVNSGCQLMLTQQLQTF |
| 59 | c-Jun after P2A cleavage (remnant boxed) | MTAKMETTFYDDALNASFLPSESGPYGYSNPKILKQSMTLNLADPVGSLKPH LRAKNSDLLTSPDVGLLKLASPELERLIIQSSNGHITTTPTPTQFLCPKNVT DEQEGFAEGFVRALAELHSQNTLPSVTSAAQPVNGAGMVAPAVASVAGGSGS GGFSASLHSEPPVYANLSNFNPGALSSGGGAPSYGAAGLAFPAQPQQQQQPP HHLPQQMPVQHPRLQALKEEPQTVPEMPGETPPLSPIDMESQERIKAERKRM RNRIAASKCRKRKLERIARLEEKVKTLKAQNSELASTANMLREQVAQLKQKV MNHVNSGCQLMLTQQLQTF GSGATNFSLLKQAGDVEENPG |
| 56 | P2A<br>22aa<br>aa 332-353 | GSGATNFSLLKQAGDVEENPGP |
| 17 | hIgK<br>20aa<br>aa 354-373 | MVLQTQVFISLLLWISGAYG |
| 60 | hIgK after P2A cleavage | PMVLQTQVFISLLLWISGAYG. (P2A remnant residue double underlined |
| 52 | scFv<br>248aa<br>aa 374-621 | QEQLVESGGRLVTPGGSLTLSCKASGFDFSAYYMSWVRQAPGKGLEWIATIY PSSGKTYYATWVNGRFTISSDNAQNTVDLQMNSLTAADRATYFCARDSYADD GALFNIWGPGTLVTISSGGGGSGGGGSGGGGSELVLTQSPSVSAALGSPAKI TCTLSSAHKTDTIDWYQQLQGEAPRYLMQVQSDGSYTKRPGVPDRFSGSSSG ADRYLIIPSVQADDEADYYCGADYIGGYVFGGGTQLTVTG |
| 16 | Linker<br>5aa<br>aa 622-626 | GGGSG |
| 15 | Spacer 1<br>9aa<br>aa 627-635 | KPCPPCKCP |
| 54 | CD28 Transmembrane Domain<br>28aa<br>aa 636-663 | MFWVLVVVGGVLACYSLLVTVAFIIFWV |
| 53 | 4-1BB<br>42aa<br>aa 664-705 | KRGRKKLLYIFKQPFMRPVQTTQEEDGCSCRFPEEEEGGCEL |
| 55 | CD3z<br>112aa<br>aa 706-817 | RVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR |
| 61 | CD3z after P2A cleavage | RVKFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPRSGATNFSLLKQAGDVEENPGP (linker-P2A remnant boxed) |
| 56 | SG linker - P2A<br>21aa<br>aa 819-838 | SG-ATNFSLLKQAGDVEENPGP |
| 18 | GMCSFR-alpha-SP<br>22aa<br>aa 839-860 | MLLLVTSLLLCELPHPAFLLIP |

TABLE 7-continued c-Jun-anti-ROR1 CAR sequences
c-Jun-anti-ROR1 CAR

| SEQ ID NO | Description | Sequence |
|---|---|---|
| 62 | GMCSFR-alpha-SP After P2A cleavage | <u>P</u>MLLLVTSLLLCELPHPAFLLIP (P2A remnant residue double underlined |
| 3 | EGFRt 338aa aa 860-1,198 | RKVCNGIGIGEFKDSLSINATNIKHFKNCTSISGDLHILPVAFRGDSFTHTP PLDPQELDILKTVKEITGFLLIQAWPENRTDLHAFENLEIIRGRTKQHGQFS LAVVSLNITSLGLRSLKEISDGDVIISGNKNLCYANTINWKKLFGTSGQKTK IISNRGENSCKATGQVCHALCSPEGCWGPEPRDCVSCRNVSRGRECVDKCNL LEGEPREFVENSECIQCHPECLPQAMNITCTGRGPDNCIQCAHYIDGPHCVK TCPAGVMGENNTLVWKYADAGHVCHLCHPNCTYGCTGPGLEGCPTNGPKIPS IATGMVGALLLLLVVALGIGLFMRRR |
| 58 | Full sequence (with promoter) 4,022 nucleotides | TGAAAGACCCCACCTGTAGGTTTGGCAAGCTAGGATCAAGGTTAGGAACAGA GAGACAGCAGAATATGGGCCAAACAGGATATCTGTGGTAAGCAGTTCCTGCC CCGGCTCAGGGCCAAGAACAGTTGGAACAGCAGAATATGGGCCAAACAGGAT ATCTGTGGTAAGCAGTTCCTGCCCCGGCTCAGGGCCAAGAACAGATGGTCCC CAGATGCGGTCCCGCCCTCAGCAGTTTCTAGAGAACCATCAGATGTTTCCAG GGTGCCCCAAGGACCTGAAATGACCCTGTGCCTTATTTGAACTAACCAATCA GTTCGCTTCTCGCTTCTGTTCGCGCGCTTCTGCTCCCCGAGCTCAATAAAAG AGCCCACAACCCCTCACTCGGCGCGATCAGAACCTCTTACGAGTCGGCTAGC GCCGCCACCATGACAGCCAAGATGGAAACCACATTCTACGACGACGCCCTGA ACGCCTCATTCCTGCCTTCTGAGAGCGGACCTTACGGCTACAGCAATCCTAA GATCCTGAAACAGAGCATGACCCTTAACCTGGCTGATCCTGTTGGAAGCCTG AAACCTCACCTGAGAGCCAAAAACAGCGACCTGCTCACCAGCCCTGATGTGG GCCTGCTGAAGCTGGCCTCTCCAGAGCTGGAACGGCTGATCATCCAGAGCAG CAACGGCCACATCACAACCACCCCTACCCCTACACAATTCCTGTGCCCTAAG AACGTGACCGACGAGCAGGAGGGCTTCGCCGAAGGCTTTGTGCGGGCCCTGG CAGAACTGCACTCTCAGAACACCCTGCCTAGCGTGACCTCCGCCGCCCAGCC TGTCAACGGCGCCGGAATGGTGGCCCCTGCCGTGGCTTCTGTGGCCGGCGGC AGCGGCAGCGGCGGATTCAGCGCCTCTCTGCACTCTGAGCCTCCTGTCTACG CCAATCTGTCTAATTTCAACCCCGGAGCCCTGTCCAGCGGCGGCGGAGCTCC TAGCTACGCGCTGCTGGACTGGCCTTCCCCGCCCAGCCCCAGCAACAGCAG CAGCCTCCACACCACCTGCCCCAGCAGATGCCCGTGCAGCACCCTAGACTGC AGGCCCTGAAGGAAGAACCCCAAACAGTGCCTGAGATGCCTGGCGAGACACC TCCACTGAGCCCCATCGACATGGAAAGCCAGGAGCGGATCAAGGCCGAGAGA AAGAGAATGCGGAACAGAATCGCCGCTAGCAAGTGCAGAAAGCGGAAGCTGG AAAGAATCGCCAGACTGGAAGAGAAGGTGAAGACCCTGAAAGCCCAAAATAG CGAGCTGGCCAGCACCGCCAACATGCTGCGGGAACAGGTGGCCCAGCTGAAG CAGAAGGTGATGAACCACGTGAACTCTGGTTGTCAGCTGATGCTGACCCAGC AGCTCCAGACCTTCGGCTCCGGTGCAACGAACTTCAGCCTGCTGAAGCAGGC CGGAGATGTTGAGGAAAATCCAGGTCCCATGGTCTTGCAGACTCAAGTATTT ATATCCCTTTTGCTCTGGATCTCTGGAGCTTACGGCCAGGAACAGCTCGTCG AAAGCGGCGGCAGACTGGTGACACCTGGCGGCAGCCTGACCCTGAGCTGCAA GGCCAGCGGCTTCGACTTCAGCGCCTACTACATGAGCTGGGTCCGCCAGGCC CCTGGCAAGGGACTGGAATGGATCGCCACCATCTACCCCAGCAGCGGCAAGA CCTACTACGCCACCTGGGTGAACGGACGGTTCACCATCTCCAGCGACAACGC CCAGAACACCGTGGACCTGCAGATGAACAGCCTGACAGCCGCCGACCGGGCC ACCTACTTTTGCGCTCGGGACAGCTACGCCGACGACGGCGCCCTGTTCAACA TCTGGGGCCCTGGCACCCTGGTGACAATCTCTAGCGGCGGAGGCGGATCTGG TGGCGGAGGAAGTGGCGGCGGAGGATCTGAGCTGGTGCTGACCCAGAGCCCC TCTGTGTCTGCTGCCCTGGGAAGCCCTGCCAAGATCACCTGTACCCTGAGCA GCGCCCACAAGACCGACACCATCGACTGGTATCAGCAGCTGCAGGGCGAGGC CCCCAGATACCTGATGCAGGTGCAGAGCGACGGCAGCTACACCAAGAGGCCA GGCGTGCCCGACAGGTTCAGCGGATCTAGCTCTGGCGCCGACCGCTACCTGA TCATCCCCAGCGTGCAGGCCGATGACGAGGCCGATTACTACTGTGGCGCCGA CTACATCGGCGGCTACGTGTTCGGCGGAGGCACCCAGCTGACCGTGACCGGT GGCGGAGGTTCAGGCAAACCGTGCCCTCCGTGCAAGTGTCCTATGTTCTGGG TGCTGGTGGTGGTCGGAGGCGTGCTGGCCTGCTACAGCCTGCTGGTCACCGT GGCCTTCATCATCTTTTGGGTGAAACGGGGCAGAAAGAAACTCCTGTATATA TTCAAACAACCATTTATGAGACCAGTACAAACTACTCAAGAGGAAGATGGCT GTAGCTGCCGATTTCCAGAAGAAGAAGAAGGAGGATGTGAACTGCGGGTGAA GTTCAGCAGAAGCGCCGACGCCCCTGCCTACCAGCAGGGCCAGAATCAGCTG TACAACGAGCTGAACCTGGGCAGAAGGGAAGAGTACGACGTCCTGGATAAGC GGAGAGGCCGGGACCCTGAGATGGGCGGCAAGCCTCGGCGGAAGAACCCCCA GGAAGGCCTGTATAACGAACTGCAGAAAGACAAGATGGCCGAGGCCTACAGC GAGATCGGCATGAAGGGCGAGCGGAGGCGGGGCAAGGGCCACGACGGCCTGT ATCAGGGCCTGTCCACCGCCACCAAGGATACCTACGACGCCCTGCACATGCA GGCCCTGCCCCCAAGGTCGGAGCCACTAACTTCTCCCTGTTGAAACAAGCA GGGGATGTCGAAGAGAATCCCGGGCCAATGCTTCTCCTGGTGACAAGCCTTC TGCTCTGTGAATTACCACACCCAGCATTCCTCCTGATCCCACGCAAAGTGTG CAACGGAATAGGTATTGGTGAATTTAAGGACTCACTCTCCATAAATGCTACG AATATTAAACACTTCAAAAACTGCACCTCCATCAGTGGCGATCTCCACATCC TGCCGGTGGCATTTAGGGGTGACTCCTTCACACATACTCCTCCTCTGGACCC |

TABLE 7-continued c-Jun-anti-ROR1 CAR sequences
c-Jun-anti-ROR1 CAR

| SEQ ID NO | Description | Sequence |
|---|---|---|
| | | ACAAGAACTGGATATTCTGAAAACCGTAAAGGAAATCACAGGGTTTTTGCTG<br>ATTCAAGCTTGGCCTGAAAACAGGACGGACCTCCATGCCTTTGAGAACCTAG<br>AAATCATACGCGGCAGGACCAAGCAGCATGGACAGTTTTCTCTTGCTGTCGT<br>GAGCCTGAACATAACATCCTTGGGATTACGCTCCCTCAAGGAGATAAGTGAT<br>GGAGATGTGATAATTTCAGGAAACAAAAATTTGTGCTATGCAAATACAATAA<br>ACTGGAAAAAACTGTTTGGGACCTCCGGCCAGAAAACCAAAATTATAAGCAA<br>CAGAGGCGAAAACAGCTGCAAGGCCACAGGCCAGGTCTGCCATGCCTTGTGC<br>TCCCCCGAGGGCTGCTGGGGCCCGGAGCCCAGGGATTGCGTGTCTTGCCGGA<br>ATGTCAGCCGAGGCAGGGAATGCGTGGACAAGTGCAACCTTCTGGAAGGCGA<br>GCCAAGGGAGTTTGTGGAGAACTCTGAGTGCATACAGTGCCACCCAGAGTGC<br>CTGCCTCAGGCCATGAACATCACCTGCACAGGACGGGGACCAGACAACTGTA<br>TCCAGTGTGCCCACTACATTGACGGCCCCCACTGCGTCAAGACCTGCCCGGC<br>AGGAGTCATGGGAGAAAACAACACCCTGGTCTGGAAGTACGCAGACGCCGGC<br>CATGTGTGCCACCTGTGCCATCCAAACTGCACCTACGGATGCACTGGGCCAG<br>GTCTTGAAGGCTGTCCAACGAACGGGCCTAAGATCCCGTCCATCGCCACTGG<br>GATGGTGGGGCCCTCCTCTTGCTGCTGGTGGTGGCCCTGGGGATCGGCCTC<br>TTCATGCGCCGAAGGTGA |
| 64 | MND Promoter | TGAAAGACCCCACCTGTAGGTTTGGCAAGCTAGGATCAAGGTTAGGAACAGA<br>GAGACAGCAGAATATGGGCCAAACAGGATATCTGTGGTAAGCAGTTCCTGCC<br>CCGGCTCAGGGCCAAGAACAGTTGGAACAGCAGAATATGGGCCAAACAGGAT<br>ATCTGTGGTAAGCAGTTCCTGCCCCGGCTCAGGGCCAAGAACAGATGGTCCC<br>CAGATGCGGTCCCGCCCTCAGCAGTTTCTAGAGAACCATCAGATGTTTCCAG<br>GGTGCCCCAAGGACCTGAAATGACCCTGTGCCTTATTTGAACTAACCAATCA<br>GTTCGCTTCTCGCTTCTGTTCGCGCGCTTCTGCTCCCCGAGCTCAATAAAAG<br>AGCCCACAACCCCTCACTCGGC |

Example 1

Analysis of the Ability of Anti-ROR1 CAR T Cells Overexpressing c-Jun to Kill Tumor Cells To begin characterizing the ROR1-dependent biological activity of the anti-ROR1 CAR T cells described herein (e.g., overexpressing c-Jun), the ability of the CAR T cells to kill tumor cells was assessed. Briefly, the anti-ROR1 CAR T cells overexpressing c-Jun (referred to herein as "c-Jun overexpressing anti-ROR1 CAR T cells") were coincubated with either ROR1+ NSCLC cell line ("$H_{1975}$") or $H_{1975}$ with human ROR1 knocked-out via clustered regularly interspaced short palindromic repeats (CRISPR)/CRISPR-associated protein 9 (Cas9) ("$H_{1975}$-ROR1KO"). As a comparison, untransduced "mock" T cells (i.e., does not express anti-ROR1 scFv), which should not lyse the tumor cells, and "control" anti-ROR1 CAR T cells, which do not overexpress c-Jun, were also coincubated with either $H_{1975}$ or $H_{1975}$-ROR1KO cells. Both the $H_{1975}$ and $H_{1975}$-ROR1KO cells expressed NucLight Red (NLR; nuclear-restricted mKate2), so that the non-lysed cells can be quantified. The different CAR T cells were incubated at an effector-to-target (E:T) cell ratio of 1:1 for 120 hours.

As shown in FIG. 1A, the c-Jun overexpressing-anti-ROR1 CART cells mediated cytolysis of tumor cells in a ROR1 expression-dependent manner, similar to the control anti-ROR1 CAR T cells. Importantly, no killing of target-negative $H_{1975}$-ROR1 knock out cells by the anti-ROR1 CAR T cells were observed (FIG. 1B). These results demonstrate that the anti-ROR1 CAR T cells overexpressing c-Jun are as efficient at killing tumor cells compared to the more traditional anti-ROR1 CAR T cells (e.g., that do not overexpress c-Jun).

Example 2

Analysis of the Ability of Anti-ROR1 CAR T Cells Overexpressing c-Jun to Produce Selective Cytokine Secretion To further characterize the functional capabilities of the anti-ROR1 CAR T cells described herein, -anti-ROR1 CAR T cells overexpressing c-Jun or control anti-ROR1 CAR T cells (i.e., does not overexpress c-Jun) were coincubated with $H_{1975}$ or $H_{1975}$-ROR1KO tumor cells for 24 hours at an effector-to-target (E:T) cell ratio of 1:1 for 24 hours. Afterwards, supernatant was collected from the different incubation conditions for IL-2 and IFN-γ quantification. The concentrations of the cytokines were measured using the Meso Scale Discovery (MSD) U-Plex.

Figure 2A:
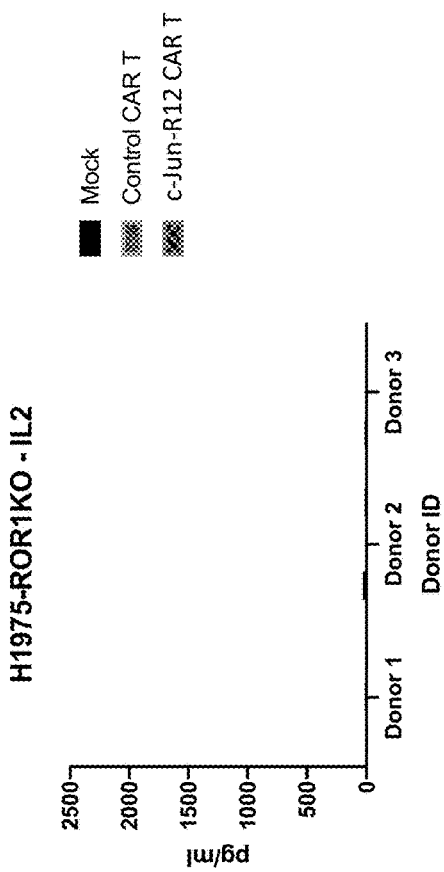
Figure 2B:
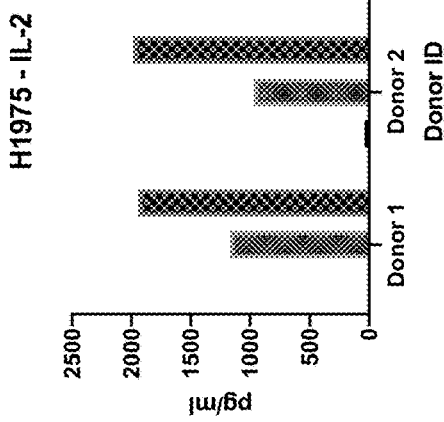
Figure 2C:
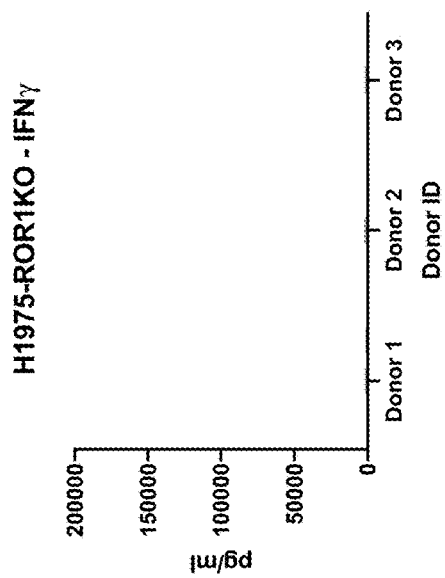
Figure 2D:
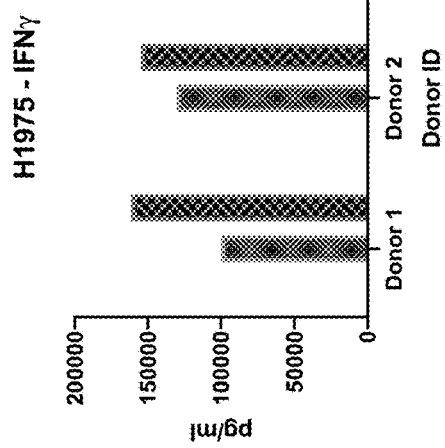

As shown in FIGS. 2A and 2C, in response to the ROR1 antigen, both the control anti-ROR1 CAR T cells and the c-Jun overexpressing-anti-ROR1 CAR T cells produced significant amounts of both IL-2 and IFN-γ. However, the cytokine production was much greater in anti-ROR1 CAR T cells overexpressing c-Jun. Cytokines were not secreted by the control anti-ROR1 CAR T cells or c-Jun overexpressing-anti-ROR1 CAR T when cultured in the presence of $H_{1975}$-ROR1KO cells (FIGS. 2B and 2D).

Collectively, these data demonstrated the selective biological activity of c-Jun overexpressing-anti-ROR1 CAR T cells, in that c-Jun overexpressing-anti-ROR1 CAR T cells only lyses tumor cells and secretes cytokines in an antigen-dependent manner. In addition, target-dependent cytokine secretion by c-Jun overexpressing-anti-ROR1 CAR T cells was enhanced compared with control anti-ROR1 CAR-T cells that do not overexpress c-Jun.

Example 3

Analysis of Cytokine-Dependent Proliferation of Anti-ROR1 CAR T Cells Overexpressing c-Jun To determine if the overexpression of c-Jun had any effect on the sensitivity of the anti-ROR1 CAR T cells to cytokines, the control anti-ROR1 CAR T cells (e.g., not overexpressing c-Jun) and c-Jun overexpressing-anti-ROR1 CAR T cells were separately cultured in a Grex 24 well plate ($1\times10^6$ cells/well) under one of the following conditions: (i) T-cell media (OpTmizer Basal Medium, OpTmizer Cell Supplement, Immune Cell Serum Replacement, 2-mM L-glutamine, 1×GlutaMAX) alone, (ii) T-cell media supplemented with 200 IU/ml of IL-2, or (iii) T-cell media supplemented with 1200 IU/ml IL-7 and 200 IU/mL IL-15. Non-transduced ("mock") cells were also cultured under these conditions and used as control. On Days 7 and 14, the total number of T cells in each culture condition were counted, and cells from day 7 were then reseeded at $1\times10^6$ cells/well for the subsequent rounds of culture. Media conditions were maintained for each sample throughout the length of the assay.

As shown in FIG. 3A, in the absence of cytokine, none of the T cells were able to expand. Compared to mock or control anti-ROR1 CAR T cells that transiently expanded to limited numbers with the cytokine support, c-Jun overexpressing-anti-ROR1 CAR T cells exhibited superior proliferative capacity that was maintained throughout the study (FIGS. 3B and 3C). These results further demonstrate that the overexpression of c-Jun can improve various functional properties (e.g., cytokine sensitivity) of the anti-ROR1 CAR T cells.

Example 4

Analysis of the Effect of c-Jun Overexpression on the Anti-Tumor Properties of Anti-ROR1 CAR T Cells Following Chronic Antigen Stimulation In chronic infection and cancer, T cells can become exhausted through persistent antigen exposure leading to progressive loss of T-cell effector functions, such as cytolytic activity and cytokine secretion. Therefore, to assess whether the overexpression of c-Jun had any effect on the effector function of anti-ROR1 CAR T cells after prolonged antigen stimulation, c-Jun overexpressing-anti-ROR1 CAR T cells and control anti-ROR1 CAR T cells (e.g., not overexpressing c-Jun) were chronically stimulated with repeated exposure to RORVA549 NSCLC tumor cells. Chronic antigen exposure was ensured by re-plating the CAR T cells with fresh target cells at a 1:1 E:T ratio every 2 days. On Day 7 post chronic stimulation, the CAR T cells were collected and coincubated with either A549-NLR (E:T cell ratio 1:1) or $H_{1975}$-NLR (E:T 1:5). Lysis of target cells was evaluated by tracking total NLR intensity, normalized to time 0 h of assay setup. 24-h supernatants were collected for IFN-γ, IL-2, and TNF-α quantification by MSD.

As shown in FIG. 4A, even after repeated antigen stimulation, the c-Jun overexpressing anti-ROR1 CAR T cells were able to effectively lyse the ROR1+ tumor cells compared to the control anti-ROR1 CAR T cells (e.g., not overexpressing c-Jun). Similarly, the c-Jun overexpressing-anti-ROR1 CART cells also produced increased levels of at least IFN-γ (FIG. 4B). These results demonstrate that the overexpression of c-Jun can help CAR T cells maintain effector function in the presence of chronic antigen stimulation.

Example 5

Analysis of Exhaustion-Associated Transcriptional Profile in Chronically Stimulated Anti-ROR1 CAR T Cells Overexpressing c-Jun To further understand the effect of c-Jun overexpression on T cell exhaustion, bulk RNA-sequencing was performed on CAR+ T cells from the 7-day chronic stimulation time point (n=3 donors, described in FIG. 5A) and genes that were differentially expressed between Control anti-ROR1 CAR T cells (e.g., not overexpressing c-Jun) and c-Jun overexpressing-anti-ROR1 CAR T cells were identified. Gene set enrichment analysis (GSEA) on the differentially expressed genes using gene sets from models of T cell exhaustion from the literature (Beltra J C, et al., Immunity. 2020; 52(5):825-841.e8; Zhang L, et al., Nature. 2018; 564(7735):268-272) showed that genes that were down-regulated in c-Jun overexpressing-anti-ROR1 CAR T cells were significantly enriched for gene sets up-regulated in (Texterm_UP [gene set from Beltra 2020] and Tex_multi-Tumors [gene set from Zhang 2018]). Conversely, genes up-regulated in c-Jun overexpressing-anti-ROR1 CAR T cells were significantly enriched for a gene set containing T-cell proliferation genes (TexProg2_UP [gene set from Beltra 2020]) and a gene set down-regulated in a terminal exhaustion phenotype (Texterm DOWN [gene set from Beltra 2020]) (FIG. 5A). Together these data indicate the impact of c-Jun on reducing the exhaustion gene expression signature and maintaining expression of genes associated with T-cell proliferation.

To better understand the impact of c-Jun, single-cell cellular indexing of transcriptomes and epitopes (CITE)-seq was also performed on the Day 7 CAR+ T cells in 2 donors (FIG. 5B-FIG. 5D). Clustering of cells based on transcriptional (and protein) profile helped identify cluster 3 (FIG. 5B) that had cells predominantly enriched for literature-based exhaustion markers. The frequency of cluster 3 was decreased in both donors with addition of c-Jun illustrating the effect of c-Jun on exhaustion (FIG. 5D). In addition, clusters 0 and 5 (FIG. 5B), which were enriched for more differentiated/activated markers (such as 4-1BB, granzyme A [GZMA] (FIG. 5C)) were also decreasing in frequency with addition of c-Jun (FIG. 5D).

Example 6

Analysis of the Reactivit), of Anti-ROR1 CAR T Cells Overexpressing c-Jun to NSCLC Cell Lines Expressing Low Levels of ROR1

To assess whether c-Jun overexpression has any effect on the anti-ROR1 CAR T cells to recognize antigen, c-Jun overexpressing-anti-ROR1 CAR T cells and control-anti-ROR1 CAR T cells (i.e., not overexpressing c-Jun) were coincubated with $H_{1975}$ cells engineered to express varying levels of cell surface ROR1 (FIG. 6). A set of mutated encephalomyocarditis virus internal ribosome entry site elements with varying strengths was used to control the relative expression of human ROR1 over a wide range and introduced into the $H_{1975}$-ROR1KO cell line (Koh 2013. PLoS One, 8(12):e82100.doi:10.1371). The expression levels of ROR1 by the cell lines are represented as geometric MFI (FIG. 6). The cells were coincubated over a course of 148 hours, and at various time points, the total number of NLR-positive cells were counted and normalized to the count at time point 0 h to calculate normalized target killing. At 24 hours post initial antigen stimulation, supernatant was collected and the amounts of IL-2 and IFN-γ were also quantified using Meso Scale Discovery (MSD) U-Plex.

As shown in FIG. 7, c-Jun overexpressing-anti-ROR1 CAR T Cells and control-anti-ROR1 CAR T cells (e.g., not overexpressing c-Jun) lysed the $H_{1975}$ cells at a similar rate regardless of ROR1 antigen density. Similar results were observed when IL-2 and IFN-γ levels were quantified (FIGS. 8A and 8B). These results suggest that c-Jun overexpression does not substantially alter the antigen density threshold required for the anti-ROR1 CAR T cells to exert effector function.

Example 7

Analysis of the In Vivo Anti-Tumor Efficacy of-Anti-ROR1 CAR T Cells Overexpressing c-Jun To assess whether the overexpression of c-Jun can also improve various functional properties of CART cells in vivo, the anti-tumor activity of c-Jun overexpressing-anti-ROR1 CAR T cells were tested in a xenograft animal model. Briefly, tumor cells (i.e., ROR1-positive $H_{1975}$ NSCLC cell line) were implanted subcutaneously over the flank of NOD scid gamma; NOD.Cg-Prkdcscid Il2rgtm1Wjl/SzJ (NSG) mice. When tumors reached ~100 mm³, mice were intravenously infused with one of the following: (i) untransduced mock T cells, (ii) control anti-ROR1 CART cells (e.g., not overexpressing c-Jun), or (iii) c-Jun overexpressing-anti-ROR1 CAR T cells. Anti-tumor activity was assessed by measuring tumor volume using calipers and treatment-related toxicity was assessed by measuring animal body weight. Additionally, expansion of the T cells was assessed using flow cytometry of peripheral blood collected weekly starting 24 hours after T-cell infusion for a total of 6 weeks.

As shown in FIGS. 9A and 9C, animals treated with the control anti-ROR1 CAR T cells (e.g., not overexpressing c-Jun) appeared to control tumor growth initially but eventually succumbed to the tumor, with only about 40% of the animals surviving to the end of the experiment. In contrast, animals treated with c-Jun overexpressing-anti-ROR1 CAR T cells (e.g., overexpressing c-Jun) showed significantly greater tumor control and survived throughout the entire duration of the experiment. In agreement with the improved anti-tumor data, the c-Jun overexpressing-anti-ROR1 CAR T cells (e.g., overexpressing c-Jun) also exhibited much greater persistence and expansion compared to the control anti-ROR1 CAR T cells (e.g., not overexpressing c-Jun) (FIG. 10). These results confirm the earlier in vitro data and demonstrate that the c-Jun overexpressing anti-ROR1 CAR T cells described herein exhibit much improved anti-tumor effects compared to the more traditional anti-ROR1 CAR T cells (e.g., not overexpressing c-Jun).

Example 8

Clinical Development

A FIH, Phase 1, single-arm, open-label, dose-escalation and -expansion, multicenter study designed to evaluate the safety, PK, and antitumor activity of c-Jun overexpressing-anti-ROR1 CAR T cell in patients with ROR1-positive relapsed and/or refractory TNBC and NSCLC will be conducted. The primary objectives of the Phase 1 study are to evaluate the safety and tolerability of c-Jun overexpressing-anti-ROR1 CAR T cell in patients with relapsed/refractory TNBC and NSCLC, and to determine the RP2D of c-Jun overexpressing anti-ROR1 CAR T cell. The secondary objections of the Phase 1 study are to evaluate the antitumor activity of c-Jun overexpressing anti-ROR1 CAR T cell and to evaluate the PK (e.g., expansion and persistence) in peripheral blood samples of c-Jun overexpressing anti-ROR1 CAR T cell.

Proposed Phase 1 Design

This will be a single-arm, open label, dose escalation and expansion, multi-center study designed to evaluate the safety, PK, and antitumor activity of c-Jun overexpressing-anti-ROR1 CAR T cells in patients with relapsed and/or refractory TNBC and NSCLC. During the dose escalation phase only participants with TNBC will be enrolled; during expansion phase, enrollment will occur to both the TNBC and NSCLC study cohorts.

Participants who are ROR1-positive by immunohistochemistry, with TNBC that has failed 2 lines of therapy, including checkpoint inhibitors and abraxane, or with NSCLC that has failed 2 lines of therapy, including targeted therapies for those with EGFR⁺ and ALK⁺ disease, in addition to other eligibility criteria, will be eligible to enroll. Participants who meet all eligibility criteria will be enrolled and will undergo leukapheresis to enable product generation. Following successful product manufacturing, participants will enter the treatment phase and will receive 1 cycle of treatment. A treatment cycle will include lymphodepleting chemotherapy with fludarabine and cyclophosphamide for 3 days, followed by a single dose of cell product at one of the protocol-defined dose levels, administered IV. The cell product will be administered several days after completion of lymphodepleting chemotherapy unless, after discussion with the medical monitor, clinical or logistical circumstances require modification of this timing to a later date.

Participants will be followed for up to 2 years after cell product administration for safety, disease status, additional anticancer therapies, and survival. All participants who receive c-Jun overexpressing-anti-ROR1 CAR T cells will be asked to enroll in a sponsored long-term follow-up (LTFU) study at the time of completion or discontinuation from this study.

What is claimed is:

1. A polynucleotide encoding a chimeric polypeptide which comprises the amino acid sequence set forth in SEQ ID NO: 57.

2. A polynucleotide comprising the nucleotide sequence set forth in SEQ ID NO: 5.8.

3. A polynucleotide comprising the nucleotide sequence set forth at 426 to 4,022 of the nucleotide sequence set forth in SEQ ID NO: 58.

4. The polynucleotide of claim 3, which further comprises a promoter.

5. A vector comprising the polynucleotide of claim 1.

6. A modified cell comprising the polynucleotide of claim 1.

7. A pharmaceutical composition comprising the modified cell of claim 6 and a pharmaceutically acceptable carrier.

8. A method of preparing a cell expressing a chimeric antigen receptor (CAR) comprising transfecting a cell with the polynucleotide of claim 1.

9. The polynucleotide of claim 4, wherein the promoter comprises a MND promoter.

10. A vector comprising the polynucleotide of claim 2.

11. A vector comprising the polynucleotide of claim 3.

12. A composition comprising the vector of claim 10 and a carrier.

13. A composition comprising the vector of claim 11 and a carrier.

14. A composition comprising the vector of claim 5 and a carrier.

15. A modified cell comprising the polynucleotide of claim 2.

16. A modified cell comprising the polynucleotide of claim 3.

17. A pharmaceutical composition comprising the modified cell of claim 15 and a pharmaceutically acceptable carrier.

18. A pharmaceutical composition comprising the modified cell of claim 16 and a pharmaceutically acceptable carrier.

19. A method of preparing a cell expressing a chimeric antigen receptor (CAR) comprising transfecting a cell with the polynucleotide of claim 2.

20. A method of preparing a cell expressing a chimeric antigen receptor (CAR) comprising transfecting a cell with the polynucleotide of claim 3.

* * * * *

SEQUENCE LISTING

<160> NUMBER OF SEQ ID NOS: 64

<210> SEQ ID NO 1
<211> LENGTH: 331
<212> TYPE: PRT
<213> ORGANISM: artificial sequence
<220> FEATURE:
<223> OTHER INFORMATION: wild type human c-Jun protein

<400> SEQUENCE: 1

```
Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
            35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
            115                 120                 125

Ser Val Thr Ser Ala Ala Gln Pro Val Asn Gly Ala Gly Met Val Ala
    130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
            195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
            275                 280                 285

Ala Gln Asn Ser Glu Leu Ala Ser Thr Ala Asn Met Leu Arg Glu Gln
    290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330
```

<210> SEQ ID NO 2
<211> LENGTH: 3257
<212> TYPE: DNA
<213> ORGANISM: artificial sequence
<220> FEATURE:
<223> OTHER INFORMATION: wild type human c-Jun gene

<400> SEQUENCE: 2

```
gctcagagtt gcactgagtg tggctgaagc agcgaggcgg gagtggaggt gcgcggagtc      60
aggcagacag acagacacag ccagccagcc aggtcggcag tatagtccga actgcaaatc    120
```

```
ttatttttctt ttcaccttct ctctaactgc ccagagctag cgcctgtggc tcccgggctg    180
gtgtttcggg agtgtccaga gagcctggtc tccagccgcc cccggagga gagccctgct     240 gcccaggcgc tgttgacagc ggcggaaagc agcggtaccc acgcgcccgc cgggggaagt    300
cggcgagcgg ctgcagcagc aaagaacttt cccggctggg aggaccggag acaagtggca    360
gagtcccgga gccaactttt gcaagccttt cctgcgtctt aggcttctcc acggcggtaa    420
agaccagaag gcggcggaga gccacgcaag agaagaagga cgtgcgctca gcttcgctcg    480
caccggttgt tgaacttggg cgagcgcgag ccgcggctgc cgggcgcccc ctcccctag     540 cagcggagga ggggacaagt cgtcggagtc cgggcggcca agacccgccg ccggccggcc    600
actgcagggt ccgcactgat ccgctccgcg gggagagccg ctgctctggg aagtgagttc    660
gcctgcggac tccgaggaac cgctgcgcac gaagagcgct cagtgagtga ccgcgacttt    720
tcaaagccgg gtagcgcgcg cgagtcgaca agtaagagtg cgggaggcat cttaattaac    780
cctgcgctcc ctggagcgag ctggtgagga gggcgcagcg gggacgacag ccagcgggtg    840
cgtgcgctct tagagaaact ttccctgtca aaggctccgg ggggcgcggg tgtcccccgc    900
ttgccacagc cctgttgcgg ccccgaaact tgtgcgcgca gcccaaacta acctcacgtg    960
aagtgacgga ctgttctatg actgcaaaga tggaaacgac cttctatgac gatgccctca    1020
acgcctcgtt cctcccgtcc gagagcggac cttatggcta cagtaacccc aagatcctga    1080
aacagagcat gaccctgaac ctggccgacc cagtggggag cctgaagccg cacctccgcg    1140
ccaagaactc ggacctcctc acctcgcccg acgtggggct gctcaagctg gcgtcgcccg    1200
agctggagcg cctgataatc cagtccagca acgggcacat caccaccacg ccgaccccca    1260
cccagttcct gtgccccaag aacgtgacag atgagcagga gggcttcgcc gagggcttcg    1320
tgcgcgccct ggccgaactg cacagccaga acacgctgcc cagcgtcacg tcggcggcgc    1380
agccggtcaa cggggcaggc atggtggctc ccgcggtagc ctcggtgcca ggggggcagcg   1440 gcagcggcgg cttcagcgcc agcctgcaca gcagccgcg ggtctacgca aacctcagca    1500
acttcaaccc aggcgcgctg agcagcggcg gcggggcgcc ctcctacggc gcggccggcc    1560 tggccttttcc cgcgcaaccc cagcagcagc agcagccgcg caccacctg ccccagcaga    1620 tgcccgtgca gcacccgcgg ctgcaggccc tgaaggagga gcctcagaca gtgcccgaga    1680
tgcccggcga gacaccgccc ctgtccccca tcgacatgga gtcccaggag cggatcaagg    1740
cggagaggaa gcgcatgagg aaccgcatcg ctgcctccaa gtgccgaaaa aggaagctgg    1800
agagaatcgc ccgctggag gaaaaagtga aaccttgaa agctcagaac tcggagctgg     1860
cgtccacggc caacatgctc agggaacagg tggcacagct taaacagaaa gtcatgaacc    1920
acgttaacag tgggtgccaa ctcatgctaa cgcagcagtt gcaaacattt tgaagagaga    1980
ccgtcggggg ctgaggggca acgaagaaaa aaaataacac agagagacag acttgagaac    2040
ttgacaagtt gcgacggaga gaaaaaagaa gtgtccgaga actaaagcca agggtatcca    2100
agttggactg ggttgcgtcc tgacggcgcc cccagtgtgc acgagtggga aggacttggc    2160
gcgccctccc ttggcgtgga gccagggagc ggccgcctgc gggctgcccc gctttgcgga    2220
cgggctgtcc ccgcgcgaac ggaacgttgg acttttcgtt aacattgacc aagaactgca    2280
tggacctaac attcgatctc attcagtatt aagggggga ggggagggg gttacaaact     2340 gcaatagaga ctgtagattg cttctgtagt actccttaag aacacaaagc gggggaggg    2400 ttggggaggg gcggcaggag ggaggtttgt gagagcgagg ctgagcctac agatgaactc    2460
```

```
tttctggcct gccttcgtta actgtgtatg tacatatata tatttttttaa tttgatgaaa    2520 gctgattact gtcaataaac agcttcatgc ctttgtaagt tatttcttgt ttgtttgttt    2580
gggtatcctg cccagtgttg tttgtaaata agagatttgg agcactctga gtttaccatt    2640
tgtaataaag tatataattt ttttatgttt tgtttctgaa aattccagaa aggatattta    2700
agaaaataca ataaactatt ggaaagtact cccctaacct cttttctgca tcatctgtag    2760
atactagcta tctaggtgga gttgaaagag ttaagaatgt cgattaaaat cactctcagt    2820
gcttcttact attaagcagt aaaaactgtt ctctattaga ctttagaaat aaatgtacct    2880
gatgtacctg atgctatggt caggttatac tcctcctccc ccagctatct atatggaatt    2940
gcttaccaaa ggatagtgcg atgtttcagg aggctggagg aagggggggtt gcagtggaga    3000 gggacagccc actgagaagt caaacatttc aaagtttgga ttgtatcaag tggcatgtgc    3060
tgtgaccatt tataatgtta gtagaaattt tacaataggg gcttattctc aaagcaggaa    3120
ttggtggcag attttacaaa agatgtatcc ttccaatttg gaatcttctc tttgacaatt    3180
cctagataaa aagatggcct ttgcttatga atatttataa cagcattctt gtcacaataa    3240
atgtattcaa ataccaa                                                  3257

<210> SEQ ID NO 3
<211> LENGTH: 338
<212> TYPE: PRT
<213> ORGANISM: artificial sequence
<220> FEATURE:
<223> OTHER INFORMATION: epidermal growth factor receptor protein opt
      (EGFRopt)

<400> SEQUENCE: 3

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
```

```
                210                 215                 220
Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
                260                 265                 270

Leu Val Trp Lys Tyr Ala Asp Ala Gly His Val Cys His Leu Cys His
                275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met Arg
                325                 330                 335

Arg Arg

<210> SEQ ID NO 4

<400> SEQUENCE: 4

000

<210> SEQ ID NO 5
<211> LENGTH: 353
<212> TYPE: PRT
<213> ORGANISM: artificial sequence
<220> FEATURE:
<223> OTHER INFORMATION: Uniprot: P01876, IGHA1_HUMAN, immunoglobulin
      heavy constant alpha 1

<400> SEQUENCE: 5

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
            35                  40                  45

Thr Ala Arg Asn Phe Pro Pro Ser Gln Asp Ala Ser Gly Asp Leu Tyr
        50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser Cys Cys His Pro Arg Leu Ser
            115                 120                 125

Leu His Arg Pro Ala Leu Glu Asp Leu Leu Leu Gly Ser Glu Ala Asn
        130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190
```

```
Ala Glu Pro Trp Asn His Gly Lys Thr Phe Thr Cys Thr Ala Ala Tyr
            195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 6
<211> LENGTH: 340
<212> TYPE: PRT
<213> ORGANISM: artificial sequence
<220> FEATURE:
<223> OTHER INFORMATION: Uniprot P01877, IGHA2_HUMAN, immunoglobulin
      heavy constant alpha 2

<400> SEQUENCE: 6

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190
```

```
Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
                260                 265                 270

Ser Gln Gly Thr Thr Thr Tyr Ala Val Thr Ser Ile Leu Arg Val Ala
                275                 280                 285

Ala Glu Asp Trp Lys Lys Gly Glu Thr Phe Ser Cys Met Val Gly His
        290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
                325                 330                 335

Gly Thr Cys Tyr
            340

<210> SEQ ID NO 7
<211> LENGTH: 398
<212> TYPE: PRT
<213> ORGANISM: artificial sequence
<220> FEATURE:
<223> OTHER INFORMATION: Uniprot P01665, GCAM_MOUSE, immunoglobulin
      gamma 2A chain C region

<400> SEQUENCE: 7

Lys Thr Thr Ala Pro Ser Val Tyr Pro Leu Ala Pro Val Cys Gly Asp
1               5                   10                  15

Thr Thr Gly Ser Ser Val Thr Leu Gly Cys Leu Val Lys Gly Tyr Phe
                20                  25                  30

Pro Glu Pro Val Thr Leu Thr Trp Asn Ser Gly Ser Leu Ser Ser Gly
            35                  40                  45

Val His Thr Phe Pro Ala Val Leu Gln Ser Asp Leu Tyr Thr Leu Ser
        50                  55                  60

Ser Ser Val Thr Val Thr Ser Ser Thr Trp Pro Ser Gln Ser Ile Thr
65                  70                  75                  80

Cys Asn Val Ala His Pro Ala Ser Ser Thr Lys Val Asp Lys Lys Ile
                85                  90                  95

Glu Pro Arg Gly Pro Thr Ile Lys Pro Cys Pro Pro Cys Lys Cys Pro
                100                 105                 110

Ala Pro Asn Leu Leu Gly Gly Pro Ser Val Phe Ile Phe Pro Pro Lys
            115                 120                 125

Ile Lys Asp Val Leu Met Ile Ser Leu Ser Pro Ile Val Thr Cys Val
        130                 135                 140

Val Val Asp Val Ser Glu Asp Asp Pro Asp Val Gln Ile Ser Trp Phe
145                 150                 155                 160

Val Asn Asn Val Glu Val His Thr Ala Gln Thr Gln Thr His Arg Glu
                165                 170                 175

Asp Tyr Asn Ser Thr Leu Arg Val Val Ser Ala Leu Pro Ile Gln His
            180                 185                 190

Gln Asp Trp Met Ser Gly Lys Glu Phe Lys Cys Lys Val Asn Asn Lys
        195                 200                 205
```

```
Asp Leu Pro Ala Pro Ile Glu Arg Thr Ile Ser Lys Pro Lys Gly Ser
    210                 215                 220

Val Arg Ala Pro Gln Val Tyr Val Leu Pro Pro Glu Glu Glu Met
225                 230                 235                 240

Thr Lys Lys Gln Val Thr Leu Thr Cys Met Val Thr Asp Phe Met Pro
                    245                 250                 255

Glu Asp Ile Tyr Val Glu Trp Thr Asn Asn Gly Lys Thr Glu Leu Asn
                260                 265                 270

Tyr Lys Asn Thr Glu Pro Val Leu Asp Ser Asp Gly Ser Tyr Phe Met
            275                 280                 285

Tyr Ser Lys Leu Arg Val Glu Lys Lys Asn Trp Val Glu Arg Asn Ser
        290                 295                 300

Tyr Ser Cys Ser Val Val His Glu Gly Leu His Asn His His Thr Thr
305                 310                 315                 320

Lys Ser Phe Ser Arg Thr Pro Gly Leu Asp Leu Asp Asp Val Cys Ala
                325                 330                 335

Glu Ala Gln Asp Gly Glu Leu Asp Gly Leu Trp Thr Thr Ile Thr Ile
                340                 345                 350

Phe Ile Ser Leu Phe Leu Leu Ser Val Cys Tyr Ser Ala Ser Val Thr
            355                 360                 365

Leu Phe Lys Val Lys Trp Ile Phe Ser Ser Val Glu Leu Lys Gln
        370                 375                 380

Thr Ile Ser Pro Asp Tyr Arg Asn Met Ile Gly Gln Gly Ala
385                 390                 395

<210> SEQ ID NO 8
<211> LENGTH: 330
<212> TYPE: PRT
<213> ORGANISM: artificial sequence
<220> FEATURE:
<223> OTHER INFORMATION: Uniprot P01857, IGHG1_HUMAN, immunoglobulin
      heavy constant gamma 1

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 9
<211> LENGTH: 326
<212> TYPE: PRT
<213> ORGANISM: artificial sequence
<220> FEATURE:
<223> OTHER INFORMATION: Uniprot P01859, IGHG2_HUMAN, immunoglobulin
      heavy constant gamma 2

<400> SEQUENCE: 9

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 10
<211> LENGTH: 377
<212> TYPE: PRT
<213> ORGANISM: artificial sequence
<220> FEATURE:
<223> OTHER INFORMATION: Uniprot P01860, IGHG3_HUMAN, immunoglobulin
      heavy constant gamma 3

<400> SEQUENCE: 10

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220
```

```
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Phe Thr Gln
    355                 360                 365

Lys Ser Leu Ser Leu Ser Pro Gly Lys
370                 375

<210> SEQ ID NO 11
<211> LENGTH: 327
<212> TYPE: PRT
<213> ORGANISM: artificial sequence
<220> FEATURE:
<223> OTHER INFORMATION: Uniprot P01861, IGHG4, immunoglobulin heavy
      constant gamma 4

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 384
<212> TYPE: PRT
<213> ORGANISM: artificial sequence
<220> FEATURE:
<223> OTHER INFORMATION: Uniprot P01880, IGHD_HUMAN, immunoglobulin
      heavy constant delta

<400> SEQUENCE: 12

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
                35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
                100                 105                 110

Thr Ala Gln Pro Gln Ala Glu Gly Ser Leu Ala Lys Ala Thr Thr Ala
                115                 120                 125

Pro Ala Thr Thr Arg Asn Thr Gly Arg Gly Gly Glu Glu Lys Lys Lys
                130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
                180                 185                 190

Val Gly Ser Asp Leu Lys Asp Ala His Leu Thr Trp Glu Val Ala Gly
                195                 200                 205

Lys Val Pro Thr Gly Gly Val Glu Glu Gly Leu Leu Glu Arg His Ser
                210                 215                 220
```

```
Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Arg Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 13
<211> LENGTH: 428
<212> TYPE: PRT
<213> ORGANISM: artificial sequence
<220> FEATURE:
<223> OTHER INFORMATION: Uniprot P01854, IGHE_HUMAN, immunoglobulin
      heavy constant chain epsilon

<400> SEQUENCE: 13

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
            35                  40                  45

Asn Gly Thr Thr Met Thr Leu Pro Ala Thr Thr Leu Thr Leu Ser Gly
50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly His Phe Pro
            115                 120                 125

Pro Thr Ile Gln Leu Leu Cys Leu Val Ser Gly Tyr Thr Pro Gly Thr
            130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
            165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
            195                 200                 205
```

```
Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
                260                 265                 270

Gln Arg Asn Gly Thr Leu Thr Val Thr Ser Thr Leu Pro Val Gly Thr
            275                 280                 285

Arg Asp Trp Ile Glu Gly Glu Thr Tyr Gln Cys Arg Val Thr His Pro
290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
                340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
            420                 425
```

<210> SEQ ID NO 14
<211> LENGTH: 453
<212> TYPE: PRT
<213> ORGANISM: artificial sequence
<220> FEATURE:
<223> OTHER INFORMATION: Uniprot P01871, IGHM_HUMAN, immunoglobulin heavy constant mu

<400> SEQUENCE: 14

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Phe Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
                100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
```

```
            130                 135                 140
Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
                195                 200                 205

Asn Ala Ser Ser Met Cys Val Pro Asp Gln Asp Thr Ala Ile Arg Val
            210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
            290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
            435                 440                 445

Ala Gly Thr Cys Tyr
            450

<210> SEQ ID NO 15
<211> LENGTH: 9
<212> TYPE: PRT
<213> ORGANISM: artificial sequence
<220> FEATURE:
<223> OTHER INFORMATION: Spacer 1

<400> SEQUENCE: 15

Lys Pro Cys Pro Pro Cys Lys Cys Pro
1               5

<210> SEQ ID NO 16
<211> LENGTH: 5
<212> TYPE: PRT
```

```
<213> ORGANISM: artificial sequence
<220> FEATURE:
<223> OTHER INFORMATION: linker

<400> SEQUENCE: 16

Gly Gly Gly Ser Gly
1               5

<210> SEQ ID NO 17
<211> LENGTH: 20
<212> TYPE: PRT
<213> ORGANISM: artificial sequence
<220> FEATURE:
<223> OTHER INFORMATION: human Ig kappa signal peptide

<400> SEQUENCE: 17

Met Val Leu Gln Thr Gln Val Phe Ile Ser Leu Leu Leu Trp Ile Ser
1               5                   10                  15

Gly Ala Tyr Gly
            20

<210> SEQ ID NO 18
<211> LENGTH: 22
<212> TYPE: PRT
<213> ORGANISM: artificial sequence
<220> FEATURE:
<223> OTHER INFORMATION: GM-CSF signal peptide

<400> SEQUENCE: 18

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 19
<211> LENGTH: 24
<212> TYPE: PRT
<213> ORGANISM: artificial sequence
<220> FEATURE:
<223> OTHER INFORMATION: EGFR signal peptide

<400> SEQUENCE: 19

Met Arg Pro Ser Gly Thr Ala Gly Ala Ala Leu Leu Ala Leu Leu Ala
1               5                   10                  15

Ala Leu Cys Pro Ala Ser Arg Ala
            20

<210> SEQ ID NO 20
<211> LENGTH: 16
<212> TYPE: PRT
<213> ORGANISM: artificial sequence
<220> FEATURE:
<223> OTHER INFORMATION: human CD33 signal peptide

<400> SEQUENCE: 20

Met Pro Leu Leu Leu Leu Leu Pro Leu Leu Trp Ala Gly Ala Leu Ala
1               5                   10                  15

<210> SEQ ID NO 21
<211> LENGTH: 2
<212> TYPE: PRT
<213> ORGANISM: artificial sequence
<220> FEATURE:
<223> OTHER INFORMATION: Linker
<220> FEATURE:
<221> NAME/KEY: misc_feature
```

```
<222> LOCATION: (1)..(1)
<223> OTHER INFORMATION: Wherein Gly may be repeated by an integer from
      1 to 100.
<220> FEATURE:
<221> NAME/KEY: misc_feature
<222> LOCATION: (1)..(2)
<223> OTHER INFORMATION: Wherein the sequence may be repeated by an
      integer from 1 to 100.

<400> SEQUENCE: 21

Gly Ser
1

<210> SEQ ID NO 22
<211> LENGTH: 2
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (0)..(1)
<223> OTHER INFORMATION: Wherein Ser may be repeated by an integer from
      1 to 100.
<220> FEATURE:
<221> NAME/KEY: misc_feature
<222> LOCATION: (1)..(1)
<223> OTHER INFORMATION: Wherein Gly may be repeated by an integer from
      1 to  4.
<220> FEATURE:
<221> NAME/KEY: misc_feature
<222> LOCATION: (1)..(2)
<223> OTHER INFORMATION: Wherein The sequence may be repeated by an
      integer from 1 to 50.

<400> SEQUENCE: 22

Gly Ser
1

<210> SEQ ID NO 23
<211> LENGTH: 1
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(1)
<223> OTHER INFORMATION: Wherein Gly can be repeated between 1 to 100.

<400> SEQUENCE: 23

Gly
1

<210> SEQ ID NO 24
<211> LENGTH: 2
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(2)
<223> OTHER INFORMATION: Wherein Gly Ala may be repeated between 1 and
      100.

<400> SEQUENCE: 24

Gly Ala
1

<210> SEQ ID NO 25
```

```
<211> LENGTH: 4
<212> TYPE: PRT
<213> ORGANISM: artificial sequence
<220> FEATURE:
<223> OTHER INFORMATION: Linker

<400> SEQUENCE: 25

Gly Gly Gly Gly
1

<210> SEQ ID NO 26
<211> LENGTH: 5
<212> TYPE: PRT
<213> ORGANISM: artificial sequence
<220> FEATURE:
<223> OTHER INFORMATION: Linker

<400> SEQUENCE: 26

Gly Gly Gly Ser Gly
1               5

<210> SEQ ID NO 27
<211> LENGTH: 5
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(5)
<223> OTHER INFORMATION: Wherein the sequence can be repeated between an
      integer of 1 and 100

<400> SEQUENCE: 27

Gly Gly Gly Ser Gly
1               5

<210> SEQ ID NO 28
<211> LENGTH: 5
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(5)
<223> OTHER INFORMATION: Wherein the sequence can be repeated between an
      integer of 1 and 100.

<400> SEQUENCE: 28

Gly Gly Gly Gly Ser
1               5

<210> SEQ ID NO 29
<211> LENGTH: 4
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(4)
<223> OTHER INFORMATION: Wherein the sequence can be repeated between an
      integer of 1 and 100

<400> SEQUENCE: 29

Gly Gly Gly Ser
1
```

```
<210> SEQ ID NO 30
<211> LENGTH: 3
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(3)
<223> OTHER INFORMATION: Wherein the sequence can be repeated between an
      integer of 1 and 100

<400> SEQUENCE: 30

Gly Gly Ser
1

<210> SEQ ID NO 31
<211> LENGTH: 6
<212> TYPE: PRT
<213> ORGANISM: artificial sequence
<220> FEATURE:
<223> OTHER INFORMATION: Linker

<400> SEQUENCE: 31

Gly Ser Gly Ser Gly Ser
1               5

<210> SEQ ID NO 32
<211> LENGTH: 5
<212> TYPE: PRT
<213> ORGANISM: artificial sequence
<220> FEATURE:
<223> OTHER INFORMATION: Linker

<400> SEQUENCE: 32

Gly Gly Ser Gly Gly
1               5

<210> SEQ ID NO 33
<211> LENGTH: 7
<212> TYPE: PRT
<213> ORGANISM: artificial sequence
<220> FEATURE:
<223> OTHER INFORMATION: Linker

<400> SEQUENCE: 33

Ser Gly Gly Ser Gly Gly Ser
1               5

<210> SEQ ID NO 34
<211> LENGTH: 15
<212> TYPE: PRT
<213> ORGANISM: artificial sequence
<220> FEATURE:
<223> OTHER INFORMATION: Linker

<400> SEQUENCE: 34

Gly Gly Ser Gly Gly Ser Gly Gly Ser Gly Gly Ser Gly Gly Gly
1               5                   10                  15

<210> SEQ ID NO 35
<211> LENGTH: 16
<212> TYPE: PRT
<213> ORGANISM: artificial sequence
<220> FEATURE:
<223> OTHER INFORMATION: Linker

<400> SEQUENCE: 35
```

```
Gly Gly Ser Gly Gly Ser Gly Gly Gly Gly Ser Gly Gly Gly Ser
1               5                   10                  15

<210> SEQ ID NO 36
<211> LENGTH: 15
<212> TYPE: PRT
<213> ORGANISM: artificial sequence
<220> FEATURE:
<223> OTHER INFORMATION: Linker

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 19
<212> TYPE: PRT
<213> ORGANISM: artificial sequence
<220> FEATURE:
<223> OTHER INFORMATION: P2A

<400> SEQUENCE: 37

Ala Thr Asn Phe Ser Leu Leu Lys Gln Ala Gly Asp Val Glu Glu Asn
1               5                   10                  15

Pro Gly Pro

<210> SEQ ID NO 38
<211> LENGTH: 18
<212> TYPE: PRT
<213> ORGANISM: artificial sequence
<220> FEATURE:
<223> OTHER INFORMATION: T2A

<400> SEQUENCE: 38

Glu Gly Arg Gly Ser Leu Leu Thr Cys Gly Asp Val Glu Glu Asn Pro
1               5                   10                  15

Gly Pro

<210> SEQ ID NO 39
<211> LENGTH: 22
<212> TYPE: PRT
<213> ORGANISM: artificial sequence
<220> FEATURE:
<223> OTHER INFORMATION: F2A

<400> SEQUENCE: 39

Val Lys Gln Thr Leu Asn Phe Asp Leu Leu Lys Leu Ala Gly Asp Val
1               5                   10                  15

Glu Ser Asn Pro Gly Pro
                20

<210> SEQ ID NO 40
<211> LENGTH: 20
<212> TYPE: PRT
<213> ORGANISM: artificial sequence
<220> FEATURE:
<223> OTHER INFORMATION: E2A

<400> SEQUENCE: 40

Gln Cys Thr Asn Tyr Ala Leu Leu Lys Leu Ala Gly Asp Val Glu Ser
1               5                   10                  15

Asn Pro Gly Pro
                20
```

```
<210> SEQ ID NO 41
<211> LENGTH: 4
<212> TYPE: PRT
<213> ORGANISM: artificial sequence
<220> FEATURE:
<223> OTHER INFORMATION: Furin Cleavage Site

<400> SEQUENCE: 41

Arg Ala Lys Arg
1

<210> SEQ ID NO 42
<211> LENGTH: 5
<212> TYPE: PRT
<213> ORGANISM: artificial sequence
<220> FEATURE:
<223> OTHER INFORMATION: Linker
<220> FEATURE:
<221> NAME/KEY: misc_feature
<222> LOCATION: (1)..(5)
<223> OTHER INFORMATION: Wherein the sequence can be repeated by a
      positive integer equal to, or greater than 1

<400> SEQUENCE: 42

Gly Gly Gly Gly Ser
1               5

<210> SEQ ID NO 43
<211> LENGTH: 20
<212> TYPE: PRT
<213> ORGANISM: artificial sequence
<220> FEATURE:
<223> OTHER INFORMATION: Linker

<400> SEQUENCE: 43

Gly Gly Gly Gly Ser Gly Gly Gly Gly Ser Gly Gly Gly Gly Ser Gly
1               5                   10                  15

Gly Gly Gly Ser
            20

<210> SEQ ID NO 44
<211> LENGTH: 121
<212> TYPE: PRT
<213> ORGANISM: artificial sequence
<220> FEATURE:
<223> OTHER INFORMATION: R12 VH

<400> SEQUENCE: 44

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120
```

```
<210> SEQ ID NO 45
<211> LENGTH: 5
<212> TYPE: PRT
<213> ORGANISM: artificial sequence
<220> FEATURE:
<223> OTHER INFORMATION: R12 VH CDR1

<400> SEQUENCE: 45

Ala Tyr Tyr Met Ser
1               5

<210> SEQ ID NO 46
<211> LENGTH: 17
<212> TYPE: PRT
<213> ORGANISM: artificial sequence
<220> FEATURE:
<223> OTHER INFORMATION: R12 VH CDR2

<400> SEQUENCE: 46

Thr Ile Tyr Pro Ser Ser Gly Lys Thr Tyr Ala Thr Trp Val Asn
1               5                   10                  15

Gly

<210> SEQ ID NO 47
<211> LENGTH: 12
<212> TYPE: PRT
<213> ORGANISM: artificial sequence
<220> FEATURE:
<223> OTHER INFORMATION: R12 VH CDR3

<400> SEQUENCE: 47

Asp Ser Tyr Ala Asp Asp Gly Ala Leu Phe Asn Ile
1               5                   10

<210> SEQ ID NO 48
<211> LENGTH: 112
<212> TYPE: PRT
<213> ORGANISM: artificial sequence
<220> FEATURE:
<223> OTHER INFORMATION: R12 VL

<400> SEQUENCE: 48

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
            100                 105                 110

<210> SEQ ID NO 49
<211> LENGTH: 12
<212> TYPE: PRT
<213> ORGANISM: artificial sequence
<220> FEATURE:
```

```
<223> OTHER INFORMATION: R12 VL CDR1

<400> SEQUENCE: 49

Thr Leu Ser Ser Ala His Lys Thr Asp Thr Ile Asp
1               5                   10

<210> SEQ ID NO 50
<211> LENGTH: 7
<212> TYPE: PRT
<213> ORGANISM: artificial sequence
<220> FEATURE:
<223> OTHER INFORMATION: R12 VL CDR2

<400> SEQUENCE: 50

Gly Ser Tyr Thr Lys Arg Pro
1               5

<210> SEQ ID NO 51
<211> LENGTH: 9
<212> TYPE: PRT
<213> ORGANISM: artificial sequence
<220> FEATURE:
<223> OTHER INFORMATION: R12 VL CDR3

<400> SEQUENCE: 51

Gly Ala Asp Tyr Ile Gly Gly Tyr Val
1               5

<210> SEQ ID NO 52
<211> LENGTH: 248
<212> TYPE: PRT
<213> ORGANISM: artificial sequence
<220> FEATURE:
<223> OTHER INFORMATION: R12 scFv

<400> SEQUENCE: 52

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
                20                  25                  30

Tyr Met Ser Trp Val Arg Gln Ala Pro Gly Lys Gly Leu Glu Trp Ile
            35                  40                  45

Ala Thr Ile Tyr Pro Ser Ser Gly Lys Thr Tyr Tyr Ala Thr Trp Val
        50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Gly Gly Gly Ser Gly Gly
        115                 120                 125

Gly Gly Ser Gly Gly Gly Ser Glu Leu Val Leu Thr Gln Ser Pro
    130                 135                 140

Ser Val Ser Ala Ala Leu Gly Ser Pro Ala Lys Ile Thr Cys Thr Leu
145                 150                 155                 160

Ser Ser Ala His Lys Thr Asp Thr Ile Asp Trp Tyr Gln Gln Leu Gln
                165                 170                 175

Gly Glu Ala Pro Arg Tyr Leu Met Gln Val Gln Ser Asp Gly Ser Tyr
            180                 185                 190
```

Thr Lys Arg Pro Gly Val Pro Asp Arg Phe Ser Gly Ser Ser Ser Gly
            195                 200                 205

Ala Asp Arg Tyr Leu Ile Ile Pro Ser Val Gln Ala Asp Asp Glu Ala
            210                 215                 220

Asp Tyr Tyr Cys Gly Ala Asp Tyr Ile Gly Gly Tyr Val Phe Gly Gly
225                 230                 235                 240

Gly Thr Gln Leu Thr Val Thr Gly
                245

<210> SEQ ID NO 53
<211> LENGTH: 42
<212> TYPE: PRT
<213> ORGANISM: artificial sequence
<220> FEATURE:
<223> OTHER INFORMATION: 4-1BB costimulatory domain

<400> SEQUENCE: 53

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 54
<211> LENGTH: 28
<212> TYPE: PRT
<213> ORGANISM: artificial sequence
<220> FEATURE:
<223> OTHER INFORMATION: CD28 transmembrane domain

<400> SEQUENCE: 54

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 55
<211> LENGTH: 112
<212> TYPE: PRT
<213> ORGANISM: artificial sequence
<220> FEATURE:
<223> OTHER INFORMATION: CD3zeta activating domain

<400> SEQUENCE: 55

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

-continued

```
<210> SEQ ID NO 56
<211> LENGTH: 23
<212> TYPE: PRT
<213> ORGANISM: artificial sequence
<220> FEATURE:
<223> OTHER INFORMATION: p2A

<400> SEQUENCE: 56

Ser Gly Ser Gly Ala Thr Asn Phe Ser Leu Leu Lys Gln Ala Gly Asp
1               5                   10                  15

Val Glu Glu Asn Pro Gly Pro
            20

<210> SEQ ID NO 57
<211> LENGTH: 1198
<212> TYPE: PRT
<213> ORGANISM: artificial sequence
<220> FEATURE:
<223> OTHER INFORMATION: c-jun-anti-ROR1 CAR

<400> SEQUENCE: 57

Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
        35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
        115                 120                 125

Ser Val Thr Ser Ala Ala Gln Pro Val Asn Gly Ala Gly Met Val Ala
    130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285
```

```
Ala Gln Asn Ser Glu Leu Ala Ser Thr Ala Asn Met Leu Arg Glu Gln
    290                 295                 300
Val Ala Gln Leu Lys Gln Lys Val Met Asn His Val Asn Ser Gly Cys
305                 310                 315                 320
Gln Leu Met Leu Thr Gln Gln Leu Gln Thr Phe Gly Ser Gly Ala Thr
                    325                 330                 335
Asn Phe Ser Leu Leu Lys Gln Ala Gly Asp Val Glu Glu Asn Pro Gly
                340                 345                 350
Pro Met Val Leu Gln Thr Gln Val Phe Ile Ser Leu Leu Leu Trp Ile
            355                 360                 365
Ser Gly Ala Tyr Gly Gln Glu Gln Leu Val Glu Ser Gly Gly Arg Leu
370                 375                 380
Val Thr Pro Gly Gly Ser Leu Thr Leu Ser Cys Lys Ala Ser Gly Phe
385                 390                 395                 400
Asp Phe Ser Ala Tyr Tyr Met Ser Trp Val Arg Gln Ala Pro Gly Lys
                405                 410                 415
Gly Leu Glu Trp Ile Ala Thr Ile Tyr Pro Ser Ser Gly Lys Thr Tyr
            420                 425                 430
Tyr Ala Thr Trp Val Asn Gly Arg Phe Thr Ile Ser Ser Asp Asn Ala
        435                 440                 445
Gln Asn Thr Val Asp Leu Gln Met Asn Ser Leu Thr Ala Ala Asp Arg
    450                 455                 460
Ala Thr Tyr Phe Cys Ala Arg Asp Ser Tyr Ala Asp Asp Gly Ala Leu
465                 470                 475                 480
Phe Asn Ile Trp Gly Pro Gly Thr Leu Val Thr Ile Ser Ser Gly Gly
                485                 490                 495
Gly Gly Ser Gly Gly Gly Gly Ser Gly Gly Gly Gly Ser Glu Leu Val
            500                 505                 510
Leu Thr Gln Ser Pro Ser Val Ser Ala Ala Leu Gly Ser Pro Ala Lys
        515                 520                 525
Ile Thr Cys Thr Leu Ser Ser Ala His Lys Thr Asp Thr Ile Asp Trp
    530                 535                 540
Tyr Gln Gln Leu Gln Gly Glu Ala Pro Arg Tyr Leu Met Gln Val Gln
545                 550                 555                 560
Ser Asp Gly Ser Tyr Thr Lys Arg Pro Gly Val Pro Asp Arg Phe Ser
                565                 570                 575
Gly Ser Ser Ser Gly Ala Asp Arg Tyr Leu Ile Ile Pro Ser Val Gln
            580                 585                 590
Ala Asp Asp Glu Ala Asp Tyr Tyr Cys Gly Ala Asp Tyr Ile Gly Gly
        595                 600                 605
Tyr Val Phe Gly Gly Gly Thr Gln Leu Thr Val Thr Gly Gly Gly Gly
    610                 615                 620
Ser Gly Lys Pro Cys Pro Pro Cys Lys Cys Pro Met Phe Trp Val Leu
625                 630                 635                 640
Val Val Val Gly Gly Val Leu Ala Cys Tyr Ser Leu Leu Val Thr Val
                645                 650                 655
Ala Phe Ile Ile Phe Trp Val Lys Arg Gly Arg Lys Lys Leu Leu Tyr
            660                 665                 670
Ile Phe Lys Gln Pro Phe Met Arg Pro Val Gln Thr Thr Gln Glu Glu
        675                 680                 685
Asp Gly Cys Ser Cys Arg Phe Pro Glu Glu Glu Glu Gly Gly Cys Glu
    690                 695                 700

Leu Arg Val Lys Phe Ser Arg Ser Ala Asp Ala Pro Ala Tyr Gln Gln
```

-continued

```
705                 710                 715                 720
Gly Gln Asn Gln Leu Tyr Asn Glu Leu Asn Leu Gly Arg Arg Glu Glu
                725                 730                 735
Tyr Asp Val Leu Asp Lys Arg Gly Arg Asp Pro Glu Met Gly Gly
                740                 745                 750
Lys Pro Arg Arg Lys Asn Pro Gln Glu Gly Leu Tyr Asn Glu Leu Gln
                755                 760                 765
Lys Asp Lys Met Ala Glu Ala Tyr Ser Glu Ile Gly Met Lys Gly Glu
                770                 775                 780
Arg Arg Arg Gly Lys Gly His Asp Gly Leu Tyr Gln Gly Leu Ser Thr
785                 790                 795                 800
Ala Thr Lys Asp Thr Tyr Asp Ala Leu His Met Gln Ala Leu Pro Pro
                805                 810                 815
Arg Ser Gly Ala Thr Asn Phe Ser Leu Leu Lys Gln Ala Gly Asp Val
                820                 825                 830
Glu Glu Asn Pro Gly Pro Met Leu Leu Leu Val Thr Ser Leu Leu Leu
                835                 840                 845
Cys Glu Leu Pro His Pro Ala Phe Leu Leu Ile Pro Arg Lys Val Cys
                850                 855                 860
Asn Gly Ile Gly Ile Gly Glu Phe Lys Asp Ser Leu Ser Ile Asn Ala
865                 870                 875                 880
Thr Asn Ile Lys His Phe Lys Asn Cys Thr Ser Ile Ser Gly Asp Leu
                885                 890                 895
His Ile Leu Pro Val Ala Phe Arg Gly Asp Ser Phe Thr His Thr Pro
                900                 905                 910
Pro Leu Asp Pro Gln Glu Leu Asp Ile Leu Lys Thr Val Lys Glu Ile
                915                 920                 925
Thr Gly Phe Leu Leu Ile Gln Ala Trp Pro Glu Asn Arg Thr Asp Leu
                930                 935                 940
His Ala Phe Glu Asn Leu Glu Ile Ile Arg Gly Arg Thr Lys Gln His
945                 950                 955                 960
Gly Gln Phe Ser Leu Ala Val Val Ser Leu Asn Ile Thr Ser Leu Gly
                965                 970                 975
Leu Arg Ser Leu Lys Glu Ile Ser Asp Gly Asp Val Ile Ile Ser Gly
                980                 985                 990
Asn Lys Asn Leu Cys Tyr Ala Asn Thr Ile Asn Trp Lys Lys Leu Phe
                995                 1000                1005
Gly Thr Ser Gly Gln Lys Thr Lys Ile Ile Ser Asn Arg Gly Glu
                1010                1015                1020
Asn Ser Cys Lys Ala Thr Gly Gln Val Cys His Ala Leu Cys Ser
                1025                1030                1035
Pro Glu Gly Cys Trp Gly Pro Glu Pro Arg Asp Cys Val Ser Cys
                1040                1045                1050
Arg Asn Val Ser Arg Gly Arg Glu Cys Val Asp Lys Cys Asn Leu
                1055                1060                1065
Leu Glu Gly Glu Pro Arg Glu Phe Val Glu Asn Ser Glu Cys Ile
                1070                1075                1080
Gln Cys His Pro Glu Cys Leu Pro Gln Ala Met Asn Ile Thr Cys
                1085                1090                1095
Thr Gly Arg Gly Pro Asp Asn Cys Ile Gln Cys Ala His Tyr Ile
                1100                1105                1110
Asp Gly Pro His Cys Val Lys Thr Cys Pro Ala Gly Val Met Gly
                1115                1120                1125
```

| Glu | Asn | Asn | Thr | Leu | Val | Trp | Lys | Tyr | Ala | Asp | Ala | Gly | His | Val |
|---|---|---|---|---|---|---|---|---|---|---|---|---|---|---|
| | 1130 | | | | 1135 | | | | 1140 | | | | | |

Cys His Leu Cys His Pro Asn Cys Thr Tyr Gly Cys Thr Gly Pro
  1145              1150              1155

Gly Leu Glu Gly Cys Pro Thr Asn Gly Pro Lys Ile Pro Ser Ile
  1160              1165              1170

Ala Thr Gly Met Val Gly Ala Leu Leu Leu Leu Val Val Ala
  1175              1180              1185

Leu Gly Ile Gly Leu Phe Met Arg Arg Arg
  1190              1195

```
<210> SEQ ID NO 58
<211> LENGTH: 4022
<212> TYPE: DNA
<213> ORGANISM: artificial sequence
<220> FEATURE:
<223> OTHER INFORMATION: DNA construct

<400> SEQUENCE: 58
tgaaagaccc cacctgtagg tttggcaagc taggatcaag gttaggaaca gagagacagc      60
agaatatggg ccaaacagga tatctgtggt aagcagttcc tgccccggct cagggccaag     120
aacagttgga acagcagaat atgggccaaa caggatatct gtggtaagca gttcctgccc     180
cggctcaggg ccaagaacag atggtcccca gatgcggtcc cgccctcagc agtttctaga     240
gaaccatcag atgtttccag ggtgccccaa ggacctgaaa tgaccctgtg ccttatttga     300
actaaccaat cagttcgctt ctcgcttctg ttcgcgcgct tctgctcccc gagctcaata     360
aaagagccca accccctca ctcggcgcga tcagaacctc ttacgagtcg gctagcgccg      420
ccaccatgac agccaagatg gaaaccacat tctacgacga cgccctgaac gcctcattcc     480
tgccttctga gagcggacct tacggctaca gcaatcctaa gatcctgaaa cagagcatga     540
cccttaacct ggctgatcct gttggaagcc tgaaacctca cctgagagcc aaaaacagcg     600
acctgctcac cagccctgat gtgggcctgc tgaagctggc ctctccagag ctggaacggc     660
tgatcatcca gagcagcaac ggccacatca aaccacccc taccctaca caattcctgt       720
gccctaagaa cgtgaccgac gagcaggagg cttcgccga aggctttgtg cgggccctgg      780
cagaactgca ctctcagaac accctgccta gcgtgacctc cgccgcccag cctgtcaacg     840
gcgccggaat ggtggcccct gccgtggctt ctgtggccgg cggcagcggc agcggcggat     900
tcagcgcctc tctgcactct gagcctcctg tctacgccaa tctgtctaat ttcaaccccg     960
gagccctgtc cagcggcggc ggagctccta gctacggcgc tgctggactg gccttccccg    1020
cccagcccca gcaacagcag cagcctccac accacctgcc cagcagatgc ccgtgcagc     1080
accctagact gcaggccctg aaggaagaac ccaaacagt gcctgagatg cctggcgaga    1140
cacctccact gagccccatc gacatggaaa gccaggagcg gatcaaggcc gagagaaaga    1200
gaatgcggaa cagaatcgcc gctagcaagt gcagaaagcg gaagctggaa agaatcgcca    1260
gactggaaga gaaggtgaag accctgaaag cccaaaatag cgagctggcc agcaccgcca    1320
acatgctgcg ggaacaggtg gcccagctga agcagaaggt gatgaaccac gtgaactctg    1380
gttgtcagct gatgctgacc cagcagctcc agaccttcgg ctccggtgca cgaacttca    1440
gcctgctgaa gcaggccgga gatgttgagg aaaatccagg tcccatggtc ttgcagactc    1500
aagtatttat atcccttttg ctctggatct ctggagctta cggccaggaa cagctcgtcg    1560
aaagcggcgg cagactggtg acacctggcg gcagcctgac cctgagctgc aaggccagcg    1620
```

```
gcttcgactt cagcgcctac tacatgagct gggtccgcca ggcccctggc aagggactgg    1680
aatggatcgc caccatctac cccagcagcg gcaagaccta ctacgccacc tgggtgaacg    1740
gacggttcac catctccagc gacaacgccc agaacaccgt ggacctgcag atgaacagcc    1800
tgacagccgc cgaccgggcc acctactttt gcgctcggga cagctacgcc gacgacggcg    1860
ccctgttcaa catctggggc cctggcaccc tggtgacaat ctctagcggc ggaggcggat    1920
ctggtggcgg aggaagtggc ggcggaggat ctgagctggt gctgacccag agcccctctg    1980
tgtctgctgc cctgggaagc cctgccaaga tcacctgtac cctgagcagc gcccacaaga    2040
ccgacaccat cgactggtat cagcagctgc agggcgaggc ccccagatac ctgatgcagg    2100
tgcagagcga cggcagctac accaagaggc caggcgtgcc cgacaggttc agcggatcta    2160 gctctgcgc cgaccgctac ctgatcatcc ccagcgtgca ggccgatgac gaggccgatt    2220
actactgtgg cgccgactac atcggcggct acgtgttcgg cggaggcacc cagctgaccg    2280
tgaccggtgg cggaggttca ggcaaaccgt gccctccgtg caagtgtcct atgttctggg    2340
tgctggtggt ggtcggaggc gtgctggcct gctacagcct gctggtcacc gtggccttca    2400
tcatcttttg ggtgaaacgg ggcagaaaga aactcctgta tatattcaaa caaccattta    2460
tgagaccagt acaaactact caagaggaag atggctgtag ctgccgattt ccagaagaag    2520
aagaaggagg atgtgaactg cgggtgaagt tcagcagaag cgccgacgcc cctgcctacc    2580
agcagggcca gaatcagctg tacaacgagc tgaacctggg cagaagggaa gagtacgacg    2640
tcctggataa gcgagaggc cgggaccctg agatgggcgg caagcctcgg cggaagaacc    2700
cccaggaagg cctgtataac gaactgcaga agacaagat ggccgaggcc tacagcgaga    2760
tcggcatgaa gggcgagcgg aggcggggca agggccacga cggcctgtat cagggcctgt    2820
ccaccgccac caaggatacc tacgacgccc tgcacatgca ggccctgccc ccaaggtccg    2880
gagccactaa cttctcccctg ttgaaacaag caggggatgt cgaagagaat cccgggccaa    2940
tgcttctcct ggtgacaagc cttctgctct gtgaattacc acacccagca ttcctcctga    3000
tcccacgcaa agtgtgcaac ggaataggta ttggtgaatt taaggactca ctctccataa    3060
atgctacgaa tattaaacac ttcaaaaact gcacctccat cagtggcgat ctccacatcc    3120
tgccggtggc atttaggggt gactccttca cacatactcc tcctctggac ccacaagaac    3180
tggatattct gaaaaccgta aaggaaatca cagggttttt gctgattcaa gcttggcctg    3240
aaaacaggac ggacctccat gcctttgaga acctagaaat catacgcggc aggaccaagc    3300
agcatggaca gttttctctt gctgtcgtga gcctgaacat aacatccttg ggattacgct    3360
ccctcaagga gataagtgat ggagatgtga taatttcagg aaacaaaaat tgtgctatg    3420 caaatacaat aaaactggaa aaactgtttg gacctccgg ccagaaaacc aaaattataa    3480
gcaacagagg cgaaaacagc tgcaaggcca caggccaggt ctgccatgcc ttgtgctccc    3540
ccgagggctg ctgggcccg gagcccaggg attgcgtgtc ttgccggaat gtcagccgag    3600
gcagggaatg cgtggacaag tgcaaccttc tggaaggcga gccaagggag tttgtggaga    3660
actctgagtg catacagtgc cacccagagt gcctgcctca ggccatgaac atcacctgca    3720
caggacgggg accagacaac tgtatccagt gtgcccacta cattgacggc ccccactgcg    3780
tcaagacctg cccggcagga gtcatgggag aaaacaacac cctggtctgg aagtacgcag    3840
acgccggcca tgtgtgccac ctgtgccatc caaactgcac ctacggatgc actgggccag    3900
gtcttgaagg ctgtccaacg aacgggccta agatcccgtc catcgccact gggatggtgg    3960
```

```
gggccctcct cttgctgctg gtggtggccc tggggatcgg cctcttcatg cgccgaaggt    4020
ga                                                                   4022
```

<210> SEQ ID NO 59
<211> LENGTH: 352
<212> TYPE: PRT
<213> ORGANISM: artificial sequence
<220> FEATURE:
<223> OTHER INFORMATION: c-Jun after P2A cleavage

<400> SEQUENCE: 59

```
Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
        35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
        115                 120                 125

Ser Val Thr Ser Ala Ala Gln Pro Val Asn Gly Ala Gly Met Val Ala
    130                 135                 140

Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
    290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe Gly Ser Gly Ala Thr
                325                 330                 335

Asn Phe Ser Leu Leu Lys Gln Ala Gly Asp Val Glu Glu Asn Pro Gly
            340                 345                 350
```

<210> SEQ ID NO 60
<211> LENGTH: 21
<212> TYPE: PRT
<213> ORGANISM: artificial sequence
<220> FEATURE:
<223> OTHER INFORMATION: hIgK after P2A cleavage

<400> SEQUENCE: 60

Pro Met Val Leu Gln Thr Gln Val Phe Ile Ser Leu Leu Trp Ile
1               5                   10                  15

Ser Gly Ala Tyr Gly
            20

<210> SEQ ID NO 61
<211> LENGTH: 133
<212> TYPE: PRT
<213> ORGANISM: artificial sequence
<220> FEATURE:
<223> OTHER INFORMATION: CD3z after P2A cleavage

<400> SEQUENCE: 61

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

Ser Gly Ala Thr Asn Phe Ser Leu Leu Lys Gln Ala Gly Asp Val Glu
        115                 120                 125

Glu Asn Pro Gly Pro
    130

<210> SEQ ID NO 62
<211> LENGTH: 23
<212> TYPE: PRT
<213> ORGANISM: artificial sequence
<220> FEATURE:
<223> OTHER INFORMATION: GMCSFR-alpha-SP after P2A cleavage

<400> SEQUENCE: 62

Pro Met Leu Leu Leu Val Thr Ser Leu Leu Cys Glu Leu Pro His
1               5                   10                  15

Pro Ala Phe Leu Leu Ile Pro
            20

<210> SEQ ID NO 63
<211> LENGTH: 18
<212> TYPE: PRT
<213> ORGANISM: artificial sequence
<220> FEATURE:
<223> OTHER INFORMATION: Linker

<400> SEQUENCE: 63

```
Gly Gly Ser Gly Gly Ser Gly Gly Ser Gly Gly Ser Gly Gly Ser Gly
1               5                   10                  15

Gly Ser

<210> SEQ ID NO 64
<211> LENGTH: 386
<212> TYPE: DNA
<213> ORGANISM: artificial sequence
<220> FEATURE:
<223> OTHER INFORMATION: MND promotor

<400> SEQUENCE: 64
tgaaagaccc cacctgtagg tttggcaagc taggatcaag gttaggaaca gagagacagc      60
agaatatggg ccaaacagga tatctgtggt aagcagttcc tgccccggct cagggccaag     120
aacagttgga acagcagaat atgggccaaa caggatatct gtggtaagca gttcctgccc     180
cggctcaggg ccaagaacag atggtcccca gatgcggtcc cgccctcagc agtttctaga     240
gaaccatcag atgtttccag ggtgcccaa ggacctgaaa tgaccctgtg ccttatttga      300
actaaccaat cagttcgctt ctcgcttctg ttcgcgcgct tctgctcccc gagctcaata     360
aaagagccca caaccctca ctcggc                                           386
```